United States Patent
Samuel et al.

(10) Patent No.: US 12,228,987 B2
(45) Date of Patent: Feb. 18, 2025

(54) METHOD FOR ENERGY DELIVERY FOR MODULAR ENERGY SYSTEM

(71) Applicant: Cilag GmbH International, Zug (CH)

(72) Inventors: Jonathan T. Samuel, Blue Ash, OH (US); Eitan T. Wiener, Loveland, OH (US); Joshua P. Morgan, Loveland, OH (US); Andrew W. Carroll, Cincinnati, OH (US); Joshua M. Henderson, Montgomery, OH (US)

(73) Assignee: Cilag GmbH International, Zug (CH)

( * ) Notice: Subject to any disclaimer, the term of this patent is extended or adjusted under 35 U.S.C. 154(b) by 450 days.

(21) Appl. No.: 17/217,424

(22) Filed: Mar. 30, 2021

(65) Prior Publication Data

US 2022/0317751 A1 Oct. 6, 2022

(51) Int. Cl.
*G06F 1/28* (2006.01)
*A61B 34/00* (2016.01)
(Continued)

(52) U.S. Cl.
CPC ............ *G06F 1/28* (2013.01); *G06F 1/266* (2013.01); *H02J 3/001* (2020.01); *H03M 1/66* (2013.01);
(Continued)

(58) Field of Classification Search
CPC .. G06F 1/28; G06F 1/266; H02J 3/001; H02J 2310/23; H03M 1/66; A61B 34/25; A61B 90/37; A61B 2090/372
See application file for complete search history.

(56) References Cited

U.S. PATENT DOCUMENTS 4,171,700 A  10/1979 Farin
4,378,801 A  4/1983 Oosten
(Continued)

FOREIGN PATENT DOCUMENTS

EP  0408160 A1  1/1991
EP  0473987 A1  3/1992
(Continued)

OTHER PUBLICATIONS

Zhu et al. "Haptic-feedback smart glove as a creative human-machine interface (HMI) for virtual/augmented reality applications," Sci. Adv, vol. 6, No. 19, May 8, 2020.
(Continued)

*Primary Examiner* — Rexford N Barnie
*Assistant Examiner* — Thai H Tran

(57) ABSTRACT

A method of delivering power to a load coupled to an energy module includes determining a power to be produced in a load, generating a signal, and selecting a first or second power amplifier circuit based on the power to be produced in the load. The power rating of the amplifier circuits is different. Another method includes generating a digital waveform having a predetermined wave shape and frequency, converting the digital waveform to an analog waveform, selecting a first power amplifier circuit or a second power amplifier circuit based on a predetermined power output to be produced by the first or second power amplifier circuit into a load coupled to an energy output port of the energy module, coupling the analog waveform to the selected first or second power amplifier circuit, and producing the predetermined power output into the load.

16 Claims, 36 Drawing Sheets

(51) Int. Cl.
*G06F 1/26* (2006.01)
*H02J 3/00* (2006.01)
*H03M 1/66* (2006.01)
*A61B 90/00* (2016.01)

(52) U.S. Cl.
CPC ............ *A61B 34/25* (2016.02); *A61B 90/37* (2016.02); *A61B 2090/372* (2016.02); *H02J 2310/23* (2020.01)

(56) References Cited

U.S. PATENT DOCUMENTS

| | | | |
|---|---|---|---|
| 4,640,279 A | 2/1987 | Beard | |
| 4,849,752 A | 7/1989 | Bryant | |
| D303,787 S | 10/1989 | Messenger et al. | |
| 5,041,110 A | 8/1991 | Fleenor | |
| D327,061 S | 6/1992 | Soren et al. | |
| 5,189,277 A | 2/1993 | Boisvert et al. | |
| 5,204,669 A | 4/1993 | Dorfe et al. | |
| 5,318,563 A | 6/1994 | Malis et al. | |
| 5,325,270 A | 6/1994 | Wenger et al. | |
| 5,383,880 A | 1/1995 | Hooven | |
| 5,395,033 A | 3/1995 | Byrne et al. | |
| 5,425,375 A | 6/1995 | Chin et al. | |
| 5,613,158 A | 3/1997 | Savage | |
| D379,346 S | 5/1997 | Mieki | |
| 5,667,517 A | 9/1997 | Hooven | |
| 5,690,504 A | 11/1997 | Scanlan et al. | |
| 5,693,042 A | 12/1997 | Boiarski et al. | |
| 5,724,468 A | 3/1998 | Leone et al. | |
| 5,788,688 A | 8/1998 | Bauer et al. | |
| 5,817,119 A | 10/1998 | Klieman et al. | |
| 5,849,020 A | 12/1998 | Long et al. | |
| 5,865,361 A | 2/1999 | Milliman et al. | |
| 5,872,481 A * | 2/1999 | Sevic .............. | H04B 1/0483 330/51 |
| 5,901,150 A | 5/1999 | Jhuboo et al. | |
| 5,910,139 A | 6/1999 | Cochran et al. | |
| 5,941,846 A | 8/1999 | Duffy et al. | |
| 6,019,745 A | 2/2000 | Gray | |
| 6,049,467 A | 4/2000 | Tamarkin et al. | |
| 6,055,062 A | 4/2000 | Dina et al. | |
| 6,055,458 A | 4/2000 | Cochran et al. | |
| D431,811 S | 10/2000 | Nishio et al. | |
| 6,179,136 B1 | 1/2001 | Kluge et al. | |
| 6,269,411 B1 | 7/2001 | Reasoner | |
| 6,273,750 B1 | 8/2001 | Malkowski, Jr. | |
| 6,288,606 B1 | 9/2001 | Ekman et al. | |
| H2037 H | 7/2002 | Yates et al. | |
| 6,416,471 B1 | 7/2002 | Kumar et al. | |
| 6,546,270 B1 | 4/2003 | Goldin et al. | |
| 6,584,358 B2 | 6/2003 | Carter et al. | |
| 6,611,793 B1 | 8/2003 | Burnside et al. | |
| 6,731,514 B2 | 5/2004 | Evans | |
| 6,760,218 B2 | 7/2004 | Fan | |
| 6,839,238 B2 | 1/2005 | Derr et al. | |
| 6,843,657 B2 | 1/2005 | Driscoll et al. | |
| 6,888,848 B2 | 5/2005 | Beshai et al. | |
| 6,913,471 B2 | 7/2005 | Smith | |
| 7,009,511 B2 | 3/2006 | Mazar et al. | |
| 7,044,949 B2 | 5/2006 | Orszulak et al. | |
| 7,074,205 B1 | 7/2006 | Duffy et al. | |
| 7,134,994 B2 | 11/2006 | Alpert et al. | |
| 7,171,784 B2 | 2/2007 | Eenigenburg | |
| 7,217,269 B2 | 5/2007 | El-Galley et al. | |
| 7,252,664 B2 | 8/2007 | Nasab et al. | |
| 7,268,684 B2 | 9/2007 | Tethrake et al. | |
| 7,331,699 B2 | 2/2008 | Gawalkiewicz et al. | |
| 7,344,532 B2 | 3/2008 | Goble et al. | |
| 7,353,068 B2 | 4/2008 | Tanaka et al. | |
| D575,792 S | 8/2008 | Benson | |
| 7,408,439 B2 | 8/2008 | Wang et al. | |
| D579,876 S | 11/2008 | Novotney et al. | |
| D583,328 S | 12/2008 | Chiang | |
| 7,496,418 B2 | 2/2009 | Kim et al. | |
| D589,447 S | 3/2009 | Sasada et al. | |
| 7,500,747 B2 | 3/2009 | Howell et al. | |
| 7,518,502 B2 | 4/2009 | Austin et al. | |
| 7,563,259 B2 | 7/2009 | Takahashi | |
| 7,601,149 B2 | 10/2009 | DiCarlo et al. | |
| 7,637,907 B2 | 12/2009 | Blaha | |
| 7,656,671 B2 | 2/2010 | Liu et al. | |
| 7,695,485 B2 | 4/2010 | Whitman et al. | |
| 7,757,028 B2 | 7/2010 | Druke et al. | |
| D631,252 S | 1/2011 | Leslie | |
| 7,932,826 B2 | 4/2011 | Fritchie et al. | |
| 7,945,065 B2 | 5/2011 | Menzl et al. | |
| 7,945,342 B2 | 5/2011 | Tsai et al. | |
| 7,982,776 B2 | 7/2011 | Dunki-Jacobs et al. | |
| 7,995,045 B2 | 8/2011 | Dunki-Jacobs | |
| 8,019,094 B2 | 9/2011 | Hsieh et al. | |
| 8,057,492 B2 | 11/2011 | Ortiz et al. | |
| D655,678 S | 3/2012 | Kobayashi et al. | |
| D657,368 S | 4/2012 | Magee et al. | |
| 8,187,263 B2 | 5/2012 | Behnke et al. | |
| 8,218,279 B2 | 7/2012 | Liao et al. | |
| 8,239,066 B2 | 8/2012 | Jennings et al. | |
| D667,838 S | 9/2012 | Magee et al. | |
| D675,164 S | 1/2013 | Kobayashi et al. | |
| D676,392 S | 2/2013 | Gassauer | |
| D678,196 S | 3/2013 | Miyauchi et al. | |
| D678,304 S | 3/2013 | Yakoub et al. | |
| 8,423,182 B2 | 4/2013 | Robinson et al. | |
| D687,146 S | 7/2013 | Juzkiw et al. | |
| 8,504,136 B1 | 8/2013 | Sun et al. | |
| 8,540,709 B2 | 9/2013 | Allen | |
| 8,551,088 B2 | 10/2013 | Falkenstein et al. | |
| 8,567,393 B2 | 10/2013 | Hickle et al. | |
| D704,839 S | 5/2014 | Juzkiw et al. | |
| 8,795,001 B1 | 8/2014 | Lam et al. | |
| 8,819,581 B2 | 8/2014 | Nakamura et al. | |
| 8,840,609 B2 | 9/2014 | Stuebe | |
| D716,333 S | 10/2014 | Chotin et al. | |
| 8,911,437 B2 | 12/2014 | Horlle et al. | |
| 8,917,513 B1 | 12/2014 | Hazzard | |
| 8,920,186 B2 | 12/2014 | Shishikura | |
| 8,923,012 B2 | 12/2014 | Kaufman et al. | |
| 8,961,441 B2 | 2/2015 | Cioanta et al. | |
| 8,968,296 B2 | 3/2015 | McPherson | |
| 8,986,288 B2 | 3/2015 | Konishi | |
| 9,017,326 B2 | 4/2015 | DiNardo et al. | |
| D729,267 S | 5/2015 | Yoo et al. | |
| 9,055,870 B2 | 6/2015 | Meador et al. | |
| 9,065,394 B2 | 6/2015 | Lim et al. | |
| 9,129,054 B2 | 9/2015 | Nawana et al. | |
| 9,160,853 B1 | 10/2015 | Daddi et al. | |
| 9,168,054 B2 | 10/2015 | Turner et al. | |
| 9,168,091 B2 | 10/2015 | Janssen et al. | |
| 9,198,711 B2 | 12/2015 | Joseph | |
| 9,226,766 B2 | 1/2016 | Aldridge et al. | |
| 9,226,791 B2 | 1/2016 | McCarthy et al. | |
| 9,237,921 B2 | 1/2016 | Messerly et al. | |
| 9,265,429 B2 | 2/2016 | St. Pierre et al. | |
| 9,277,961 B2 | 3/2016 | Panescu et al. | |
| 9,277,969 B2 | 3/2016 | Brannan et al. | |
| 9,281,615 B1 | 3/2016 | Plaza et al. | |
| 9,320,646 B2 | 4/2016 | Todd et al. | |
| 9,345,481 B2 | 5/2016 | Hall et al. | |
| 9,345,900 B2 | 5/2016 | Wu et al. | |
| 9,351,653 B1 | 5/2016 | Harrison | |
| 9,370,361 B2 | 6/2016 | Viola et al. | |
| 9,391,670 B2 | 7/2016 | Brukalo et al. | |
| 9,427,255 B2 | 8/2016 | Griffith et al. | |
| 9,430,438 B2 | 8/2016 | Biskup | |
| 9,463,646 B2 | 10/2016 | Payne et al. | |
| 9,474,565 B2 | 10/2016 | Shikhman et al. | |
| D772,252 S | 11/2016 | Myers et al. | |
| 9,486,271 B2 | 11/2016 | Dunning | |
| 9,491,895 B2 | 11/2016 | Steeves et al. | |
| 9,532,827 B2 | 1/2017 | Morgan et al. | |
| 9,589,720 B2 | 3/2017 | Akahane | |
| 9,600,031 B2 | 3/2017 | Kaneko et al. | |
| 9,603,277 B2 | 3/2017 | Morgan et al. | |
| D783,675 S | 4/2017 | Yagisawa et al. | |

(56) References Cited

U.S. PATENT DOCUMENTS

| | | |
|---|---|---|
| D784,270 S | 4/2017 | Bhattacharya |
| 9,666,974 B2 | 5/2017 | Bopp |
| 9,713,503 B2 | 7/2017 | Goldschmidt |
| 9,715,271 B2 | 7/2017 | Kaestner |
| 9,750,563 B2 | 9/2017 | Shikhman et al. |
| 9,770,103 B2 | 9/2017 | Cochran et al. |
| 9,773,093 B2 | 9/2017 | Bernini et al. |
| 9,782,214 B2 | 10/2017 | Houser et al. |
| 9,788,907 B1 | 10/2017 | Alvi et al. |
| 9,804,977 B2 | 10/2017 | Ghosh et al. |
| D806,721 S | 1/2018 | Fischer |
| 9,867,670 B2 | 1/2018 | Brannan et al. |
| 9,892,483 B2 | 2/2018 | Lee et al. |
| 9,892,564 B1 | 2/2018 | Cvetko et al. |
| 9,907,196 B2 | 2/2018 | Susini et al. |
| 9,971,395 B2 | 4/2018 | Chenault et al. |
| 9,974,595 B2 | 5/2018 | Anderson et al. |
| 9,987,068 B2 | 6/2018 | Anderson et al. |
| 9,987,072 B2 | 6/2018 | McPherson |
| 10,028,402 B1 | 7/2018 | Walker |
| 10,039,589 B2 | 8/2018 | Virshek et al. |
| D832,211 S | 10/2018 | Ladd et al. |
| 10,098,527 B2 | 10/2018 | Weisenburgh, II et al. |
| 10,105,470 B2 | 10/2018 | Reasoner et al. |
| 10,109,835 B2 | 10/2018 | Yang |
| D834,541 S | 11/2018 | You et al. |
| 10,117,702 B2 | 11/2018 | Danziger et al. |
| 10,128,612 B1 | 11/2018 | Casto |
| 10,136,954 B2 | 11/2018 | Johnson et al. |
| 10,137,245 B2 | 11/2018 | Melker et al. |
| 10,147,148 B2 | 12/2018 | Wu et al. |
| 10,166,061 B2 | 1/2019 | Berry et al. |
| 10,170,205 B2 | 1/2019 | Curd et al. |
| 10,201,365 B2 | 2/2019 | Boudreaux et al. |
| 10,339,496 B2 | 7/2019 | Matson et al. |
| 10,357,184 B2 | 7/2019 | Crawford et al. |
| 10,386,990 B2 | 8/2019 | Shikhman et al. |
| 10,441,345 B2 | 10/2019 | Aldridge et al. |
| 10,449,004 B2 | 10/2019 | Ferro et al. |
| 10,475,244 B2 | 11/2019 | Cvetko et al. |
| 10,493,287 B2 | 12/2019 | Yoder et al. |
| 10,499,847 B2 | 12/2019 | Latimer et al. |
| 10,499,996 B2 | 12/2019 | de Almeida Barreto |
| 10,523,122 B2 | 12/2019 | Han et al. |
| 10,531,579 B2 | 1/2020 | Hsiao et al. |
| D876,466 S | 2/2020 | Kobayashi et al. |
| 10,561,753 B2 | 2/2020 | Thompson et al. |
| 10,602,007 B2 | 3/2020 | Takano |
| 10,624,667 B2 | 4/2020 | Faller et al. |
| 10,624,691 B2 | 4/2020 | Wiener et al. |
| 10,675,027 B2 | 6/2020 | Aldridge et al. |
| 10,675,100 B2 | 6/2020 | Frushour |
| 10,687,884 B2 | 6/2020 | Wiener et al. |
| 10,729,502 B1 | 8/2020 | Wolf et al. |
| 10,743,872 B2 | 8/2020 | Leimbach et al. |
| 10,758,309 B1 | 9/2020 | Chow et al. |
| 10,758,310 B2 | 9/2020 | Shelton, IV et al. |
| 10,772,673 B2 | 9/2020 | Allen, IV et al. |
| 10,878,966 B2 | 12/2020 | Wolf et al. |
| 10,881,399 B2 | 1/2021 | Shelton, IV et al. |
| 10,898,256 B2 | 1/2021 | Yates et al. |
| 10,898,279 B2 | 1/2021 | Yang |
| 10,925,598 B2 | 2/2021 | Scheib et al. |
| 10,932,705 B2 | 3/2021 | Muhsin et al. |
| 10,932,772 B2 | 3/2021 | Shelton, IV et al. |
| 10,950,982 B2 | 3/2021 | Regnier et al. |
| 10,987,176 B2 | 4/2021 | Poltaretskyi et al. |
| 10,989,724 B1 | 4/2021 | Holmes et al. |
| 11,000,270 B2 | 5/2021 | Scheib et al. |
| D924,139 S | 7/2021 | Jayme |
| 11,056,244 B2 | 7/2021 | Shelton, IV et al. |
| 11,065,079 B2 | 7/2021 | Wolf et al. |
| 11,071,595 B2 | 7/2021 | Johnson et al. |
| D928,725 S | 8/2021 | Oberkircher et al. |
| D928,726 S | 8/2021 | Asher et al. |
| 11,077,312 B2 | 8/2021 | Sturman et al. |
| 11,083,489 B2 | 8/2021 | Fujii et al. |
| 11,116,587 B2 | 9/2021 | Wolf et al. |
| 11,185,379 B2 | 11/2021 | Shuma et al. |
| D939,545 S | 12/2021 | Oberkircher et al. |
| 11,259,793 B2 | 3/2022 | Scheib et al. |
| 11,259,875 B2 | 3/2022 | Boutin et al. |
| 11,272,839 B2 | 3/2022 | Al-Ali et al. |
| 11,284,963 B2 | 3/2022 | Shelton, IV et al. |
| 11,296,540 B2 | 4/2022 | Kirleis et al. |
| 11,304,763 B2 | 4/2022 | Shelton, IV et al. |
| 11,314,846 B1 | 4/2022 | Colin et al. |
| 11,369,366 B2 | 6/2022 | Scheib et al. |
| 11,382,699 B2 | 7/2022 | Wassall et al. |
| 11,382,700 B2 | 7/2022 | Calloway et al. |
| 11,419,604 B2 | 8/2022 | Scheib et al. |
| 11,424,027 B2 | 8/2022 | Shelton, IV |
| 11,432,877 B2 | 9/2022 | Nash et al. |
| 11,464,581 B2 | 10/2022 | Calloway |
| 11,478,820 B2 | 10/2022 | Bales, Jr. et al. |
| 11,504,192 B2 | 11/2022 | Shelton, IV et al. |
| 11,510,750 B2 | 11/2022 | Dulin et al. |
| 11,559,307 B2 | 1/2023 | Shelton, IV et al. |
| 11,564,678 B2 | 1/2023 | Scheib et al. |
| 11,571,205 B2 | 2/2023 | Scheib et al. |
| 11,576,677 B2 | 2/2023 | Shelton, IV et al. |
| 11,589,888 B2 | 2/2023 | Shelton, IV et al. |
| 11,659,023 B2 | 5/2023 | Shelton, IV et al. |
| 11,712,309 B2 | 8/2023 | Barak et al. |
| 2001/0029315 A1 | 10/2001 | Sakurai et al. |
| 2001/0031975 A1 | 10/2001 | Whitman et al. |
| 2002/0022836 A1 | 2/2002 | Goble et al. |
| 2002/0052563 A1 | 5/2002 | Penn et al. |
| 2002/0148942 A1* | 10/2002 | Payne ................. G02B 23/10 250/201.9 |
| 2002/0151770 A1 | 10/2002 | Noll et al. |
| 2002/0183734 A1 | 12/2002 | Bommannan et al. |
| 2003/0007321 A1 | 1/2003 | Dayley |
| 2003/0040670 A1 | 2/2003 | Govari |
| 2003/0050654 A1 | 3/2003 | Whitman et al. |
| 2003/0078631 A1 | 4/2003 | Nelson et al. |
| 2003/0093103 A1 | 5/2003 | Malackowski et al. |
| 2003/0114851 A1 | 6/2003 | Truckai et al. |
| 2003/0130677 A1 | 7/2003 | Whitman et al. |
| 2003/0199794 A1 | 10/2003 | Sakurai et al. |
| 2003/0199864 A1 | 10/2003 | Eick |
| 2004/0030328 A1 | 2/2004 | Eggers et al. |
| 2004/0059323 A1 | 3/2004 | Sturm et al. |
| 2004/0094597 A1 | 5/2004 | Whitman et al. |
| 2004/0111045 A1 | 6/2004 | Sullivan et al. |
| 2004/0111081 A1 | 6/2004 | Whitman et al. |
| 2004/0153724 A1 | 8/2004 | Nicholson et al. |
| 2004/0164983 A1 | 8/2004 | Khozai |
| 2005/0010209 A1 | 1/2005 | Lee et al. |
| 2005/0013459 A1 | 1/2005 | Maekawa |
| 2005/0021026 A1 | 1/2005 | Baily |
| 2005/0070800 A1 | 3/2005 | Takahashi |
| 2005/0113815 A1 | 5/2005 | Ritchie et al. |
| 2005/0113823 A1 | 5/2005 | Reschke et al. |
| 2005/0127868 A1 | 6/2005 | Calhoon et al. |
| 2005/0127869 A1 | 6/2005 | Calhoon et al. |
| 2005/0131390 A1 | 6/2005 | Heinrich et al. |
| 2005/0159778 A1 | 7/2005 | Heinrich et al. |
| 2005/0165390 A1 | 7/2005 | Mauti et al. |
| 2005/0173490 A1 | 8/2005 | Shelton |
| 2005/0229110 A1 | 10/2005 | Gegner et al. |
| 2005/0251233 A1 | 11/2005 | Kanzius |
| 2006/0020213 A1 | 1/2006 | Whitman et al. |
| 2006/0085049 A1 | 4/2006 | Cory et al. |
| 2006/0136622 A1 | 6/2006 | Rouvelin et al. |
| 2006/0149418 A1 | 7/2006 | Anvari |
| 2006/0212069 A1 | 9/2006 | Shelton |
| 2006/0256516 A1 | 11/2006 | Cho |
| 2006/0278680 A1 | 12/2006 | Viola et al. |
| 2006/0278681 A1 | 12/2006 | Viola et al. |
| 2006/0289600 A1 | 12/2006 | Wales et al. |
| 2007/0061393 A1 | 3/2007 | Moore |
| 2007/0076363 A1 | 4/2007 | Liang et al. |

(56) References Cited

U.S. PATENT DOCUMENTS

| | | | |
|---|---|---|---|
| 2007/0085602 A1* | 4/2007 | Park | H03F 1/0222 330/51 |
| 2007/0136218 A1 | 6/2007 | Bauer et al. | |
| 2007/0282321 A1 | 12/2007 | Shah et al. | |
| 2008/0072896 A1 | 3/2008 | Setzer et al. | |
| 2008/0090652 A1 | 4/2008 | Kuehling et al. | |
| 2008/0129465 A1 | 6/2008 | Rao | |
| 2008/0249377 A1 | 10/2008 | Molducci et al. | |
| 2008/0316304 A1 | 12/2008 | Claus et al. | |
| 2009/0036884 A1 | 2/2009 | Gregg et al. | |
| 2009/0054908 A1 | 2/2009 | Zand et al. | |
| 2009/0101692 A1 | 4/2009 | Whitman et al. | |
| 2009/0131929 A1 | 5/2009 | Shimizu | |
| 2009/0216091 A1 | 8/2009 | Arndt | |
| 2009/0228024 A1 | 9/2009 | Whitfield et al. | |
| 2009/0234352 A1 | 9/2009 | Behnke et al. | |
| 2009/0273353 A1 | 11/2009 | Kroh et al. | |
| 2010/0036405 A1 | 2/2010 | Giordano et al. | |
| 2010/0069939 A1 | 3/2010 | Konishi | |
| 2010/0076453 A1 | 3/2010 | Morris et al. | |
| 2010/0092006 A1 | 4/2010 | Rosen | |
| 2010/0120266 A1 | 5/2010 | Rimborg | |
| 2010/0198200 A1 | 8/2010 | Horvath | |
| 2010/0312239 A1 | 12/2010 | Sclig | |
| 2011/0015660 A1 | 1/2011 | Wiener et al. | |
| 2011/0092972 A1 | 4/2011 | Allen | |
| 2011/0093796 A1 | 4/2011 | Plummer et al. | |
| 2011/0106567 A1 | 5/2011 | Asher | |
| 2011/0125149 A1 | 5/2011 | El-Galley et al. | |
| 2011/0130689 A1 | 6/2011 | Cohen et al. | |
| 2011/0216920 A1* | 9/2011 | Yamamoto | H04R 3/007 381/120 |
| 2011/0238063 A1 | 9/2011 | Gregg | |
| 2011/0245630 A1 | 10/2011 | St. Pierre et al. | |
| 2011/0273465 A1 | 11/2011 | Konishi et al. | |
| 2011/0288451 A1 | 11/2011 | Sanai et al. | |
| 2011/0306840 A1 | 12/2011 | Allen et al. | |
| 2012/0029304 A1 | 2/2012 | Medina et al. | |
| 2012/0116380 A1 | 5/2012 | Madan et al. | |
| 2012/0132661 A1 | 5/2012 | Gu et al. | |
| 2012/0319890 A1 | 12/2012 | McCormack et al. | |
| 2013/0031201 A1 | 1/2013 | Kagan et al. | |
| 2013/0176220 A1 | 7/2013 | Merschon et al. | |
| 2013/0197503 A1 | 8/2013 | Orszulak | |
| 2013/0267975 A1 | 10/2013 | Timm et al. | |
| 2013/0268283 A1 | 10/2013 | Vann et al. | |
| 2014/0009894 A1 | 1/2014 | Yu | |
| 2014/0058714 A1 | 2/2014 | Boyer | |
| 2014/0087573 A1 | 3/2014 | Kroeckel | |
| 2014/0097903 A1 | 4/2014 | Aoki et al. | |
| 2014/0108048 A1 | 4/2014 | Cohn | |
| 2014/0111277 A1* | 4/2014 | Lim | H03F 1/0227 330/251 |
| 2014/0155721 A1 | 6/2014 | Hauck et al. | |
| 2014/0194683 A1 | 7/2014 | Nakaguchi | |
| 2014/0226572 A1 | 8/2014 | Thota et al. | |
| 2014/0262598 A1 | 9/2014 | Miki et al. | |
| 2014/0263552 A1 | 9/2014 | Hall et al. | |
| 2014/0378958 A1 | 12/2014 | Leussler | |
| 2015/0190189 A1 | 7/2015 | Yates et al. | |
| 2015/0272575 A1 | 10/2015 | Leimbach et al. | |
| 2015/0287367 A1* | 10/2015 | Van Lier | H03F 3/45076 330/252 |
| 2015/0289929 A1 | 10/2015 | Toth et al. | |
| 2015/0300923 A1 | 10/2015 | Halbert | |
| 2015/0334879 A1 | 11/2015 | Fricker | |
| 2015/0373115 A1 | 12/2015 | Breakstone et al. | |
| 2016/0000495 A1 | 1/2016 | Elliott et al. | |
| 2016/0045247 A1 | 2/2016 | Heim et al. | |
| 2016/0045365 A1 | 2/2016 | Foster et al. | |
| 2016/0058286 A1 | 3/2016 | Joshua et al. | |
| 2016/0062954 A1 | 3/2016 | Ruff et al. | |
| 2016/0074096 A1 | 3/2016 | Lieu | |
| 2016/0120591 A1 | 5/2016 | Smith et al. | |
| 2016/0164466 A1 | 6/2016 | Briffa et al. | |
| 2016/0199240 A1 | 7/2016 | Newkirk et al. | |
| 2016/0225192 A1 | 8/2016 | Jones et al. | |
| 2016/0249945 A1 | 9/2016 | Shelton, IV et al. | |
| 2016/0287312 A1 | 10/2016 | Tegg et al. | |
| 2016/0287337 A1 | 10/2016 | Aram et al. | |
| 2017/0000553 A1 | 1/2017 | Wiener et al. | |
| 2017/0007146 A1 | 1/2017 | Schulhauser et al. | |
| 2017/0024978 A1 | 1/2017 | Gulrez et al. | |
| 2017/0078455 A1 | 3/2017 | Fisher et al. | |
| 2017/0080346 A1 | 3/2017 | Abbas | |
| 2017/0090507 A1 | 3/2017 | Wiener et al. | |
| 2017/0151011 A1 | 6/2017 | Brustad et al. | |
| 2017/0189096 A1 | 7/2017 | Danziger et al. | |
| 2017/0202595 A1 | 7/2017 | Shelton, IV | |
| 2017/0209718 A1 | 7/2017 | Tanis | |
| 2017/0251305 A1 | 8/2017 | Fathollahi | |
| 2017/0252091 A1 | 9/2017 | Honda | |
| 2017/0296213 A1 | 10/2017 | Swensgard et al. | |
| 2017/0319259 A1 | 11/2017 | Dunning | |
| 2017/0360466 A1 | 12/2017 | Brown et al. | |
| 2018/0014872 A1 | 1/2018 | Dickerson | |
| 2018/0042659 A1 | 2/2018 | Rupp et al. | |
| 2018/0049795 A1 | 2/2018 | Swayze et al. | |
| 2018/0065248 A1 | 3/2018 | Barral et al. | |
| 2018/0078216 A1 | 3/2018 | Baker et al. | |
| 2018/0082480 A1 | 3/2018 | White et al. | |
| 2018/0099161 A1 | 4/2018 | Honda | |
| 2018/0166809 A1 | 6/2018 | Brogan et al. | |
| 2018/0206909 A1 | 7/2018 | Brustad et al. | |
| 2018/0221005 A1 | 8/2018 | Hamel et al. | |
| 2018/0228528 A1 | 8/2018 | Fraasch et al. | |
| 2018/0239856 A1 | 8/2018 | Takeuchi et al. | |
| 2018/0262916 A1 | 9/2018 | Polley et al. | |
| 2018/0263557 A1 | 9/2018 | Kahlman | |
| 2018/0296283 A1 | 10/2018 | Crawford et al. | |
| 2018/0333207 A1 | 11/2018 | Moctezuma De La Barrera | |
| 2018/0367870 A1 | 12/2018 | Shih | |
| 2019/0000478 A1 | 1/2019 | Messerly et al. | |
| 2019/0069957 A1 | 3/2019 | Barral et al. | |
| 2019/0125455 A1 | 5/2019 | Shelton, IV et al. | |
| 2019/0200844 A1 | 7/2019 | Shelton, IV et al. | |
| 2019/0200906 A1 | 7/2019 | Shelton, IV et al. | |
| 2019/0200981 A1 | 7/2019 | Harris et al. | |
| 2019/0201102 A1 | 7/2019 | Shelton, IV et al. | |
| 2019/0201140 A1 | 7/2019 | Yates et al. | |
| 2019/0201158 A1 | 7/2019 | Shelton, IV et al. | |
| 2019/0206563 A1 | 7/2019 | Shelton, IV et al. | |
| 2019/0224434 A1 | 7/2019 | Silver et al. | |
| 2019/0236840 A1 | 8/2019 | Zuckerman et al. | |
| 2019/0247141 A1 | 8/2019 | Batchelor et al. | |
| 2019/0247664 A1 | 8/2019 | Irazoqui et al. | |
| 2019/0269457 A1 | 9/2019 | Schofield et al. | |
| 2019/0278262 A1 | 9/2019 | Taylor et al. | |
| 2019/0279524 A1 | 9/2019 | Stoyanov et al. | |
| 2019/0348169 A1 | 11/2019 | Gibby et al. | |
| 2019/0371012 A1 | 12/2019 | Flexman et al. | |
| 2020/0004487 A1 | 1/2020 | Hanajima et al. | |
| 2020/0015899 A1 | 1/2020 | Scheib et al. | |
| 2020/0015900 A1 | 1/2020 | Scheib et al. | |
| 2020/0015907 A1 | 1/2020 | Scheib | |
| 2020/0015924 A1 | 1/2020 | Scheib et al. | |
| 2020/0030044 A1 | 1/2020 | Wang et al. | |
| 2020/0038120 A1 | 2/2020 | Ziraknejad et al. | |
| 2020/0078070 A1 | 3/2020 | Henderson et al. | |
| 2020/0078071 A1 | 3/2020 | Asher | |
| 2020/0078076 A1* | 3/2020 | Henderson | G16H 40/63 |
| 2020/0078077 A1 | 3/2020 | Henderson et al. | |
| 2020/0078078 A1 | 3/2020 | Henderson et al. | |
| 2020/0078079 A1 | 3/2020 | Morgan et al. | |
| 2020/0078080 A1 | 3/2020 | Henderson et al. | |
| 2020/0078081 A1 | 3/2020 | Jayme et al. | |
| 2020/0078082 A1 | 3/2020 | Henderson et al. | |
| 2020/0078083 A1 | 3/2020 | Sprinkle et al. | |
| 2020/0078089 A1 | 3/2020 | Henderson et al. | |
| 2020/0078106 A1 | 3/2020 | Henderson et al. | |
| 2020/0078110 A1 | 3/2020 | Henderson et al. | |
| 2020/0078111 A1 | 3/2020 | Oberkircher et al. | |
| 2020/0078112 A1 | 3/2020 | Henderson et al. | |
| 2020/0078113 A1 | 3/2020 | Sawhney et al. | |

(56) References Cited

U.S. PATENT DOCUMENTS

| | | |
|---|---|---|
| 2020/0078114 A1 | 3/2020 | Asher et al. |
| 2020/0078115 A1 | 3/2020 | Asher et al. |
| 2020/0078116 A1 | 3/2020 | Oberkircher et al. |
| 2020/0078117 A1 | 3/2020 | Henderson et al. |
| 2020/0078118 A1 | 3/2020 | Henderson et al. |
| 2020/0078119 A1 | 3/2020 | Henderson et al. |
| 2020/0078120 A1 | 3/2020 | Aldridge et al. |
| 2020/0081585 A1 | 3/2020 | Petre et al. |
| 2020/0090808 A1 | 3/2020 | Carroll et al. |
| 2020/0100825 A1 | 4/2020 | Henderson et al. |
| 2020/0100830 A1 | 4/2020 | Henderson et al. |
| 2020/0106220 A1 | 4/2020 | Henderson et al. |
| 2020/0129223 A1 | 4/2020 | Angeles et al. |
| 2020/0159313 A1 | 5/2020 | Gibby et al. |
| 2020/0237422 A1 | 7/2020 | Canady |
| 2020/0265398 A1 | 8/2020 | Lembo |
| 2020/0268472 A1 | 8/2020 | Wolf et al. |
| 2020/0305924 A1 | 10/2020 | Carroll |
| 2020/0305945 A1 | 10/2020 | Morgan et al. |
| 2020/0314569 A1 | 10/2020 | Morgan et al. |
| 2020/0342228 A1 | 10/2020 | Prevrhal et al. |
| 2020/0405375 A1 | 12/2020 | Shelton, IV et al. |
| 2021/0121246 A1 | 4/2021 | Gudalo |
| 2021/0169578 A1 | 6/2021 | Calloway et al. |
| 2021/0196383 A1 | 7/2021 | Shelton, IV et al. |
| 2021/0203889 A1 | 7/2021 | Fung et al. |
| 2021/0212717 A1 | 7/2021 | Yates et al. |
| 2021/0236755 A1 | 8/2021 | King et al. |
| 2021/0264680 A1 | 8/2021 | Cvetko et al. |
| 2021/0313938 A1 | 10/2021 | Tanaka et al. |
| 2021/0338343 A1 | 11/2021 | Swaffield et al. |
| 2021/0385889 A1 | 12/2021 | Patel |
| 2022/0032442 A1 | 2/2022 | Sheffield et al. |
| 2022/0104867 A1 | 4/2022 | Shelton, IV et al. |
| 2022/0104896 A1 | 4/2022 | Shelton, IV et al. |
| 2022/0104897 A1 | 4/2022 | Shelton, IV et al. |
| 2022/0104911 A1 | 4/2022 | Shelton, IV et al. |
| 2022/0151704 A1 | 5/2022 | Nikou |
| 2022/0155910 A1 | 5/2022 | Jeong |
| 2022/0261056 A1 | 8/2022 | Motoi et al. |
| 2022/0313338 A1 | 10/2022 | Carroll et al. |
| 2022/0313341 A1 | 10/2022 | Wiener et al. |
| 2022/0313342 A1 | 10/2022 | Leuck et al. |
| 2022/0313357 A1 | 10/2022 | Geresy et al. |
| 2022/0313369 A1 | 10/2022 | Oberkircher et al. |
| 2022/0313370 A1 | 10/2022 | Morgan et al. |
| 2022/0313371 A1 | 10/2022 | Morgan et al. |
| 2022/0313372 A1 | 10/2022 | Herman et al. |
| 2022/0313373 A1 | 10/2022 | Morgan et al. |
| 2022/0317750 A1 | 10/2022 | Jayme et al. |
| 2022/0318179 A1 | 10/2022 | Morgan et al. |
| 2022/0319685 A1 | 10/2022 | Vachon et al. |
| 2022/0319693 A1 | 10/2022 | Oberkircher et al. |
| 2022/0321059 A1 | 10/2022 | Samuel et al. |
| 2022/0322523 A1 | 10/2022 | Jayme et al. |
| 2022/0331013 A1 | 10/2022 | Shelton, IV et al. |
| 2022/0331047 A1 | 10/2022 | Shelton, IV et al. |
| 2022/0331048 A1 | 10/2022 | Shelton, IV et al. |
| 2022/0331049 A1 | 10/2022 | Shelton, IV et al. |
| 2022/0331050 A1 | 10/2022 | Shelton, IV et al. |
| 2022/0331051 A1 | 10/2022 | Shelton, IV et al. |
| 2022/0331052 A1 | 10/2022 | Shelton, IV et al. |
| 2022/0331053 A1 | 10/2022 | Kimball et al. |
| 2022/0331054 A1 | 10/2022 | Kimball et al. |
| 2022/0331056 A1 | 10/2022 | Shelton, IV et al. |
| 2022/0334787 A1 | 10/2022 | Jogan et al. |
| 2022/0335604 A1 | 10/2022 | Vanosdoll et al. |
| 2022/0335660 A1 | 10/2022 | Shelton, IV et al. |
| 2022/0335696 A1 | 10/2022 | Shelton, IV et al. |
| 2022/0336078 A1 | 10/2022 | Wise et al. |
| 2022/0336097 A1 | 10/2022 | Shelton, IV et al. |
| 2022/0337891 A1 | 10/2022 | Burnley et al. |
| 2022/0338049 A1 | 10/2022 | Ross et al. |
| 2023/0038130 A1 | 2/2023 | Cvetko et al. |
| 2023/0039037 A1 | 2/2023 | Henderson et al. |
| 2023/0069787 A1 | 3/2023 | Henderson et al. |
| 2023/0072423 A1 | 3/2023 | Osborn et al. |
| 2023/0346446 A1 | 11/2023 | Henderson et al. |

FOREIGN PATENT DOCUMENTS

| | | |
|---|---|---|
| EP | 0929263 B1 | 7/1999 |
| EP | 1006892 B1 | 6/2009 |
| EP | 2942023 A2 | 11/2015 |
| JP | S635457 A | 1/1988 |
| JP | H8280706 A | 10/1996 |
| JP | H1069453 A | 3/1998 |
| JP | 2000089850 A | 3/2000 |
| JP | 2001029353 A | 2/2001 |
| JP | 2001128993 A | 5/2001 |
| JP | 2002336194 A | 11/2002 |
| JP | 2006303167 A | 11/2006 |
| JP | 2007174666 A | 7/2007 |
| JP | 2009291308 A | 12/2009 |
| JP | 2010063883 A | 3/2010 |
| JP | 2014210052 A | 11/2014 |
| KR | 20110081018 A | 7/2011 |
| WO | WO-0112089 A1 | 2/2001 |
| WO | WO-2008053485 A1 | 5/2008 |
| WO | WO-2014031800 A1 | 2/2014 |
| WO | WO-2014071184 A1 | 5/2014 |
| WO | WO-2015047693 A1 | 4/2015 |
| WO | WO-2017058617 | 4/2017 |
| WO | WO-2018116247 A1 | 6/2018 |
| WO | WO-2019215354 A1 | 11/2019 |
| WO | WO-2021044136 A1 | 3/2021 |

OTHER PUBLICATIONS

Qian, et al., "A Review of Augmented Reality in Robotic-Assisted Surgery", IEEE Transactions On Medical Robotics and Bionics, IEEE, vol. 2, No. 1, pp. 1-16, Feb. 2020.

Yu et al., "Skin-Integrated Wireless Haptic Interfaces for Virtual and Augmented Reality," Nature, vol. 575, pp. 473-479, Nov. 21, 2019.

Li et al., "Wearable Energy Harvesters Generating Electricity From Low-Frequency Human Limb Movement," Microsystems & Nanoengineering (2018), vol. 4(24), 13 pages.

"Bowa Arc 400" Oct. 30, 2018, posted at bowa-medical.com, [site visited Aug. 6, 2021], https://www.bowa-medical.com/tradepro/shopru/artikel/allgemein/BOWA_BRO_11181_ARC400_V2.1_2018_10_30_EN.pdf (Year: 2018).

"Electrosurgical Generator ECONT-0201.3" Mar. 18, 2018, posted at contact-endoscopy.com, [site visited Aug. 6, 2021], https://contact-endoscopy.com/electrosurgical-system (Year: 2018).

Sorrells, P., "Application Note AN680. Passive RFID Basics," retrieved from http://ww1.microchip.com/downloads/en/AppNotes/00680b.pdf on Feb. 26, 2020, Dec. 31, 1998, pp. 1-7.

IEEE Std 802.Mar. 2012 (Revision of IEEE Std 802.3-2008, published Dec. 28, 2012.

"ATM-MPLS Network Interworking Version 2.0, af-aic-0178.001" ATM Standard, The ATM Forum Technical Committe, published Aug. 2003.

* cited by examiner

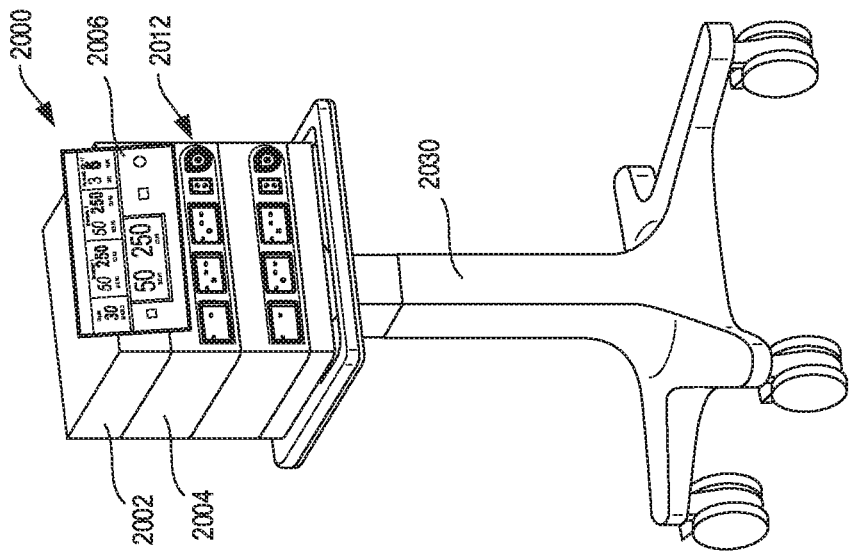
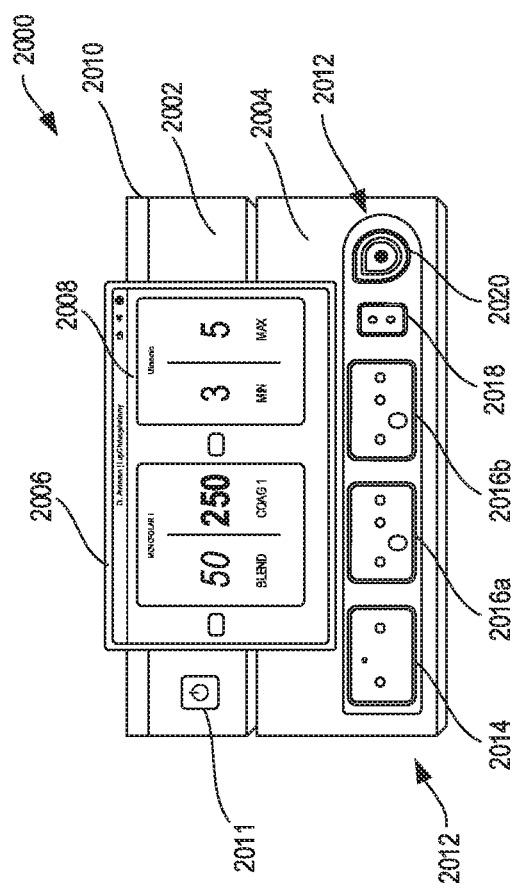
FIG. 7B
FIG. 7A

METHOD FOR ENERGY DELIVERY FOR MODULAR ENERGY SYSTEM

BACKGROUND

The present disclosure relates to various surgical systems, including modular electrosurgical and/or ultrasonic surgical systems. Operating rooms (ORs) are in need of streamlined capital solutions because ORs are a tangled web of cords, devices, and people due to the number of different devices that are needed to complete each surgical procedure. This is a reality of every OR in every market throughout the globe. Capital equipment is a major offender in creating clutter within ORs because most capital equipment performs one task or job, and each type of capital equipment requires unique techniques or methods to use and has a unique user interface. Accordingly, there are unmet consumer needs for capital equipment and other surgical technology to be consolidated in order to decrease the equipment footprint within the OR, streamline the equipment's interfaces, and improve surgical staff efficiency during a surgical procedure by reducing the number of devices that surgical staff members need to interact with.

In some surgical procedures, highly refined waveforms are delivered in a majority of surgery use cases and high power waveforms are delivered only in a minority of surgery use cases. Energy delivery is generally delivered at high efficiency as may be required by the thermal and power budget of the energy delivery system. High power and low efficiency can produce too much heat or exceed the limits of the energy delivery system. There is a benefit to delivering higher power using a higher efficiency power amplifier circuit. The lower efficiency power amplifier circuit has more control over wave shape.

Energy module components of modular energy systems are not capable of driving at least two bipolar RF instruments through one energy port non-simultaneously. There is a need during certain surgical procedure, however, to employ at least two bipolar RF instruments to complete an operation. Since energy modules have only a single RF bipolar output port into which an RF surgical instrument can be plugged into, a second energy module would be required to accommodate a second RF surgical instrument.

SUMMARY

In one aspect, the present disclosure provides a method of delivering power to a load coupled to an energy module. The method comprises determining, by a controller, a power to be produced in a load coupled to the controller; generating, by the controller, a signal; and selecting, by the controller, either a first power amplifier circuit or a second amplifier circuit based on the power to be produced in the load. A power rating of the first amplifier circuit is different from a power rating of the second amplifier circuit.

In another aspect, the present disclosure provides a method of delivering power to a load coupled to an energy module. The method comprises generating, by a controller, a digital waveform having a predetermined wave shape and frequency; converting, by a digital-to-analog converter (DAC) coupled to the controller, the digital waveform to an analog waveform; selecting, by the controller, a first power amplifier circuit or a second power amplifier circuit based on a predetermined power output to be produced by the first or second power amplifier circuit into a load coupled to an energy output port of the energy module; coupling, by the controller, the analog waveform to the selected first or second power amplifier circuit; and producing, by the selected first or second power amplifier circuit, the predetermined power output into the load coupled to the energy output port of the energy module.

In one aspect, the present disclosure provides an energy module. The energy module comprises a controller, a first power amplifier circuit having an input and an output. The input of the first power amplifier circuit is coupled to the controller and is configured to receive and amplify an input signal to generate a first output signal into a load coupled to the output of the first power amplifier circuit. The energy module further comprises and a second power amplifier circuit having an input and an output. The input of the second power amplifier circuit is coupled to the controller and is configured to receive and amplify the input signal to generate a second output into the load coupled the output of the second power amplifier circuit. A power rating of the first amplifier circuit is different from a power rating of the second amplifier circuit. The controller is configured to select the first or the second power amplifier circuit.

In another aspect, the present disclosure provides a method of delivering power to a load coupled to an energy module. The method comprises generating, by a controller, a digital waveform having a predetermined wave shape and frequency; converting, by a digital-to-analog converter (DAC) coupled to the controller, the digital waveform to an analog waveform; selecting, by the controller, a first power amplifier circuit or a second power amplifier circuit based on a predetermined power output to be produced by the first or second power amplifier circuit into a load coupled to an energy output port of the energy module; coupling, by the controller, the analog waveform to the selected first or second power amplifier circuit; and producing, by the selected first or second power amplifier circuit the predetermined power output into the load coupled to the energy output port of the energy module.

In another aspect, the present disclosure provides an energy module configured to deliver power to a load coupled thereto. The energy module comprises a digital-to-analog converter (DAC) configured to convert a digital waveform to an analog waveform and a controller coupled to the DAC. The controller is configured to generate the digital waveform having a predetermined wave shape and frequency; select a first power amplifier circuit or a second power amplifier circuit based on a predetermined power output to be produced by the first or second power amplifier circuit into a load coupled to an energy output port of the energy module; and couple the analog waveform to the selected first or second power amplifier circuit to produce, by the selected first or second power amplifier circuit the predetermined power output into the load coupled to the energy output port of the energy module.

In one aspect, the present disclosure provides a multi-energy port splitter for a modular energy system. The multi-energy port splitter comprises an input port configured to couple to an energy output port of an energy module; a first energy output port configured to deliver energy supplied by the energy output port of the energy module; at least a second energy output port configured to deliver the energy supplied by the energy output port of the energy module; an electronically controlled power switch configured to switch energy received at the input port to one of the first energy output port or the at least second energy output port; and a controller configured to couple to the energy module through a first communication bus, wherein the controller is electrically coupled to the electronically controlled power switch through a power switch control line.

In another aspect, the present disclosure provides a modular energy system. The modular energy system comprises a backplane comprising a plurality of backplane communication interfaces, wherein at least one of the plurality of communication interfaces is configured to receive at least one multi-energy port splitter and at least one other backplane communication interface is configured to receive an energy module; wherein the at least one multi-energy port splitter is presented as an energy delivery port to the energy module.

In yet another aspect, the present disclosure provides a modular energy system. The modular energy system comprises a header module; at least one energy module coupled to the header module, the energy module comprising an energy output port; and a multi-energy port splitter for a modular energy system, the multi-energy port splitter comprising: an input port coupled to the energy output port of the energy module; a first energy output port configured to deliver energy supplied by the energy output port of the energy module; at least a second energy output port configured to deliver the energy supplied by the energy output port of the energy module; an electronically controlled power switch configured to switch energy received at the input port to one of the first energy output port or the at least second energy output port; and a controller configured to couple to the energy module through a first communication bus, wherein the controller is electrically coupled to the electronically controlled power switch through a power switch control line.

FIGURES

The various aspects described herein, both as to organization and methods of operation, together with further objects and advantages thereof, may best be understood by reference to the following description, taken in conjunction with the accompanying drawings as follows.

FIG. 7A is a first illustrative modular energy system configuration including a header module and a display screen that renders a graphical user interface (GUI) for relaying information regarding modules connected to the header module, in accordance with at least one aspect of the present disclosure.

FIG. 7B is the modular energy system shown in FIG. 7A mounted to a cart, in accordance with at least one aspect of the present disclosure.

Corresponding reference characters indicate corresponding parts throughout the several views. The exemplifications set out herein illustrate various disclosed aspects, in one form, and such exemplifications are not to be construed as limiting the scope thereof in any manner.

DESCRIPTION

Figure 1:
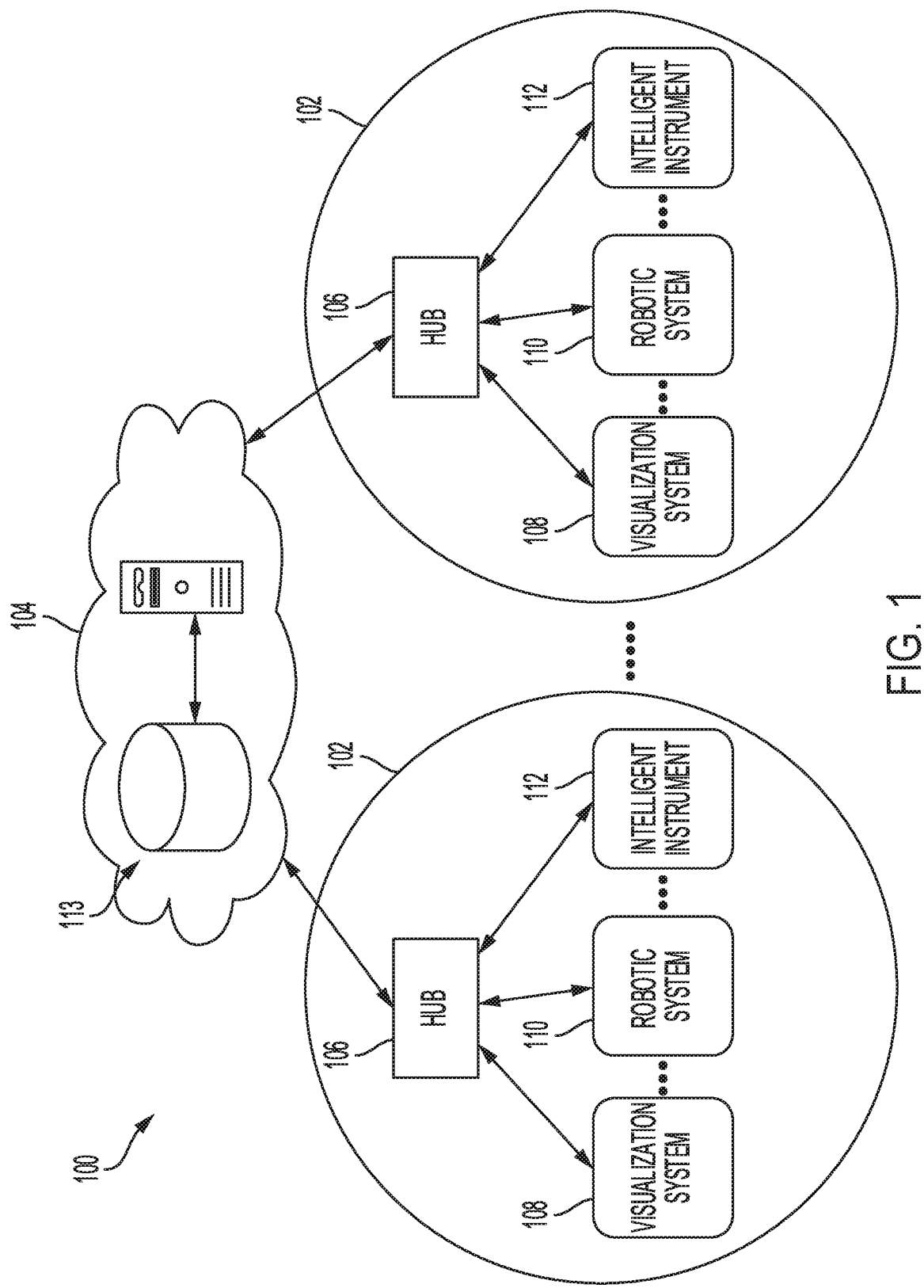
FIG. 1 is a block diagram of a computer-implemented interactive surgical system, in accordance with at least one aspect of the present disclosure.

Applicant of the present application owns the following U.S. Patent Applications filed Mar. 30, 2021, the disclosure of each of which is herein incorporated by reference in its entirety:

U.S. patent application Ser. No. 17/217,394, titled METHOD FOR MECHANICAL PACKAGING FOR MODULAR ENERGY SYSTEM, now U.S. Patent Application Publication No. 2022/0322523;

U.S. patent application Ser. No. 17/217,402, titled BACKPLANE CONNECTOR ATTACHMENT MECHANISM FOR MODULAR ENERGY SYSTEM, now U.S. Patent Application Publication No. 2022/0317750;

U.S. patent application Ser. No. 17/217,436, titled BEZEL WITH LIGHT BLOCKING FEATURES FOR MODULAR ENERGY SYSTEM, now U.S. Pat. No. 11,857,252;

U.S. patent application Ser. No. 17/217,446, titled HEADER FOR MODULAR ENERGY SYSTEM, now U.S. Patent Application Publication No. 2022/0313342;

U.S. patent application Ser. No. 17/217,403, titled SURGICAL PROCEDURALIZATION VIA MODULAR ENERGY SYSTEM, now U.S. Patent Application Publication No. 2022/0313341;

U.S. patent application Ser. No. 17/217,439, titled MODULAR ENERGY SYSTEM WITH DUAL AMPLIFIERS AND TECHNIQUES FOR UPDATING PARAMETERS THEREOF, now U.S. Patent Application Publication No. 2022/0321059;

U.S. patent application Ser. No. 17/217,471, titled MODULAR ENERGY SYSTEM WITH MULTI-ENERGY PORT SPLITTER FOR MULTIPLE ENERGY DEVICES, now U.S. Patent Application Publication No. 2022/0313373;

U.S. patent application Ser. No. 17/217,385, titled METHOD FOR INTELLIGENT INSTRUMENTS FOR MODULAR ENERGY SYSTEM, now U.S. Patent Application Publication No. 2022/0313369;

U.S. patent application Ser. No. 17/217,392, titled RADIO FREQUENCY IDENTIFICATION TOKEN FOR WIRELESS SURGICAL INSTRUMENTS, now U.S. Patent Application Publication No. 2022/0319693;

U.S. patent application Ser. No. 17/217,397, titled INTELLIGENT DATA PORTS FOR MODULAR ENERGY SYSTEMS, now U.S. Patent Application Publication No. 2022/0318179;

U.S. patent application Ser. No. 17/217,405, titled METHOD FOR SYSTEM ARCHITECTURE FOR MODULAR ENERGY SYSTEM, now U.S. Patent Application Publication No. 2022/0313370;

U.S. patent application Ser. No. 17/217,423, titled USER INTERFACE MITIGATION TECHNIQUES FOR MODULAR ENERGY SYSTEMS, now U.S. Patent Application Publication No. 2022/0313371;

U.S. patent application Ser. No. 17/217,429, titled ENERGY DELIVERY MITIGATIONS FOR MODULAR ENERGY SYSTEMS, now U.S. Patent Application Publication No. 2022/0313338;

U.S. patent application Ser. No. 17/217,449, titled ARCHITECTURE FOR MODULAR ENERGY SYSTEM, now U.S. Patent Application Publication No. 2022/0313372; and U.S. patent application Ser. No. 17/217,461, titled MODULAR ENERGY SYSTEM WITH HARDWARE MITIGATED COMMUNICATION, now U.S. Patent Application Publication No. 2022/0319685.

Applicant of the present application owns the following U.S. patent applications filed Sep. 5, 2019, the disclosure of each of which is herein incorporated by reference in its entirety:

U.S. patent application Ser. No. 16/562,144, titled METHOD FOR CONTROLLING A MODULAR ENERGY SYSTEM USER INTERFACE, now U.S. Patent Application Publication No. 2020/0078106;

U.S. patent application Ser. No. 16/562,151, titled PASSIVE HEADER MODULE FOR A MODULAR ENERGY SYSTEM, now U.S. Patent Application Publication No. 2020/0078110;

U.S. patent application Ser. No. 16/562,157, titled CONSOLIDATED USER INTERFACE FOR MODULAR ENERGY SYSTEM, now U.S. Patent Application Publication No. 2020/0081585;

U.S. patent application Ser. No. 16/562,159, titled AUDIO TONE CONSTRUCTION FOR AN ENERGY MODULE OF A MODULAR ENERGY SYSTEM, now U.S. Patent Application Publication No. 2020/0314569;

U.S. patent application Ser. No. 16/562,163, titled ADAPTABLY CONNECTABLE AND REASSIGNABLE SYSTEM ACCESSORIES FOR MODULAR ENERGY SYSTEM, now U.S. Patent Application Publication No. 2020/0078111;

U.S. patent application Ser. No. 16/562,123, titled METHOD FOR CONSTRUCTING AND USING A MODULAR SURGICAL ENERGY SYSTEM WITH MULTIPLE DEVICES, now U.S. Patent Application Publication No. 2020/0100830;

U.S. patent application Ser. No. 16/562,135, titled METHOD FOR CONTROLLING AN ENERGY MODULE OUTPUT, now U.S. Patent Application Publication No. 2020/0078076;

U.S. patent application Ser. No. 16/562,180, titled ENERGY MODULE FOR DRIVING MULTIPLE ENERGY MODALITIES, now U.S. Patent Application Publication No. 2020/0078080;

U.S. patent application Ser. No. 16/562,184, titled GROUNDING ARRANGEMENT OF ENERGY MODULES, now U.S. Patent Application Publication No. 2020/0078081;

U.S. patent application Ser. No. 16/562,188, titled BACKPLANE CONNECTOR DESIGN TO CONNECT STACKED ENERGY MODULES, now U.S. Patent Application Publication No. 2020/0078116;

U.S. patent application Ser. No. 16/562,195, titled ENERGY MODULE FOR DRIVING MULTIPLE ENERGY MODALITIES THROUGH A PORT, now U.S. Patent Application Publication No. 2020/0078117;

U.S. patent application Ser. No. 16/562,202 titled SURGICAL INSTRUMENT UTILIZING DRIVE SIGNAL TO POWER SECONDARY FUNCTION, now U.S. Patent Application Publication No. 2020/0078082;

U.S. patent application Ser. No. 16/562,142, titled METHOD FOR ENERGY DISTRIBUTION IN A SURGICAL MODULAR ENERGY SYSTEM, now U.S. Patent Application Publication No. 2020/0078070;

U.S. patent application Ser. No. 16/562,169, titled SURGICAL MODULAR ENERGY SYSTEM WITH A SEGMENTED BACKPLANE, now U.S. Patent Application Publication No. 2020/0078112;

U.S. patent application Ser. No. 16/562,185, titled SURGICAL MODULAR ENERGY SYSTEM WITH FOOTER MODULE, now U.S. Patent Application Publication No. 2020/0078115;

U.S. patent application Ser. No. 16/562,203, titled POWER AND COMMUNICATION MITIGATION ARRANGEMENT FOR MODULAR SURGICAL ENERGY SYSTEM, now U.S. Patent Application Publication No. 2020/0078118;

U.S. patent application Ser. No. 16/562,212, titled MODULAR SURGICAL ENERGY SYSTEM WITH MODULE POSITIONAL AWARENESS SENSING WITH VOLTAGE DETECTION, now U.S. Patent Application Publication No. 2020/0078119;

U.S. patent application Ser. No. 16/562,234, titled MODULAR SURGICAL ENERGY SYSTEM WITH MODULE POSITIONAL AWARENESS SENSING WITH TIME COUNTER, now U.S. Patent Application Publication No. 2020/0305945;

U.S. patent application Ser. No. 16/562,243, titled MODULAR SURGICAL ENERGY SYSTEM WITH MODULE POSITIONAL AWARENESS WITH DIGITAL LOGIC, now U.S. Patent Application Publication No. 2020/0078120;

U.S. patent application Ser. No. 16/562,125, titled METHOD FOR COMMUNICATING BETWEEN MODULES AND DEVICES IN A MODULAR SURGICAL SYSTEM, now U.S. Patent Application Publication No. 2020/0100825;

U.S. patent application Ser. No. 16/562,137, titled FLEXIBLE HAND-SWITCH CIRCUIT, now U.S. Patent Application Publication No. 2020/0106220;

U.S. patent application Ser. No. 16/562,143, titled FIRST AND SECOND COMMUNICATION PROTOCOL ARRANGEMENT FOR DRIVING PRIMARY AND SECONDARY DEVICES THROUGH A SINGLE PORT, now U.S. Patent Application Publication No. 2020/0090808;

U.S. patent application Ser. No. 16/562,148, titled FLEXIBLE NEUTRAL ELECTRODE, now U.S. Patent Application Publication No. 2020/0078077;

U.S. patent application Ser. No. 16/562,154, titled SMART RETURN PAD SENSING THROUGH MODULATION OF NEAR FIELD COMMUNICATION AND CONTACT QUALITY MONITORING SIGNALS, now U.S. Patent Application Publication No. 2020/0078089;

U.S. patent application Ser. No. 16/562,162, titled AUTOMATIC ULTRASONIC ENERGY ACTIVATION CIRCUIT DESIGN FOR MODULAR SURGICAL SYSTEMS, now U.S. Patent Application Publication No. 2020/0305924;

U.S. patent application Ser. No. 16/562,167, titled COORDINATED ENERGY OUTPUTS OF SEPARATE BUT CONNECTED MODULES, now U.S. Patent Application Publication No. 2020/0078078;

U.S. patent application Ser. No. 16/562,170, titled MANAGING SIMULTANEOUS MONOPOLAR OUTPUTS USING DUTY CYCLE AND SYNCHRONIZATION, now U.S. Patent Application Publication No. 2020/0078079;

U.S. patent application Ser. No. 16/562,172, titled PORT PRESENCE DETECTION SYSTEM FOR MODULAR ENERGY SYSTEM, now U.S. Patent Application Publication No. 2020/0078113;

U.S. patent application Ser. No. 16/562,175, titled INSTRUMENT TRACKING ARRANGEMENT BASED ON REAL TIME CLOCK INFORMATION, now U.S. Patent Application Publication No. 2020/0078071;

U.S. patent application Ser. No. 16/562,177, titled REGIONAL LOCATION TRACKING OF COMPONENTS OF A MODULAR ENERGY SYSTEM, now U.S. Patent Application Publication No. 2020/0078114;

U.S. Design patent application Ser. No. 29/704,610, titled ENERGY MODULE;

U.S. Design patent application Ser. No. 29/704,614, titled ENERGY MODULE MONOPOLAR PORT WITH FOURTH SOCKET AMONG THREE OTHER SOCKETS;

U.S. Design patent application Ser. No. 29/704,616, titled BACKPLANE CONNECTOR FOR ENERGY MODULE; and U.S. Design patent application Ser. No. 29/704,617, titled ALERT SCREEN FOR ENERGY MODULE.

Applicant of the present application owns the following U.S. Patent Provisional Applications filed Mar. 29, 2019, the disclosure of each of which is herein incorporated by reference in its entirety:

U.S. Provisional Patent Application Ser. No. 62/826,584, titled MODULAR SURGICAL PLATFORM ELECTRICAL ARCHITECTURE;

U.S. Provisional Patent Application Ser. No. 62/826,587, titled MODULAR ENERGY SYSTEM CONNECTIVITY;

U.S. Provisional Patent Application Ser. No. 62/826,588, titled MODULAR ENERGY SYSTEM INSTRUMENT COMMUNICATION TECHNIQUES; and U.S. Provisional Patent Application Ser. No. 62/826,592, titled MODULAR ENERGY DELIVERY SYSTEM Applicant of the present application owns the following U.S. Patent Provisional Application filed Sep. 7, 2018, the disclosure of which is herein incorporated by reference in its entirety:

U.S. Provisional Patent Application Ser. No. 62/728,480, titled MODULAR ENERGY SYSTEM AND USER INTERFACE.

Before explaining various aspects of surgical devices and generators in detail, it should be noted that the illustrative examples are not limited in application or use to the details of construction and arrangement of parts illustrated in the accompanying drawings and description. The illustrative examples may be implemented or incorporated in other aspects, variations and modifications, and may be practiced or carried out in various ways. Further, unless otherwise indicated, the terms and expressions employed herein have been chosen for the purpose of describing the illustrative examples for the convenience of the reader and are not for the purpose of limitation thereof. Also, it will be appreciated that one or more of the following-described aspects, expressions of aspects, and/or examples, can be combined with any one or more of the other following-described aspects, expressions of aspects and/or examples.

Various aspects are directed to improved ultrasonic surgical devices, electrosurgical devices and generators for use therewith. Aspects of the ultrasonic surgical devices can be configured for transecting and/or coagulating tissue during surgical procedures, for example. Aspects of the electrosurgical devices can be configured for transecting, coagulating, scaling, welding and/or desiccating tissue during surgical procedures, for example.

Surgical System Hardware

Referring to FIG. 1, a computer-implemented interactive surgical system 100 includes one or more surgical systems 102 and a cloud-based system (e.g., the cloud 104 that may include a remote server 113 coupled to a storage device 105). Each surgical system 102 includes at least one surgical hub 106 in communication with the cloud 104 that may include a remote server 113. In one example, as illustrated in FIG. 1, the surgical system 102 includes a visualization system 108, a robotic system 110, and a handheld intelligent surgical instrument 112, which are configured to communicate with one another and/or the hub 106. In some aspects, a surgical system 102 may include an M number of hubs 106, an N number of visualization systems 108, an O number of robotic systems 110, and a P number of handheld intelligent surgical instruments 112, where M, N, O, and P are integers greater than or equal to one.

Figure 2:
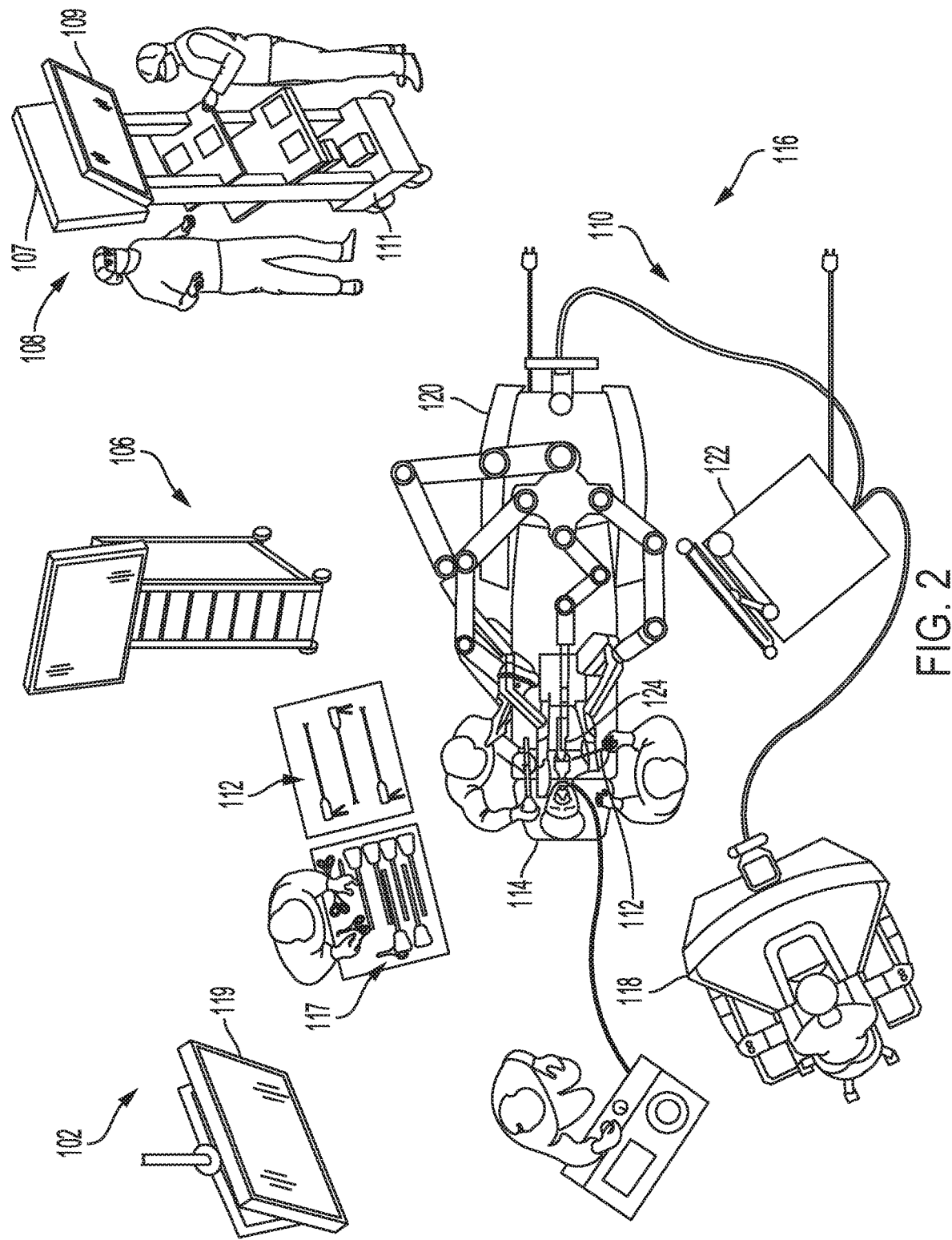
FIG. 2 is a surgical system being used to perform a surgical procedure in an operating room, in accordance with at least one aspect of the present disclosure.

FIG. 2 depicts an example of a surgical system 102 being used to perform a surgical procedure on a patient who is lying down on an operating table 114 in a surgical operating room 116. A robotic system 110 is used in the surgical procedure as a part of the surgical system 102. The robotic system 110 includes a surgeon's console 118, a patient side cart 120 (surgical robot), and a surgical robotic hub 122. The patient side cart 120 can manipulate at least one removably coupled surgical tool 117 through a minimally invasive incision in the body of the patient while the surgeon views the surgical site through the surgeon's console 118. An image of the surgical site can be obtained by a medical imaging device 124, which can be manipulated by the patient side cart 120 to orient the imaging device 124. The robotic hub 122 can be used to process the images of the surgical site for subsequent display to the surgeon through the surgeon's console 118.

Other types of robotic systems can be readily adapted for use with the surgical system 102. Various examples of robotic systems and surgical tools that are suitable for use with the present disclosure are described in U.S. Provisional Patent Application Ser. No. 62/611,339, titled ROBOT ASSISTED SURGICAL PLATFORM, filed Dec. 28, 2017, the disclosure of which is herein incorporated by reference in its entirety.

Various examples of cloud-based analytics that are performed by the cloud 104, and are suitable for use with the present disclosure, are described in U.S. Provisional Patent Application Ser. No. 62/611,340, titled CLOUD-BASED MEDICAL ANALYTICS, filed Dec. 28, 2017, the disclosure of which is herein incorporated by reference in its entirety.

In various aspects, the imaging device 124 includes at least one image sensor and one or more optical components. Suitable image sensors include, but are not limited to, Charge-Coupled Device (CCD) sensors and Complementary Metal-Oxide Semiconductor (CMOS) sensors.

The optical components of the imaging device 124 may include one or more illumination sources and/or one or more lenses. The one or more illumination sources may be directed to illuminate portions of the surgical field. The one or more image sensors may receive light reflected or refracted from the surgical field, including light reflected or refracted from tissue and/or surgical instruments.

The one or more illumination sources may be configured to radiate electromagnetic energy in the visible spectrum as well as the invisible spectrum. The visible spectrum, sometimes referred to as the optical spectrum or luminous spectrum, is that portion of the electromagnetic spectrum that is visible to (i.e., can be detected by) the human eye and may be referred to as visible light or simply light. A typical human eye will respond to wavelengths in air that are from about 380 nm to about 750 nm.

The invisible spectrum (i.e., the non-luminous spectrum) is that portion of the electromagnetic spectrum that lies below and above the visible spectrum (i.e., wavelengths below about 380 nm and above about 750 nm). The invisible spectrum is not detectable by the human eye. Wavelengths greater than about 750 nm are longer than the red visible spectrum, and they become invisible infrared (IR), microwave, and radio electromagnetic radiation. Wavelengths less than about 380 nm are shorter than the violet spectrum, and they become invisible ultraviolet, x-ray, and gamma ray electromagnetic radiation.

In various aspects, the imaging device 124 is configured for use in a minimally invasive procedure. Examples of imaging devices suitable for use with the present disclosure include, but are not limited to, an arthroscope, angioscope, bronchoscope, choledochoscope, colonoscope, cytoscope, duodenoscope, enteroscope, esophagogastro-duodenoscope (gastroscope), endoscope, laryngoscope, nasopharyngoneproscope, sigmoidoscope, thoracoscope, and ureteroscope.

In one aspect, the imaging device employs multi-spectrum monitoring to discriminate topography and underlying structures. A multi-spectral image is one that captures image data within specific wavelength ranges across the electromagnetic spectrum. The wavelengths may be separated by filters or by the use of instruments that are sensitive to particular wavelengths, including light from frequencies beyond the visible light range, e.g., IR and ultraviolet. Spectral imaging can allow extraction of additional information the human eye fails to capture with its receptors for red, green, and blue. The use of multi-spectral imaging is described in greater detail under the heading "Advanced Imaging Acquisition Module" in U.S. Provisional Patent Application Ser. No. 62/611,341, titled INTERACTIVE SURGICAL PLATFORM, filed Dec. 28, 2017, the disclosure of which is herein incorporated by reference in its entirety. Multi-spectrum monitoring can be a useful tool in relocating a surgical field after a surgical task is completed to perform one or more of the previously described tests on the treated tissue.

It is axiomatic that strict sterilization of the operating room and surgical equipment is required during any surgery. The strict hygiene and sterilization conditions required in a "surgical theater," i.e., an operating or treatment room, necessitate the highest possible sterility of all medical devices and equipment. Part of that sterilization process is the need to sterilize anything that comes in contact with the patient or penetrates the sterile field, including the imaging device 124 and its attachments and components. It will be appreciated that the sterile field may be considered a specified area, such as within a tray or on a sterile towel, that is considered free of microorganisms, or the sterile field may be considered an area, immediately around a patient, who has been prepared for a surgical procedure. The sterile field may include the scrubbed team members, who are properly attired, and all furniture and fixtures in the area.

In various aspects, the visualization system 108 includes one or more imaging sensors, one or more image-processing units, one or more storage arrays, and one or more displays that are strategically arranged with respect to the sterile field, as illustrated in FIG. 2. In one aspect, the visualization system 108 includes an interface for HL7, PACS, and EMR. Various components of the visualization system 108 are described under the heading "Advanced Imaging Acquisition Module" in U.S. Provisional Patent Application Ser. No. 62/611,341, titled INTERACTIVE SURGICAL PLATFORM, filed Dec. 28, 2017, the disclosure of which is herein incorporated by reference in its entirety.

As illustrated in FIG. 2, a primary display 119 is positioned in the sterile field to be visible to an operator at the operating table 114. In addition, a visualization tower 111 is positioned outside the sterile field. The visualization tower 111 includes a first non-sterile display 107 and a second non-sterile display 109, which face away from each other. The visualization system 108, guided by the hub 106, is configured to utilize the displays 107, 109, and 119 to coordinate information flow to operators inside and outside the sterile field. For example, the hub 106 may cause the visualization system 108 to display a snapshot of a surgical site, as recorded by an imaging device 124, on a non-sterile display 107 or 109, while maintaining a live feed of the surgical site on the primary display 119. The snapshot on the non-sterile display 107 or 109 can permit a non-sterile operator to perform a diagnostic step relevant to the surgical procedure, for example.

In one aspect, the hub 106 is also configured to route a diagnostic input or feedback entered by a non-sterile operator at the visualization tower 111 to the primary display 119 within the sterile field, where it can be viewed by a sterile operator at the operating table. In one example, the input can be in the form of a modification to the snapshot displayed on the non-sterile display 107 or 109, which can be routed to the primary display 119 by the hub 106.

Referring to FIG. 2, a surgical instrument 112 is being used in the surgical procedure as part of the surgical system 102. The hub 106 is also configured to coordinate information flow to a display of the surgical instrument 112. For example, in U.S. Provisional Patent Application Ser. No. 62/611,341, titled INTERACTIVE SURGICAL PLATFORM, filed Dec. 28, 2017, the disclosure of which is herein incorporated by reference in its entirety. A diagnostic input or feedback entered by a non-sterile operator at the visualization tower 111 can be routed by the hub 106 to the surgical instrument display 115 within the sterile field, where it can be viewed by the operator of the surgical instrument 112. Example surgical instruments that are suitable for use with the surgical system 102 are described under the heading SURGICAL INSTRUMENT HARDWARE and in U.S. Provisional Patent Application Ser. No. 62/611,341, titled INTERACTIVE SURGICAL PLATFORM, filed Dec. 28, 2017, the disclosure of which is herein incorporated by reference in its entirety, for example.

Figure 3:
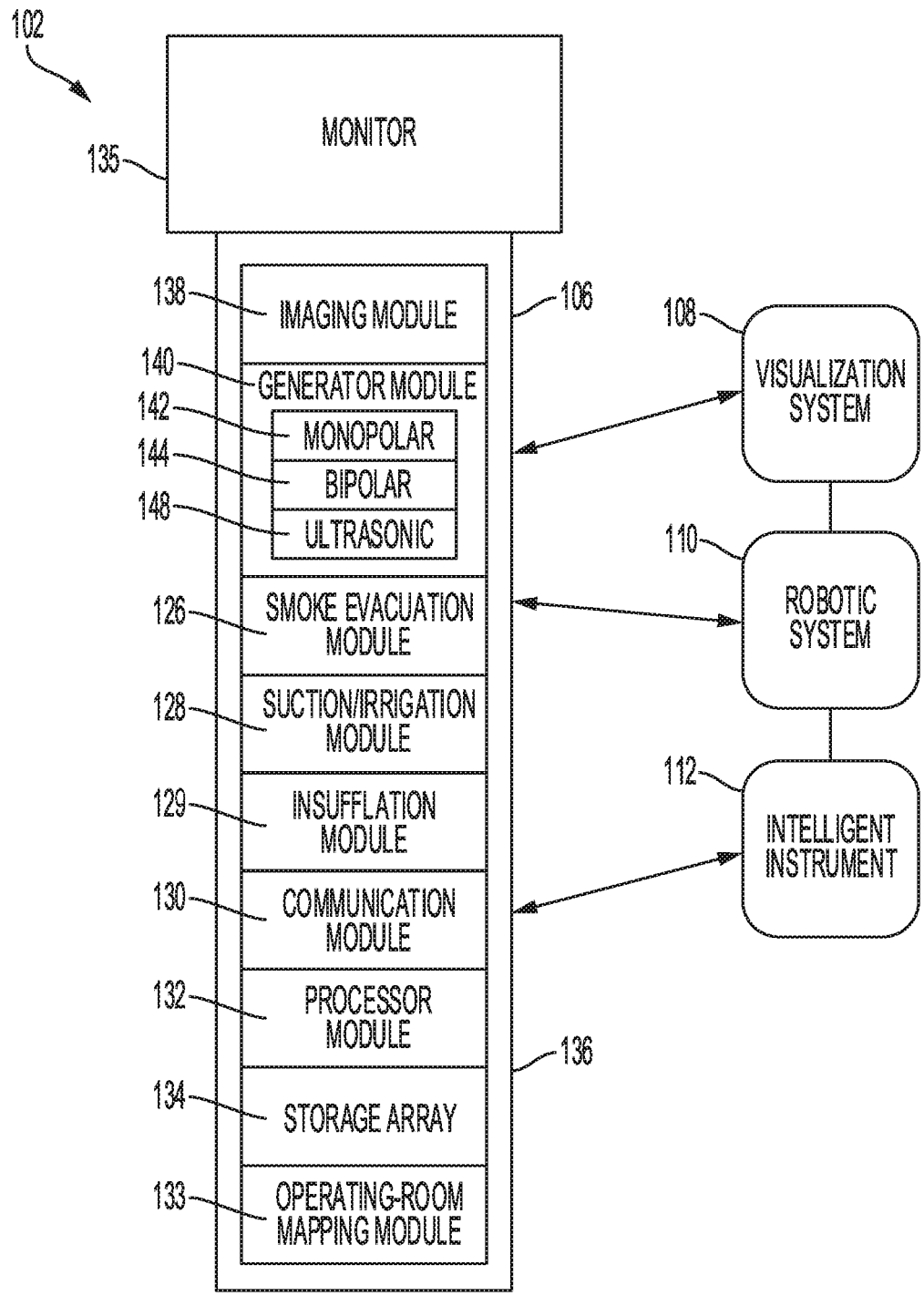
FIG. 3 is a surgical hub paired with a visualization system, a robotic system, and an intelligent instrument, in accordance with at least one aspect of the present disclosure.

Referring now to FIG. 3, a hub 106 is depicted in communication with a visualization system 108, a robotic system 110, and a handheld intelligent surgical instrument 112. In some aspects, the visualization system 108 may be a separable piece of equipment. In alternative aspects, the visualization system 108 could be contained within the hub 106 as a functional module. The hub 106 includes a hub display 135, an imaging module 138, a generator module 140, a communication module 130, a processor module 132, a storage array 134, and an operating room mapping module 133. In certain aspects, as illustrated in FIG. 3, the hub 106 further includes a smoke evacuation module 126, a suction/irrigation module 128, and/or an insufflation module 129. In certain aspects, any of the modules in the hub 106 may be combined with each other into a single module.

During a surgical procedure, energy application to tissue, for sealing and/or cutting, is generally associated with smoke evacuation, suction of excess fluid, and/or irrigation of the tissue. Fluid, power, and/or data lines from different sources are often entangled during the surgical procedure. Valuable time can be lost addressing this issue during a surgical procedure. Detangling the lines may necessitate disconnecting the lines from their respective modules, which may require resetting the modules. The hub modular enclosure 136 offers a unified environment for managing the power, data, and fluid lines, which reduces the frequency of entanglement between such lines.

Aspects of the present disclosure present a surgical hub for use in a surgical procedure that involves energy application to tissue at a surgical site. The surgical hub includes a hub enclosure and a combo generator module slidably receivable in a docking station of the hub enclosure. The docking station includes data and power contacts. The combo generator module includes one or more of an ultrasonic energy generator component, a bipolar RF energy generator component, and a monopolar RF energy generator component that are housed in a single unit. In one aspect, the combo generator module also includes a smoke evacuation component, at least one energy delivery cable for connecting the combo generator module to a surgical instrument, at least one smoke evacuation component configured to evacuate smoke, fluid, and/or particulates generated by the application of therapeutic energy to the tissue, and a fluid line extending from the remote surgical site to the smoke evacuation component.

In one aspect, the fluid line is a first fluid line and a second fluid line extends from the remote surgical site to a suction and irrigation module slidably received in the hub enclosure. In one aspect, the hub enclosure comprises a fluid interface.

Certain surgical procedures may require the application of more than one energy type to the tissue. One energy type may be more beneficial for cutting the tissue, while another different energy type may be more beneficial for sealing the tissue. For example, a bipolar generator can be used to seal the tissue while an ultrasonic generator can be used to cut the sealed tissue. Aspects of the present disclosure present a solution where a hub modular enclosure 136 is configured to accommodate different generators, and facilitate an interactive communication therebetween. One of the advantages of the hub modular enclosure 136 is enabling the quick removal and/or replacement of various modules.

Aspects of the present disclosure present a modular surgical enclosure for use in a surgical procedure that involves energy application to tissue. The modular surgical enclosure includes a first energy-generator module, configured to generate a first energy for application to the tissue, and a first docking station comprising a first docking port that includes first data and power contacts. In one aspect, the first energy-generator module is slidably movable into an electrical engagement with the power and data contacts and wherein the first energy-generator module is slidably movable out of the electrical engagement with the first power and data contacts. In an alternative aspect, the first energy-generator module is stackably movable into an electrical engagement with the power and data contacts and wherein the first energy-generator module is stackably movable out of the electrical engagement with the first power and data contacts.

Further to the above, the modular surgical enclosure also includes a second energy-generator module configured to generate a second energy, either the same or different than the first energy, for application to the tissue, and a second docking station comprising a second docking port that includes second data and power contacts. In one aspect, the second energy-generator module is slidably movable into an electrical engagement with the power and data contacts, and wherein the second energy-generator module is slidably movable out of the electrical engagement with the second power and data contacts. In an alternative aspect, the second energy-generator module is stackably movable into an electrical engagement with the power and data contacts, and wherein the second energy-generator module is stackably movable out of the electrical engagement with the second power and data contacts.

In addition, the modular surgical enclosure also includes a communication bus between the first docking port and the second docking port, configured to facilitate communication between the first energy-generator module and the second energy-generator module.

Referring to FIG. 3, aspects of the present disclosure are presented for a hub modular enclosure 136 that allows the modular integration of a generator module 140, a smoke evacuation module 126, a suction/irrigation module 128, and an insufflation module 129. The hub modular enclosure 136 further facilitates interactive communication between the modules 140, 126, 128, 129. The generator module 140 can be a generator module with integrated monopolar, bipolar, and ultrasonic components supported in a single housing unit slidably insertable into the hub modular enclosure 136.

The generator module 140 can be configured to connect to a monopolar device 142, a bipolar device 144, and an ultrasonic device 148. Alternatively, the generator module 140 may comprise a series of monopolar, bipolar, and/or ultrasonic generator modules that interact through the hub modular enclosure 136. The hub modular enclosure 136 can be configured to facilitate the insertion of multiple generators and interactive communication between the generators docked into the hub modular enclosure 136 so that the generators would act as a single generator.

In one aspect, the hub modular enclosure 136 comprises a modular power and communication backplane 149 with external and wireless communication headers to enable the removable attachment of the modules 140, 126, 128, 129 and interactive communication therebetween.

Generator Hardware

As used throughout this description, the term "wireless" and its derivatives may be used to describe circuits, devices, systems, methods, techniques, communications channels, etc., that may communicate data through the use of modulated electromagnetic radiation through a non-solid medium. The term does not imply that the associated devices do not contain any wires, although in some aspects they might not. The communication module may implement any of a number of wireless or wired communication standards or protocols, including but not limited to Wi-Fi (IEEE 802.11 family), WiMAX (IEEE 802.16 family), IEEE 802.20, long term evolution (LTE), Ev-DO, HSPA+, HSDPA+, HSUPA+, EDGE, GSM, GPRS, CDMA, TDMA, DECT, Bluetooth, Ethernet derivatives thereof, as well as any other wireless and wired protocols that are designated as 3G, 4G, 5G, and beyond. The computing module may include a plurality of communication modules. For instance, a first communication module may be dedicated to shorter range wireless communications such as Wi-Fi and Bluetooth and a second communication module may be dedicated to longer range wireless communications such as GPS, EDGE, GPRS, CDMA, WiMAX, LTE, Ev-DO, and others.

As used herein a processor or processing unit is an electronic circuit which performs operations on some external data source, usually memory or some other data stream. The term is used herein to refer to the central processor (central processing unit) in a system or computer systems (especially systems on a chip (SoCs)) that combine a number of specialized "processors."

As used herein, a system on a chip or system on chip (SoC or SOC) is an integrated circuit (also known as an "IC" or "chip") that integrates all components of a computer or other electronic systems. It may contain digital, analog, mixed-signal, and often radio-frequency functions—all on a single substrate. A SoC integrates a microcontroller (or microprocessor) with advanced peripherals like graphics processing unit (GPU), Wi-Fi module, or coprocessor. A SoC may or may not contain built-in memory.

As used herein, a microcontroller or controller is a system that integrates a microprocessor with peripheral circuits and memory. A microcontroller (or MCU for microcontroller unit) may be implemented as a small computer on a single integrated circuit. It may be similar to a SoC; a SoC may include a microcontroller as one of its components. A microcontroller may contain one or more core processing units (CPUs) along with memory and programmable input/output peripherals. Program memory in the form of Ferroelectric RAM, NOR flash or OTP ROM is also often included on chip, as well as a small amount of RAM.

Microcontrollers may be employed for embedded applications, in contrast to the microprocessors used in personal computers or other general purpose applications consisting of various discrete chips.

As used herein, the term controller or microcontroller may be a stand-alone IC or chip device that interfaces with a peripheral device. This may be a link between two parts of a computer or a controller on an external device that manages the operation of (and connection with) that device.

Any of the processors or microcontrollers described herein, may be implemented by any single core or multicore processor such as those known under the trade name ARM Cortex by Texas Instruments. In one aspect, the processor may be an LM4F230H5QR ARM Cortex-M4F Processor Core, available from Texas Instruments, for example, comprising on-chip memory of 256 KB single-cycle flash memory, or other non-volatile memory, up to 40 MHz, a prefetch buffer to improve performance above 40 MHz, a 32 KB single-cycle serial random access memory (SRAM), internal read-only memory (ROM) loaded with StellarisWare® software, 2 KB electrically erasable programmable read-only memory (EEPROM), one or more pulse width modulation (PWM) modules, one or more quadrature encoder inputs (QEI) analog, one or more 12-bit Analog-to-Digital Converters (ADC) with 12 analog input channels, details of which are available for the product datasheet.

In one aspect, the processor may comprise a safety controller comprising two controller-based families such as TMS570 and RM4x known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

Modular devices include the modules (as described in connection with FIG. 3, for example) that are receivable within a surgical hub and the surgical devices or instruments that can be connected to the various modules in order to connect or pair with the corresponding surgical hub. The modular devices include, for example, intelligent surgical instruments, medical imaging devices, suction/irrigation devices, smoke evacuators, energy generators, ventilators, insufflators, and displays. The modular devices described herein can be controlled by control algorithms. The control algorithms can be executed on the modular device itself, on the surgical hub to which the particular modular device is paired, or on both the modular device and the surgical hub (e.g., via a distributed computing architecture). In some exemplifications, the modular devices' control algorithms control the devices based on data sensed by the modular device itself (i.e., by sensors in, on, or connected to the modular device). This data can be related to the patient being operated on (e.g., tissue properties or insufflation pressure) or the modular device itself (e.g., the rate at which a knife is being advanced, motor current, or energy levels). For example, a control algorithm for a surgical stapling and cutting instrument can control the rate at which the instrument's motor drives its knife through tissue according to resistance encountered by the knife as it advances.

Figure 4:
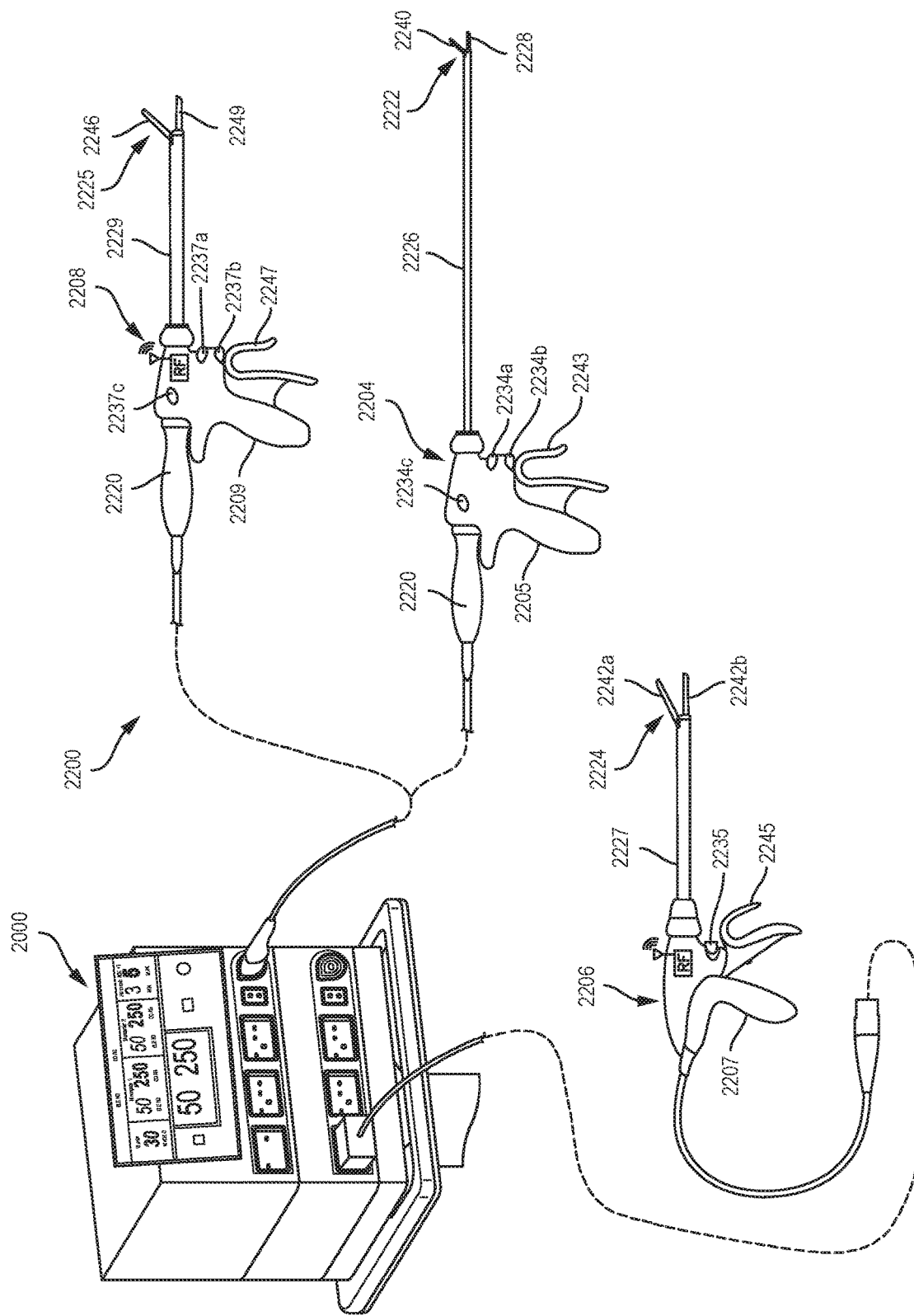
FIG. 4 is a surgical system comprising a generator and various surgical instruments usable therewith, in accordance with at least one aspect of the present disclosure.

FIG. 4 illustrates one form of a surgical system 2200 comprising a modular energy system 2000 and various surgical instruments 2204, 2206, 2208 usable therewith, where the surgical instrument 2204 is an ultrasonic surgical instrument, the surgical instrument 2206 is an RF electrosurgical instrument, and the multifunction surgical instrument 2208 is a combination ultrasonic/RF electrosurgical instrument. The modular energy system 2000 is configurable for use with a variety of surgical instruments. According to various forms, the modular energy system 2000 may be configurable for use with different surgical instruments of different types including, for example, ultrasonic surgical instruments 2204, RF electrosurgical instruments 2206, and multifunction surgical instruments 2208 that integrate RF and ultrasonic energies delivered individually or simultaneously from the modular energy system 2000. Although in the form of FIG. 4 the modular energy system 2000 is shown separate from the surgical instruments 2204, 2206, 2208 in one form, the modular energy system 2000 may be formed integrally with any of the surgical instruments 2204, 2206, 2208 to form a unitary surgical system. The modular energy system 2000 may be configured for wired or wireless communication.

The modular energy system 2000 is configured to drive multiple surgical instruments 2204, 2206, 2208. The first surgical instrument is an ultrasonic surgical instrument 2204 and comprises a handpiece 2205 (HP), an ultrasonic transducer 2220, a shaft 2226, and an end effector 2222. The end effector 2222 comprises an ultrasonic blade 2228 acoustically coupled to the ultrasonic transducer 2220 and a clamp arm 2240. The handpiece 2205 comprises a trigger 2243 to operate the clamp arm 2240 and a combination of the toggle buttons 2234a, 2234b, 2234c to energize and drive the ultrasonic blade 2228 or other function. The toggle buttons 2234a, 2234b, 2234c can be configured to energize the ultrasonic transducer 2220 with the modular energy system 2000.

The modular energy system 2000 also is configured to drive a second surgical instrument 2206. The second surgical instrument 2206 is an RF electrosurgical instrument and comprises a handpiece 2207 (HP), a shaft 2227, and an end effector 2224. The end effector 2224 comprises electrodes in clamp arms 2242a, 2242b and return through an electrical conductor portion of the shaft 2227. The electrodes are coupled to and energized by a bipolar energy source within the modular energy system 2000. The handpiece 2207 comprises a trigger 2245 to operate the clamp arms 2242a, 2242b and an energy button 2235 to actuate an energy switch to energize the electrodes in the end effector 2224.

The modular energy system 2000 also is configured to drive a multifunction surgical instrument 2208. The multifunction surgical instrument 2208 comprises a handpiece 2209 (HP), a shaft 2229, and an end effector 2225. The end effector 2225 comprises an ultrasonic blade 2249 and a clamp arm 2246. The ultrasonic blade 2249 is acoustically coupled to the ultrasonic transducer 2220. The ultrasonic transducer 2220 may be separable from or integral to the handpiece 2209. The handpiece 2209 comprises a trigger 2247 to operate the clamp arm 2246 and a combination of the toggle buttons 2237a, 2237b, 2237c to energize and drive the ultrasonic blade 2249 or other function. The toggle buttons 2237a, 2237b, 2237c can be configured to energize the ultrasonic transducer 2220 with the modular energy system 2000 and energize the ultrasonic blade 2249 with a bipolar energy source also contained within the modular energy system 2000.

The modular energy system 2000 is configurable for use with a variety of surgical instruments. According to various forms, the modular energy system 2000 may be configurable for use with different surgical instruments of different types including, for example, the ultrasonic surgical instrument 2204, the RF electrosurgical instrument 2206, and the multifunction surgical instrument 2208 that integrates RF and ultrasonic energies delivered individually or simultaneously from the modular energy system 2000. Although in the form of FIG. 4 the modular energy system 2000 is shown separate from the surgical instruments 2204, 2206, 2208, in another form the modular energy system 2000 may be formed integrally with any one of the surgical instruments 2204, 2206, 2208 to form a unitary surgical system. Further aspects of generators for digitally generating electrical signal waveforms and surgical instruments are described in U.S. Patent Application Publication No. 2017/0086914, which is herein incorporated by reference in its entirety.

Situational Awareness

Although an "intelligent" device including control algorithms that respond to sensed data can be an improvement over a "dumb" device that operates without accounting for sensed data, some sensed data can be incomplete or inconclusive when considered in isolation, i.e., without the context of the type of surgical procedure being performed or the type of tissue that is being operated on. Without knowing the procedural context (e.g., knowing the type of tissue being operated on or the type of procedure being performed), the control algorithm may control the modular device incorrectly or sub optimally given the particular context-free sensed data. For example, the optimal manner for a control algorithm to control a surgical instrument in response to a particular sensed parameter can vary according to the particular tissue type being operated on. This is due to the fact that different tissue types have different properties (e.g., resistance to tearing) and thus respond differently to actions taken by surgical instruments. Therefore, it may be desirable for a surgical instrument to take different actions even when the same measurement for a particular parameter is sensed. As one specific example, the optimal manner in which to control a surgical stapling and cutting instrument in response to the instrument sensing an unexpectedly high force to close its end effector will vary depending upon whether the tissue type is susceptible or resistant to tearing. For tissues that are susceptible to tearing, such as lung tissue, the instrument's control algorithm would optimally ramp down the motor in response to an unexpectedly high force to close to avoid tearing the tissue. For tissues that are resistant to tearing, such as stomach tissue, the instrument's control algorithm would optimally ramp up the motor in response to an unexpectedly high force to close to ensure that the end effector is clamped properly on the tissue. Without knowing whether lung or stomach tissue has been clamped, the control algorithm may make a suboptimal decision.

Figure 5:
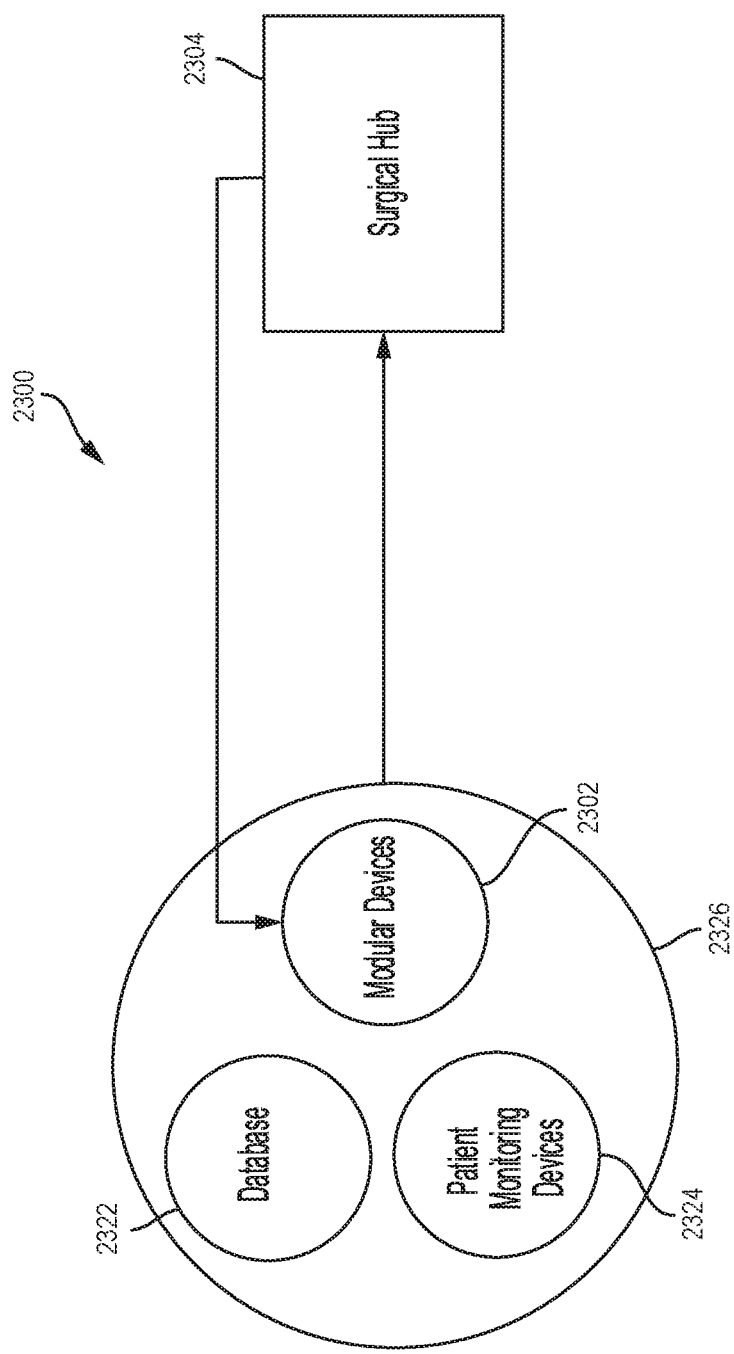
FIG. 5 is a diagram of a situationally aware surgical system, in accordance with at least one aspect of the present disclosure.

One solution utilizes a surgical hub including a system that is configured to derive information about the surgical procedure being performed based on data received from various data sources and then control the paired modular devices accordingly. In other words, the surgical hub is configured to infer information about the surgical procedure from received data and then control the modular devices paired to the surgical hub based upon the inferred context of the surgical procedure. FIG. 5 illustrates a diagram of a situationally aware surgical system 2300, in accordance with at least one aspect of the present disclosure. In some exemplifications, the data sources 2326 include, for example, the modular devices 2302 (which can include sensors configured to detect parameters associated with the patient and/or the modular device itself), databases 2322 (e.g., an EMR database containing patient records), and patient monitoring devices 2324 (e.g., a blood pressure (BP) monitor and an electrocardiography (EKG) monitor). The surgical hub 2304 can be configured to derive the contextual information pertaining to the surgical procedure from the data based upon, for example, the particular combination(s) of received data or the particular order in which the data is received from the data sources 2326. The contextual information inferred from the received data can include, for example, the type of surgical procedure being performed, the particular step of the surgical procedure that the surgeon is performing, the type of tissue being operated on, or the body cavity that is the subject of the procedure. This ability by some aspects of the surgical hub 2304 to derive or infer information related to the surgical procedure from received data can be referred to as "situational awareness." In one exemplification, the surgical hub 2304 can incorporate a situational awareness system, which is the hardware and/or programming associated with the surgical hub 2304 that derives contextual information pertaining to the surgical procedure from the received data.

The situational awareness system of the surgical hub 2304 can be configured to derive the contextual information from the data received from the data sources 2326 in a variety of different ways. In one exemplification, the situational awareness system includes a pattern recognition system, or machine learning system (e.g., an artificial neural network), that has been trained on training data to correlate various inputs (e.g., data from databases 2322, patient monitoring devices 2324, and/or modular devices 2302) to corresponding contextual information regarding a surgical procedure. In other words, a machine learning system can be trained to accurately derive contextual information regarding a surgical procedure from the provided inputs. In another exemplification, the situational awareness system can include a lookup table storing pre-characterized contextual information regarding a surgical procedure in association with one or more inputs (or ranges of inputs) corresponding to the contextual information. In response to a query with one or more inputs, the lookup table can return the corresponding contextual information for the situational awareness system for controlling the modular devices 2302. In one exemplification, the contextual information received by the situational awareness system of the surgical hub 2304 is associated with a particular control adjustment or set of control adjustments for one or more modular devices 2302. In another exemplification, the situational awareness system includes a further machine learning system, lookup table, or other such system, which generates or retrieves one or more control adjustments for one or more modular devices 2302 when provided the contextual information as input.

A surgical hub 2304 incorporating a situational awareness system provides a number of benefits for the surgical system 2300. One benefit includes improving the interpretation of sensed and collected data, which would in turn improve the processing accuracy and/or the usage of the data during the course of a surgical procedure. To return to a previous example, a situationally aware surgical hub 2304 could determine what type of tissue was being operated on; therefore, when an unexpectedly high force to close the surgical instrument's end effector is detected, the situationally aware surgical hub 2304 could correctly ramp up or ramp down the motor of the surgical instrument for the type of tissue.

As another example, the type of tissue being operated can affect the adjustments that are made to the compression rate and load thresholds of a surgical stapling and cutting instrument for a particular tissue gap measurement. A situationally aware surgical hub 2304 could infer whether a surgical procedure being performed is a thoracic or an abdominal procedure, allowing the surgical hub 2304 to determine whether the tissue clamped by an end effector of the surgical stapling and cutting instrument is lung (for a thoracic procedure) or stomach (for an abdominal procedure) tissue. The surgical hub 2304 could then adjust the compression rate and load thresholds of the surgical stapling and cutting instrument appropriately for the type of tissue.

As yet another example, the type of body cavity being operated in during an insufflation procedure can affect the function of a smoke evacuator. A situationally aware surgical hub 2304 could determine whether the surgical site is under pressure (by determining that the surgical procedure is utilizing insufflation) and determine the procedure type. As a procedure type is generally performed in a specific body cavity, the surgical hub 2304 could then control the motor rate of the smoke evacuator appropriately for the body cavity being operated in. Thus, a situationally aware surgical hub 2304 could provide a consistent amount of smoke evacuation for both thoracic and abdominal procedures.

As yet another example, the type of procedure being performed can affect the optimal energy level at which an ultrasonic surgical instrument or radio frequency (RF) electrosurgical instrument operates. Arthroscopic procedures, for example, require higher energy levels because the end effector of the ultrasonic surgical instrument or RF electrosurgical instrument is immersed in fluid. A situationally aware surgical hub 2304 could determine whether the surgical procedure is an arthroscopic procedure. The surgical hub 2304 could then adjust the RF power level or the ultrasonic amplitude of the generator (i.e., "energy level") to compensate for the fluid filled environment. Relatedly, the type of tissue being operated on can affect the optimal energy level for an ultrasonic surgical instrument or RF electrosurgical instrument to operate at. A situationally aware surgical hub 2304 could determine what type of surgical procedure is being performed and then customize the energy level for the ultrasonic surgical instrument or RF electrosurgical instrument, respectively, according to the expected tissue profile for the surgical procedure. Furthermore, a situationally aware surgical hub 2304 can be configured to adjust the energy level for the ultrasonic surgical instrument or RF electrosurgical instrument throughout the course of a surgical procedure, rather than just on a procedure-by-procedure basis. A situationally aware surgical hub 2304 could determine what step of the surgical procedure is being performed or will subsequently be performed and then update the control algorithms for the generator and/or ultrasonic surgical instrument or RF electrosurgical instrument to set the energy level at a value appropriate for the expected tissue type according to the surgical procedure step.

As yet another example, data can be drawn from additional data sources 2326 to improve the conclusions that the surgical hub 2304 draws from one data source 2326. A situationally aware surgical hub 2304 could augment data that it receives from the modular devices 2302 with contextual information that it has built up regarding the surgical procedure from other data sources 2326. For example, a situationally aware surgical hub 2304 can be configured to determine whether hemostasis has occurred (i.e., whether bleeding at a surgical site has stopped) according to video or image data received from a medical imaging device. However, in some cases the video or image data can be inconclusive. Therefore, in one exemplification, the surgical hub 2304 can be further configured to compare a physiologic measurement (e.g., blood pressure sensed by a BP monitor communicably connected to the surgical hub 2304) with the visual or image data of hemostasis (e.g., from a medical imaging device 124 (FIG. 2) communicably coupled to the surgical hub 2304) to make a determination on the integrity of the staple line or tissue weld. In other words, the situational awareness system of the surgical hub 2304 can consider the physiological measurement data to provide additional context in analyzing the visualization data. The additional context can be useful when the visualization data may be inconclusive or incomplete on its own.

Another benefit includes proactively and automatically controlling the paired modular devices 2302 according to the particular step of the surgical procedure that is being performed to reduce the number of times that medical personnel are required to interact with or control the surgical system 2300 during the course of a surgical procedure. For example, a situationally aware surgical hub 2304 could proactively activate the generator to which an RF electrosurgical instrument is connected if it determines that a subsequent step of the procedure requires the use of the instrument. Proactively activating the energy source allows the instrument to be ready for use a soon as the preceding step of the procedure is completed.

As another example, a situationally aware surgical hub 2304 could determine whether the current or subsequent step of the surgical procedure requires a different view or degree of magnification on the display according to the feature(s) at the surgical site that the surgeon is expected to need to view. The surgical hub 2304 could then proactively change the displayed view (supplied by, e.g., a medical imaging device for the visualization system 108) accordingly so that the display automatically adjusts throughout the surgical procedure.

As yet another example, a situationally aware surgical hub 2304 could determine which step of the surgical procedure is being performed or will subsequently be performed and whether particular data or comparisons between data will be required for that step of the surgical procedure. The surgical hub 2304 can be configured to automatically call up data screens based upon the step of the surgical procedure being performed, without waiting for the surgeon to ask for the particular information.

Another benefit includes checking for errors during the setup of the surgical procedure or during the course of the surgical procedure. For example, a situationally aware surgical hub 2304 could determine whether the operating theater is setup properly or optimally for the surgical procedure to be performed. The surgical hub 2304 can be configured to determine the type of surgical procedure being performed, retrieve the corresponding checklists, product location, or setup needs (e.g., from a memory), and then compare the current operating theater layout to the standard layout for the type of surgical procedure that the surgical hub 2304 determines is being performed. In one exemplification, the surgical hub 2304 can be configured to compare the list of items for the procedure (scanned by a scanner, for example) and/or a list of devices paired with the surgical hub 2304 to a recommended or anticipated manifest of items and/or devices for the given surgical procedure. If there are any discontinuities between the lists, the surgical hub 2304 can be configured to provide an alert indicating that a particular modular device 2302, patient monitoring device 2324, and/or other surgical item is missing. In one exemplification, the surgical hub 2304 can be configured to determine the relative distance or position of the modular devices 2302 and patient monitoring devices 2324 via proximity sensors, for example. The surgical hub 2304 can compare the relative positions of the devices to a recommended or anticipated layout for the particular surgical procedure. If there are any discontinuities between the layouts, the surgical hub 2304 can be configured to provide an alert indicating that the current layout for the surgical procedure deviates from the recommended layout.

As another example, a situationally aware surgical hub 2304 could determine whether the surgeon (or other medical personnel) was making an error or otherwise deviating from the expected course of action during the course of a surgical procedure. For example, the surgical hub 2304 can be configured to determine the type of surgical procedure being performed, retrieve the corresponding list of steps or order of equipment usage (e.g., from a memory), and then compare the steps being performed or the equipment being used during the course of the surgical procedure to the expected steps or equipment for the type of surgical procedure that the surgical hub 2304 determined is being performed. In one exemplification, the surgical hub 2304 can be configured to provide an alert indicating that an unexpected action is being performed or an unexpected device is being utilized at the particular step in the surgical procedure.

Overall, the situational awareness system for the surgical hub 2304 improves surgical procedure outcomes by adjusting the surgical instruments (and other modular devices 2302) for the particular context of each surgical procedure (such as adjusting to different tissue types) and validating actions during a surgical procedure. The situational awareness system also improves surgeons' efficiency in performing surgical procedures by automatically suggesting next steps, providing data, and adjusting displays and other modular devices 2302 in the surgical theater according to the specific context of the procedure.

Modular Energy System

ORs everywhere in the world are a tangled web of cords, devices, and people due to the amount of equipment required to perform surgical procedures. Surgical capital equipment tends to be a major contributor to this issue because most surgical capital equipment performs a single, specialized task. Due to their specialized nature and the surgeons' needs to utilize multiple different types of devices during the course of a single surgical procedure, an OR may be forced to be stocked with two or even more pieces of surgical capital equipment, such as energy generators. Each of these pieces of surgical capital equipment must be individually plugged into a power source and may be connected to one or more other devices that are being passed between OR personnel, creating a tangle of cords that must be navigated. Another issue faced in modern ORs is that each of these specialized pieces of surgical capital equipment has its own user interface and must be independently controlled from the other pieces of equipment within the OR. This creates complexity in properly controlling multiple different devices in connection with each other and forces users to be trained on and memorize different types of user interfaces (which may further change based upon the task or surgical procedure being performed, in addition to changing between each piece of capital equipment). This cumbersome, complex process can necessitate the need for even more individuals to be present within the OR and can create danger if multiple devices are not properly controlled in tandem with each other. Therefore, consolidating surgical capital equipment technology into singular systems that are able to flexibly address surgeons' needs to reduce the footprint of surgical capital equipment within ORs would simplify the user experience, reduce the amount of clutter in ORs, and prevent difficulties and dangers associated with simultaneously controlling multiple pieces of capital equipment. Further, making such systems expandable or customizable would allow for new technology to be conveniently incorporated into existing surgical systems, obviating the need to replace entire surgical systems or for OR personnel to learn new user interfaces or equipment controls with each new technology.

As described in FIGS. 1-3, a surgical hub 106 can be configured to interchangeably receive a variety of modules, which can in turn interface with surgical devices (e.g., a surgical instrument or a smoke evacuator) or provide various other functions (e.g., communications). In one aspect, a surgical hub 106 can be embodied as a modular energy system 2000, which is illustrated in connection with FIGS. 6-12. The modular energy system 2000 can include a variety of different modules 2001 that are connectable together in a stacked configuration. In one aspect, the modules 2001 can be both physically and communicably coupled together when stacked or otherwise connected together into a singular assembly. Further, the modules 2001 can be interchangeably connectable together in different combinations or arrangements. In one aspect, each of the modules 2001 can include a consistent or universal array of connectors disposed along their upper and lower surfaces, thereby allowing any module 2001 to be connected to another module 2001 in any arrangement (except that, in some aspects, a particular module type, such as the header module 2002, can be configured to serve as the uppermost module within the stack, for example). In an alternative aspect, the modular energy system 2000 can include a housing that is configured to receive and retain the modules 2001, as is shown in FIG. 3. The modular energy system 2000 can also include a variety of different components or accessories that are also connectable to or otherwise associatable with the modules 2001. In another aspect, the modular energy system 2000 can be embodied as a generator module 140 (FIG. 3) of a surgical hub 106. In yet another aspect, the modular energy system 2000 can be a distinct system from a surgical hub 106. In such aspects, the modular energy system 2000 can be communicably couplable to a surgical hub 206 for transmitting and/or receiving data therebetween.

Figure 6:
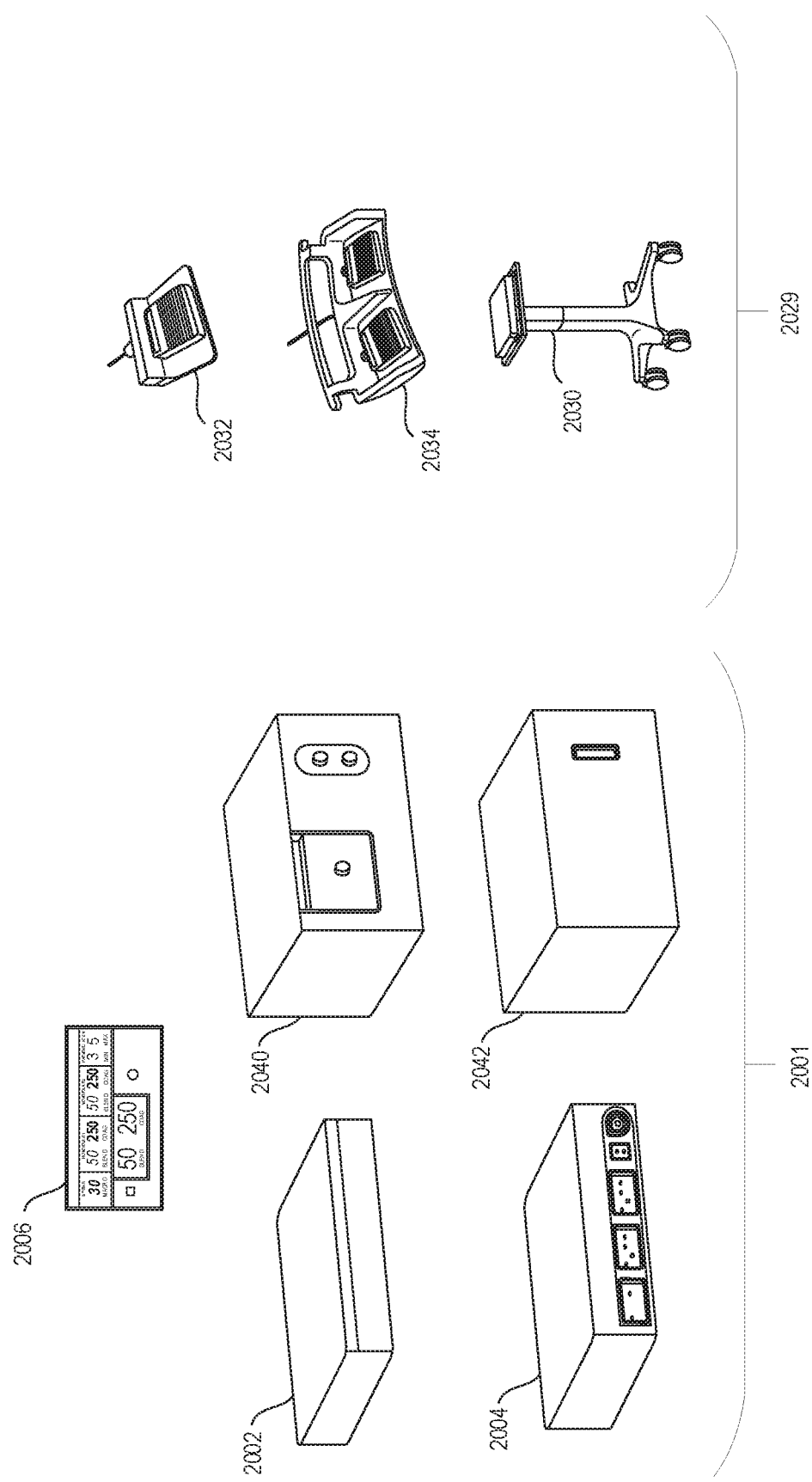
FIG. 6 is a diagram of various modules and other components that are combinable to customize modular energy systems, in accordance with at least one aspect of the present disclosure.

The modular energy system 2000 can be assembled from a variety of different modules 2001, some examples of which are illustrated in FIG. 6. Each of the different types of modules 2001 can provide different functionality, thereby allowing the modular energy system 2000 to be assembled into different configurations to customize the functions and capabilities of the modular energy system 2000 by customizing the modules 2001 that are included in each modular energy system 2000. The modules 2001 of the modular energy system 2000 can include, for example, a header module 2002 (which can include a display screen 2006), an energy module 2004, a technology module 2040, and a visualization module 2042. In the depicted aspect, the header module 2002 is configured to serve as the top or uppermost module within the modular energy system stack and can thus lack connectors along its top surface. In another aspect, the header module 2002 can be configured to be positioned at the bottom or the lowermost module within the modular energy system stack and can thus lack connectors along its bottom surface. In yet another aspect, the header module 2002 can be configured to be positioned at an intermediate position within the modular energy system stack and can thus include connectors along both its bottom and top surfaces. The header module 2002 can be configured to control the system-wide settings of each module 2001 and component connected thereto through physical controls 2011 thereon and/or a graphical user interface (GUI) 2008 rendered on the display screen 2006. Such settings could include the activation of the modular energy system 2000, the volume of alerts, the footswitch settings, the settings icons, the appearance or configuration of the user interface, the surgeon profile logged into the modular energy system 2000, and/or the type of surgical procedure being performed. The header module 2002 can also be configured to provide communications, processing, and/or power for the modules 2001 that are connected to the header module 2002. The energy module 2004, which can also be referred to as a generator module 140 (FIG. 3), can be configured to generate one or multiple energy modalities for driving electrosurgical and/or ultrasonic surgical instruments connected thereto. The technology module 2040 can be configured to provide additional or expanded control algorithms (e.g., electrosurgical or ultrasonic control algorithms for controlling the energy output of the energy module 2004). The visualization module 2042 can be configured to interface with visualization devices (i.e., scopes) and accordingly provide increased visualization capabilities.

The modular energy system 2000 can further include a variety of accessories 2029 that are connectable to the modules 2001 for controlling the functions thereof or that are otherwise configured to work on conjunction with the modular energy system 2000. The accessories 2029 can include, for example, a single-pedal footswitch 2032, a dual-pedal footswitch 2034, and a cart 2030 for supporting the modular energy system 2000 thereon. The footswitches 2032, 2034 can be configured to control the activation or function of particular energy modalities output by the energy module 2004, for example.

By utilizing modular components, the depicted modular energy system 2000 provides a surgical platform that grows with the availability of technology and is customizable to the needs of the facility and/or surgeons. Further, the modular energy system 2000 supports combo devices (e.g., dual electrosurgical and ultrasonic energy generators) and supports software-driven algorithms for customized tissue effects. Still further, the surgical system architecture reduces the capital footprint by combining multiple technologies critical for surgery into a single system.

The various modular components utilizable in connection with the modular energy system 2000 can include monopolar energy generators, bipolar energy generators, dual electrosurgical/ultrasonic energy generators, display screens, and various other modules and/or other components, some of which are also described above in connection with FIGS. 1-3.

Referring now to FIG. 7A, the header module 2002 can, in some aspects, include a display screen 2006 that renders a GUI 2008 for relaying information regarding the modules 2001 connected to the header module 2002. In some aspects, the GUI 2008 of the display screen 2006 can provide a consolidated point of control of all of the modules 2001 making up the particular configuration of the modular energy system 2000. Various aspects of the GUI 2008 are discussed in fuller detail below in connection with FIG. 12. In alternative aspects, the header module 2002 can lack the display screen 2006 or the display screen 2006 can be detachably connected to the housing 2010 of the header module 2002. In such aspects, the header module 2002 can be communicably couplable to an external system that is configured to display the information generated by the modules 2001 of the modular energy system 2000. For example, in robotic surgical applications, the modular energy system 2000 can be communicably couplable to a robotic cart or robotic control console, which is configured to display the information generated by the modular energy system 2000 to the operator of the robotic surgical system.

Figure 11:
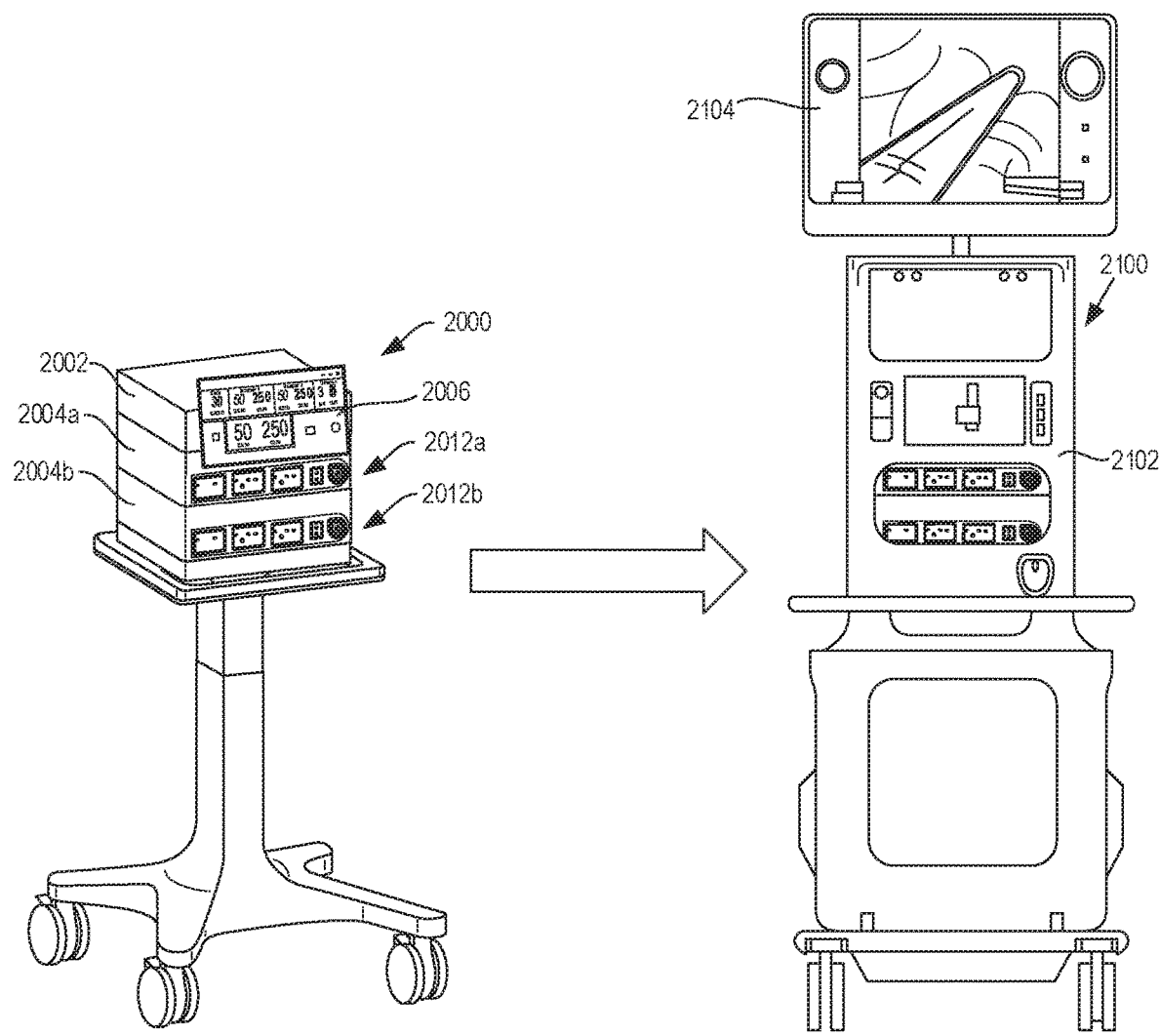
FIG. 11 is a diagram of a modular energy system including communicably connectable surgical platforms, in accordance with at least one aspect of the present disclosure.

As another example, the modular energy system 2000 can be communicably couplable to a mobile display that can be carried or secured to a surgical staff member for viewing thereby. In yet another example, the modular energy system 2000 can be communicably couplable to a surgical hub 2100 or another computer system that can include a display 2104, as is illustrated in FIG. 11. In aspects utilizing a user interface that is separate from or otherwise distinct from the modular energy system 2000, the user interface can be wirelessly connectable with the modular energy system 2000 as a whole or one or more modules 2001 thereof such that the user interface can display information from the connected modules 2001 thereon.

Referring still to FIG. 7A, the energy module 2004 can include a port assembly 2012 including a number of different ports configured to deliver different energy modalities to corresponding surgical instruments that are connectable thereto. In the particular aspect illustrated in FIGS. 6-12, the port assembly 2012 includes a bipolar port 2014, a first monopolar port 2016a, a second monopolar port 2016b, a neutral electrode port 2018 (to which a monopolar return pad is connectable), and a combination energy port 2020. However, this particular combination of ports is simply provided for illustrative purposes and alternative combinations of ports and/or energy modalities may be possible for the port assembly 2012.

As noted above, the modular energy system 2000 can be assembled into different configurations. Further, the different configurations of the modular energy system 2000 can also be utilizable for different surgical procedure types and/or different tasks. For example, FIGS. 7A and 7B illustrate a first illustrative configuration of the modular energy system 2000 including a header module 2002 (including a display screen 2006) and an energy module 2004 connected together. Such a configuration can be suitable for laparoscopic and open surgical procedures, for example.

Figure 8A:
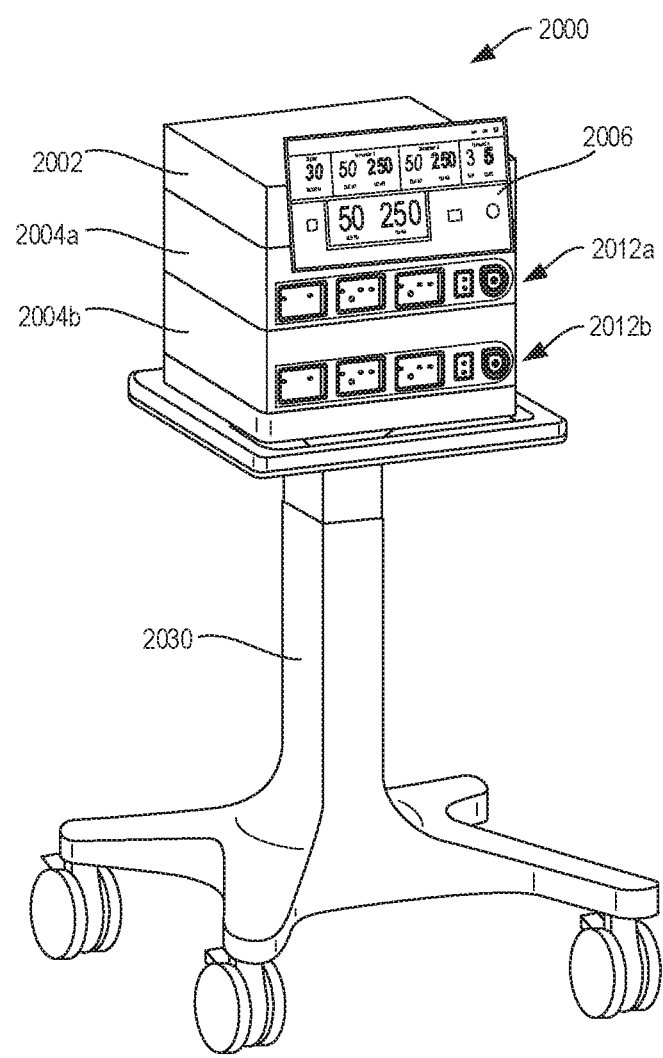
FIG. 8A is a second illustrative modular energy system configuration including a header module, a display screen, an energy module, and an expanded energy module connected together and mounted to a cart, in accordance with at least one aspect of the present disclosure.
Figure 8B:
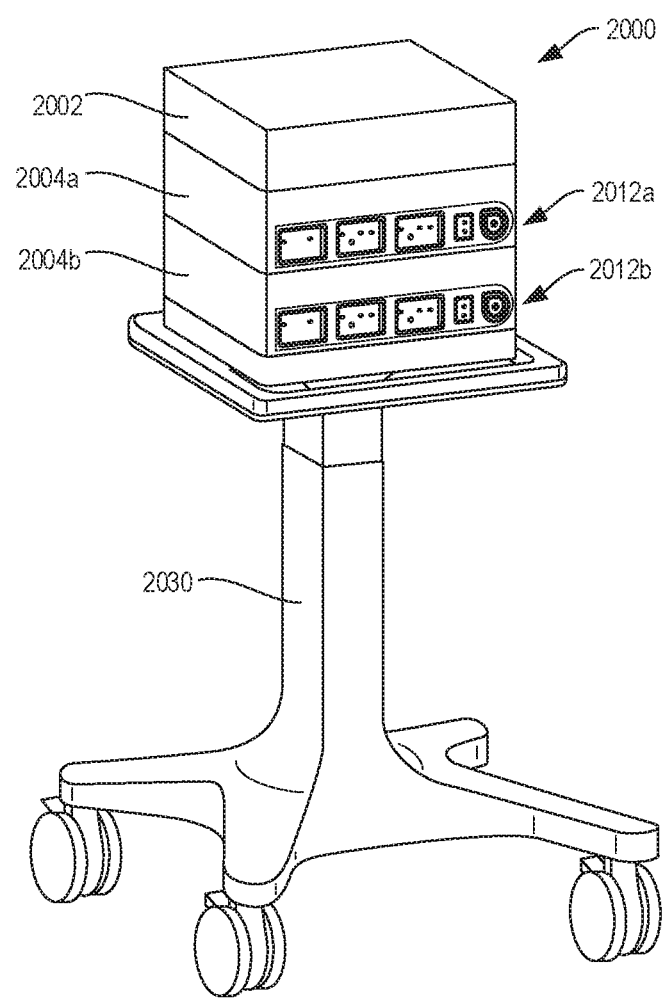
FIG. 8B is a third illustrative modular energy system configuration that is similar to the second configuration shown in FIG. 7A, except that the header module lacks a display screen, in accordance with at least one aspect of the present disclosure.

FIG. 8A illustrates a second illustrative configuration of the modular energy system 2000 including a header module 2002 (including a display screen 2006), a first energy module 2004a, and a second energy module 2004b connected together. By stacking two energy modules 2004a, 2004b, the modular energy system 2000 can provide a pair of port assemblies 2012a, 2012b for expanding the array of energy modalities deliverable by the modular energy system 2000 from the first configuration. The second configuration of the modular energy system 2000 can accordingly accommodate more than one bipolar/monopolar electrosurgical instrument, more than two bipolar/monopolar electrosurgical instruments, and so on. Such a configuration can be suitable for particularly complex laparoscopic and open surgical procedures. FIG. 8B illustrates a third illustrative configuration that is similar to the second configuration, except that the header module 2002 lacks a display screen 2006. This configuration can be suitable for robotic surgical applications or mobile display applications, as noted above.

Figure 9:
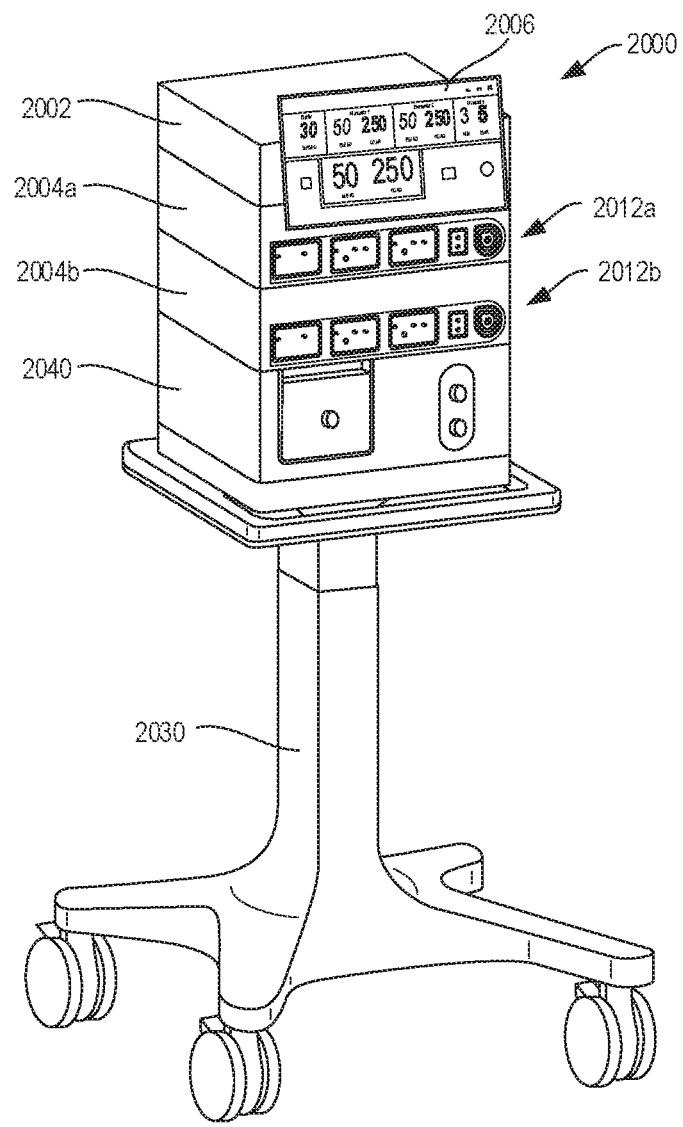
FIG. 9 is a fourth illustrative modular energy system configuration including a header module, a display screen, an energy module, ae expanded energy module, and a technology module connected together and mounted to a cart, in accordance with at least one aspect of the present disclosure.

FIG. 9 illustrates a fourth illustrative configuration of the modular energy system 2000 including a header module 2002 (including a display screen 2006), a first energy module 2004a, a second energy module 2004b, and a technology module 2040 connected together. Such a configuration can be suitable for surgical applications where particularly complex or computation-intensive control algorithms are required. Alternatively, the technology module 2040 can be a newly released module that supplements or expands the capabilities of previously released modules (such as the energy module 2004).

Figure 10:
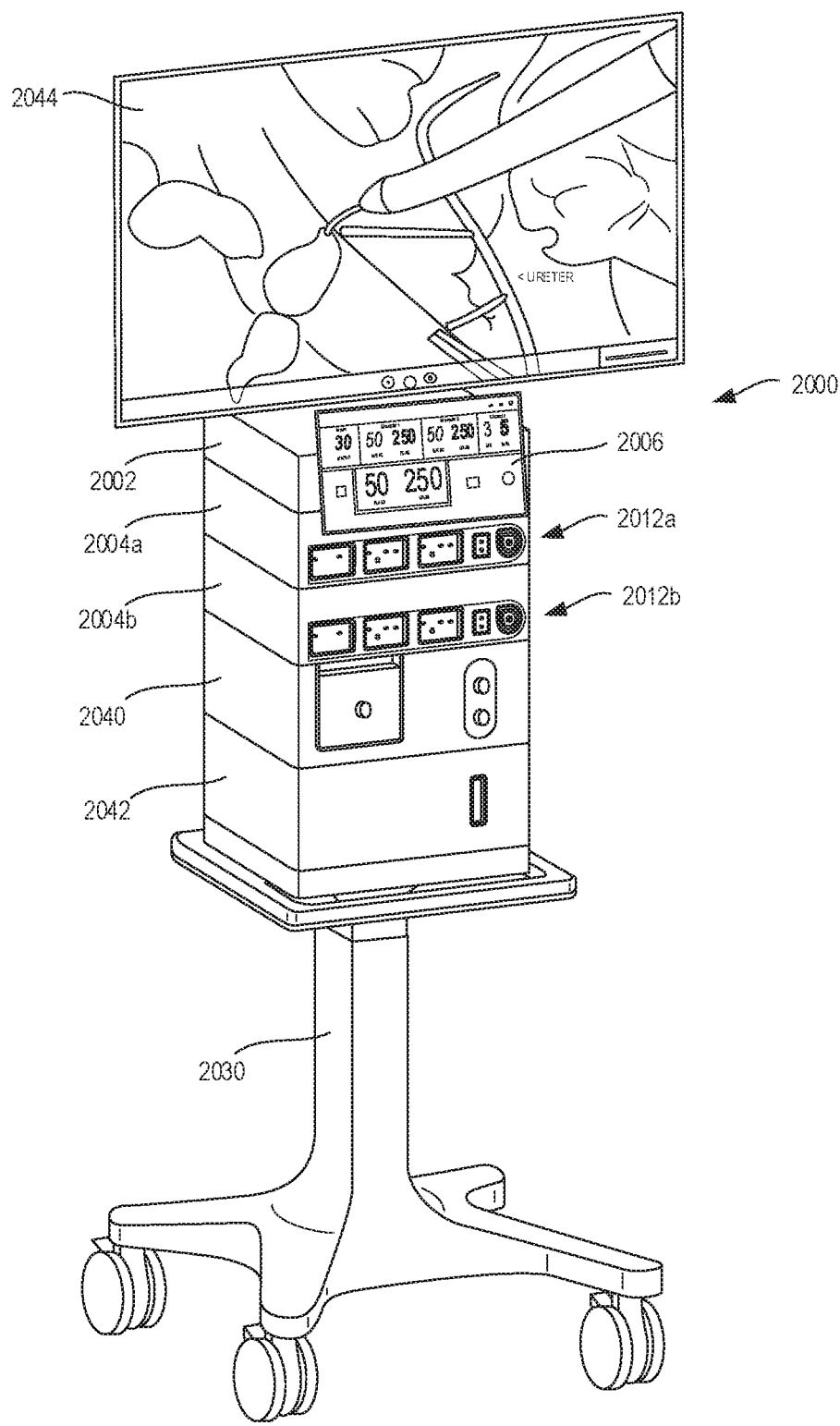
FIG. 10 is a fifth illustrative modular energy system configuration including a header module, a display screen, an energy module, an expanded energy module, a technology module, and a visualization module connected together and mounted to a cart, in accordance with at least one aspect of the present disclosure.

FIG. 10 illustrates a fifth illustrative configuration of the modular energy system 2000 including a header module 2002 (including a display screen 2006), a first energy module 2004a, a second energy module 2004b, a technology module 2040, and a visualization module 2042 connected together. Such a configuration can be suitable for endoscopic procedures by providing a dedicated surgical display 2044 for relaying the video feed from the scope coupled to the visualization module 2042. It should be noted that the configurations illustrated in FIGS. 7A-11 and described above are provided simply to illustrate the various concepts of the modular energy system 2000 and should not be interpreted to limit the modular energy system 2000 to the particular aforementioned configurations.

As noted above, the modular energy system 2000 can be communicably couplable to an external system, such as a surgical hub 2100 as illustrated in FIG. 11. Such external systems can include a display screen 2104 for displaying a visual feed from an endoscope (or a camera or another such visualization device) and/or data from the modular energy system 2000. Such external systems can also include a computer system 2102 for performing calculations or otherwise analyzing data generated or provided by the modular energy system 2000, controlling the functions or modes of the modular energy system 2000, and/or relaying data to a cloud computing system or another computer system. Such external systems could also coordinate actions between multiple modular energy systems 2000 and/or other surgical systems (e.g., a visualization system 108 and/or a robotic system 110 as described in connection with FIGS. 1 and 2).

Figure 12:
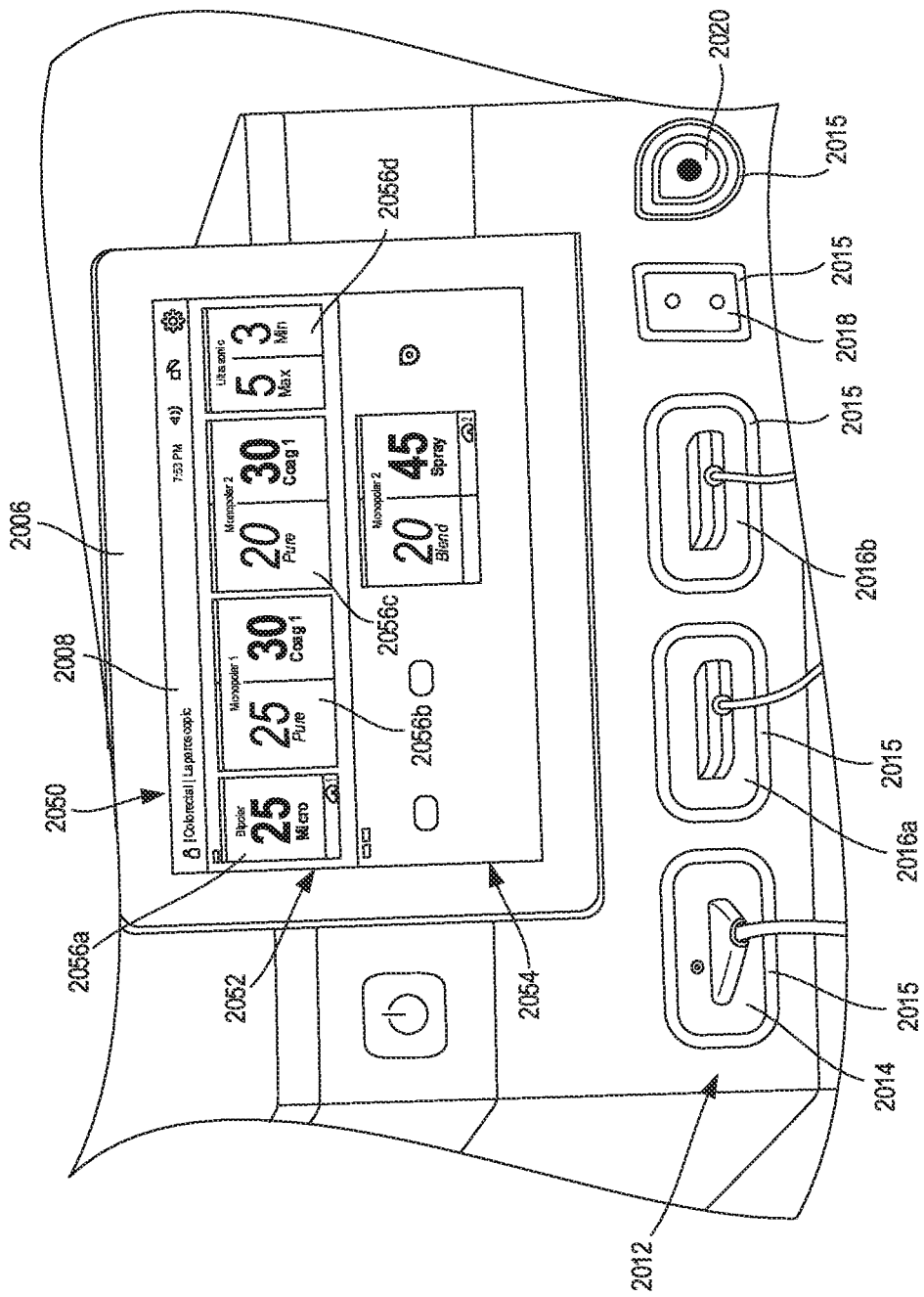
FIG. 12 is a perspective view of a header module of a modular energy system including a user interface, in accordance with at least one aspect of the present disclosure.

Referring now to FIG. 12, in some aspects, the header module 2002 can include or support a display 2006 configured for displaying a GUI 2008, as noted above. The display screen 2006 can include a touchscreen for receiving input from users in addition to displaying information. The controls displayed on the GUI 2008 can correspond to the module(s) 2001 that are connected to the header module 2002. In some aspects, different portions or areas of the GUI 2008 can correspond to particular modules 2001. For example, a first portion or area of the GUI 2008 can correspond to a first module and a second portion or area of the GUI 2008 can correspond to a second module. As different and/or additional modules 2001 are connected to the modular energy system stack, the GUI 2008 can adjust to accommodate the different and/or additional controls for each newly added module 2001 or remove controls for each module 2001 that is removed. Each portion of the display corresponding to a particular module connected to the header module 2002 can display controls, data, user prompts, and/or other information corresponding to that module. For example, in FIG. 12, a first or upper portion 2052 of the depicted GUI 2008 displays controls and data associated with an energy module 2004 that is connected to the header module 2002. In particular, the first portion 2052 of the GUI 2008 for the energy module 2004 provides first widget 2056a corresponding to the bipolar port 2014, a second widget 2056b corresponding to the first monopolar port 2016a, a third widget 2056c corresponding to the second monopolar port 2016b, and a fourth widget 2056d corresponding to the combination energy port 2020. Each of these widgets 2056a-d provides data related to its corresponding port of the port assembly 2012 and controls for controlling the modes and other features of the energy modality delivered by the energy module 2004 through the respective port of the port assembly 2012. For example, the widgets 2056a-d can be configured to display the power level of the surgical instrument connected to the respective port, change the operational mode of the surgical instrument connected to the respective port (e.g., change a surgical instrument from a first power level to a second power level and/or change a monopolar surgical instrument from a "spray" mode to a "blend" mode), and so on.

In one aspect, the header module 2002 can include various physical controls 2011 in addition to or in lieu of the GUI 2008. Such physical controls 2011 can include, for example, a power button that controls the application of power to each module 2001 that is connected to the header module 2002 in the modular energy system 2000. Alternatively, the power button can be displayed as part of the GUI 2008. Therefore, the header module 2002 can serve as a single point of contact and obviate the need to individually activate and deactivate each individual module 2001 from which the modular energy system 2000 is constructed.

In one aspect, the header module 2002 can display still images, videos, animations, and/or information associated with the surgical modules 2001 of which the modular energy system 2000 is constructed or the surgical devices that are communicably coupled to the modular energy system 2000. The still images and/or videos displayed by the header module 2002 can be received from an endoscope or another visualization device that is communicably coupled to the modular energy system 2000. The animations and/or information of the GUI 2008 can be overlaid on or displayed adjacent to the images or video feed.

In one aspect, the modules 2001 other than the header module 2002 can be configured to likewise relay information to users. For example, the energy module 2004 can include light assemblies 2015 disposed about each of the ports of the port assembly 2012. The light assemblies 2015 can be configured to relay information to the user regarding the port according to their color or state (e.g., flashing). For example, the light assemblies 2015 can change from a first color to a second color when a plug is fully seated within the respective port. In one aspect, the color or state of the light assemblies 2015 can be controlled by the header module 2002. For example, the header module 2002 can cause the light assembly 2015 of each port to display a color corresponding to the color display for the port on the GUI 2008.

Figure 13:
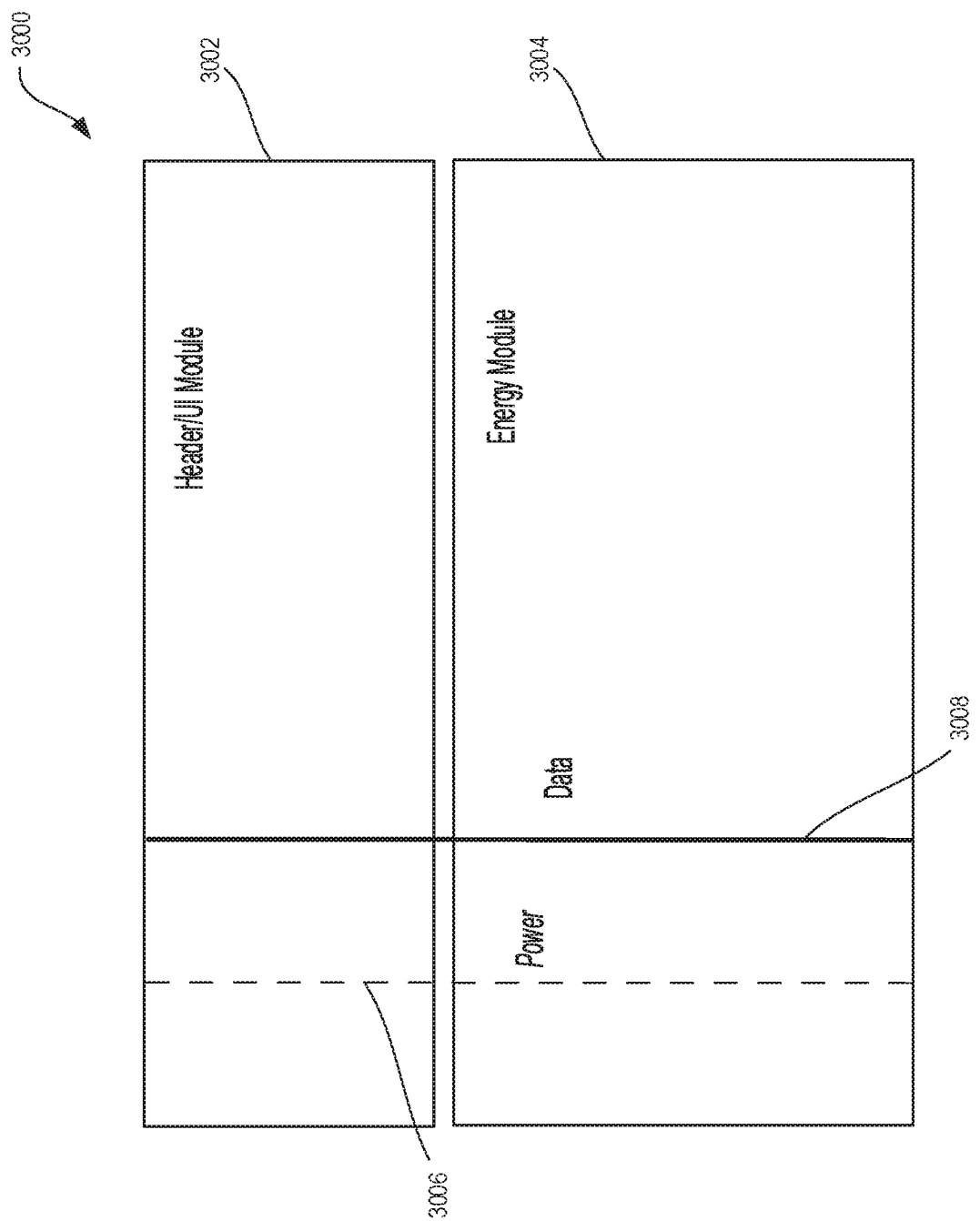
FIG. 13 is a block diagram of a stand-alone hub configuration of a modular energy system, in accordance with at least one aspect of the present disclosure.
Figure 14:
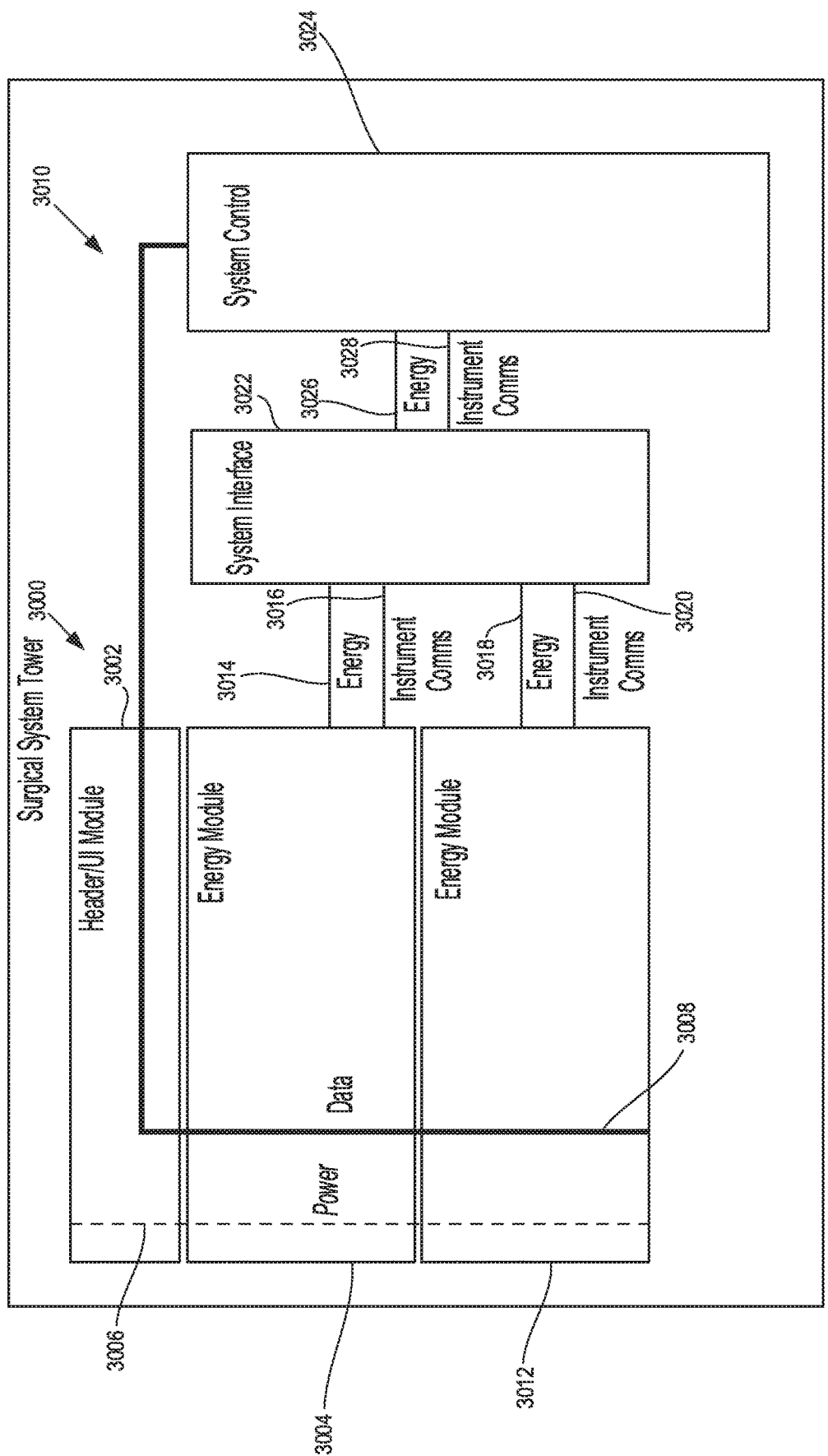
FIG. 14 is a block diagram of a hub configuration of a modular energy system integrated with a surgical control system, in accordance with at least one aspect of the present disclosure.

FIG. 13 is a block diagram of a stand-alone hub configuration of a modular energy system 3000, in accordance with at least one aspect of the present disclosure and FIG. 14 is a block diagram of a hub configuration of a modular energy system 3000 integrated with a surgical control system 3010, in accordance with at least one aspect of the present disclosure. As depicted in FIGS. 13 and 14, the modular energy system 3000 can be either utilized as stand-alone units or integrated with a surgical control system 3010 that controls and/or receives data from one or more surgical hub units. In the examples illustrated in FIGS. 13 and 14, the integrated header/UI module 3002 of the modular energy system 3000 includes a header module and a UI module integrated together as a singular module. In other aspects, the header module and the UI module can be provided as separate components that are communicatively coupled though a data bus 3008.

As illustrated in FIG. 13, an example of a stand-alone modular energy system 3000 includes an integrated header module/user interface (UI) module 3002 coupled to an energy module 3004. Power and data are transmitted between the integrated header/UI module 3002 and the energy module 3004 through a power interface 3006 and a data interface 3008. For example, the integrated header/UI module 3002 can transmit various commands to the energy module 3004 through the data interface 3008. Such commands can be based on user inputs from the UI. As a further example, power may be transmitted to the energy module 3004 through the power interface 3006.

In FIG. 14, a surgical hub configuration includes a modular energy system 3000 integrated with a control system 3010 and an interface system 3022 for managing, among other things, data and power transmission to and/or from the modular energy system 3000. The modular energy system depicted in FIG. 14 includes an integrated header module/UI module 3002, a first energy module 3004, and a second energy module 3012. In one example, a data transmission pathway is established between the system control unit 3024 of the control system 3010 and the second energy module 3012 through the first energy module 3004 and the header/UI module 3002 through a data interface 3008. In addition, a power pathway extends between the integrated header/UI module 3002 and the second energy module 3012 through the first energy module 3004 through a power interface 3006. In other words, in one aspect, the first energy module 3004 is configured to function as a power and data interface between the second energy module 3012 and the integrated header/UI module 3002 through the power interface 3006 and the data interface 3008. This arrangement allows the modular energy system 3000 to expand by seamlessly connecting additional energy modules to energy modules 3004, 3012 that are already connected to the integrated header/UI module 3002 without the need for dedicated power and energy interfaces within the integrated header/UI module 3002.

The system control unit 3024, which may be referred to herein as a control circuit, control logic, microprocessor, microcontroller, logic, or FPGA, or various combinations thereof, is coupled to the system interface 3022 via energy interface 3026 and instrument communication interface 3028. The system interface 3022 is coupled to the first energy module 3004 via a first energy interface 3014 and a first instrument communication interface 3016. The system interface 3022 is coupled to the second energy module 3012 via a second energy interface 3018 and a second instrument communication interface 3020. As additional modules, such as additional energy modules, are stacked in the modular energy system 3000, additional energy and communications interfaces are provided between the system interface 3022 and the additional modules.

The energy modules 3004, 3012 are connectable to a hub and can be configured to generate electrosurgical energy (e.g., bipolar or monopolar), ultrasonic energy, or a combination thereof (referred to herein as an "advanced energy" module) for a variety of energy surgical instruments. Generally, the energy modules 3004, 3012 include hardware/software interfaces, an ultrasonic controller, an advanced energy RF controller, bipolar RF controller, and control algorithms executed by the controller that receives outputs from the controller and controls the operation of the various energy modules 3004, 3012 accordingly. In various aspects of the present disclosure, the controllers described herein may be implemented as a control circuit, control logic, microprocessor, microcontroller, logic, or FPGA, or various combinations thereof.

Figure 15:
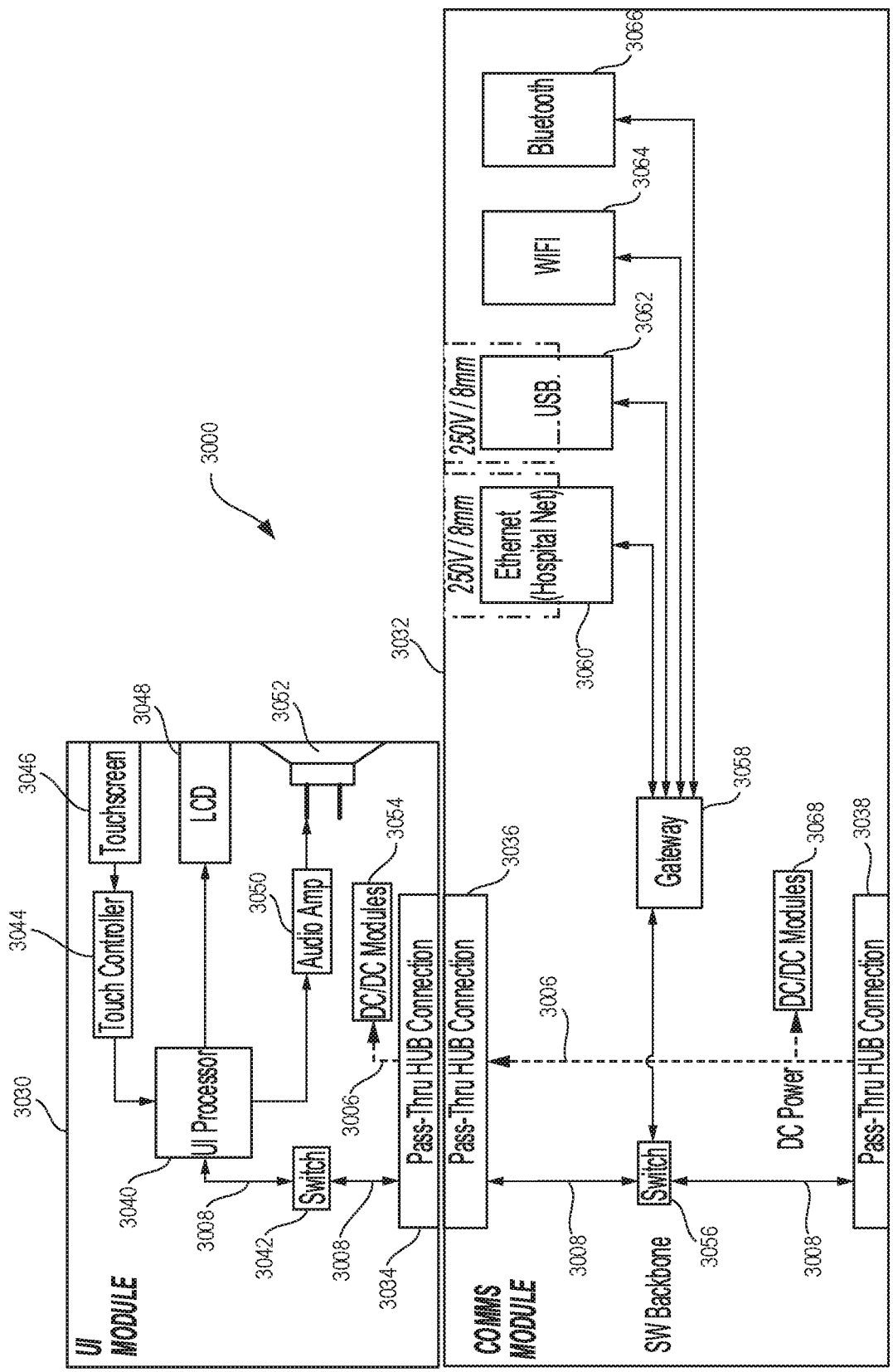
FIG. 15 is a block diagram of a user interface module coupled to a communications module of a modular energy system, in accordance with at least one aspect of the present disclosure.
Figure 16:
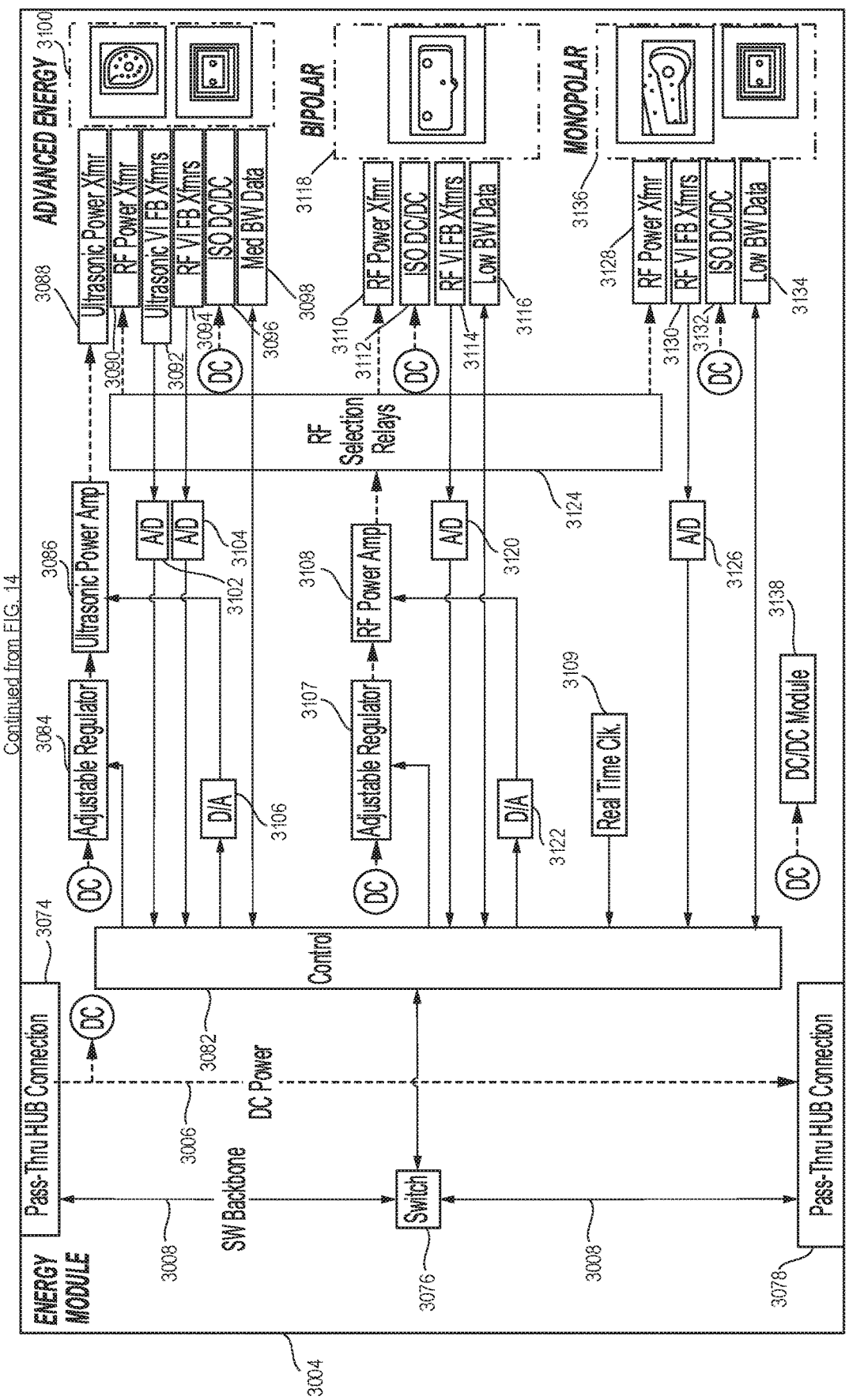
FIG. 16 is a block diagram of an energy module of a modular energy system, in accordance with at least one aspect of the present disclosure.
Figure 17A:
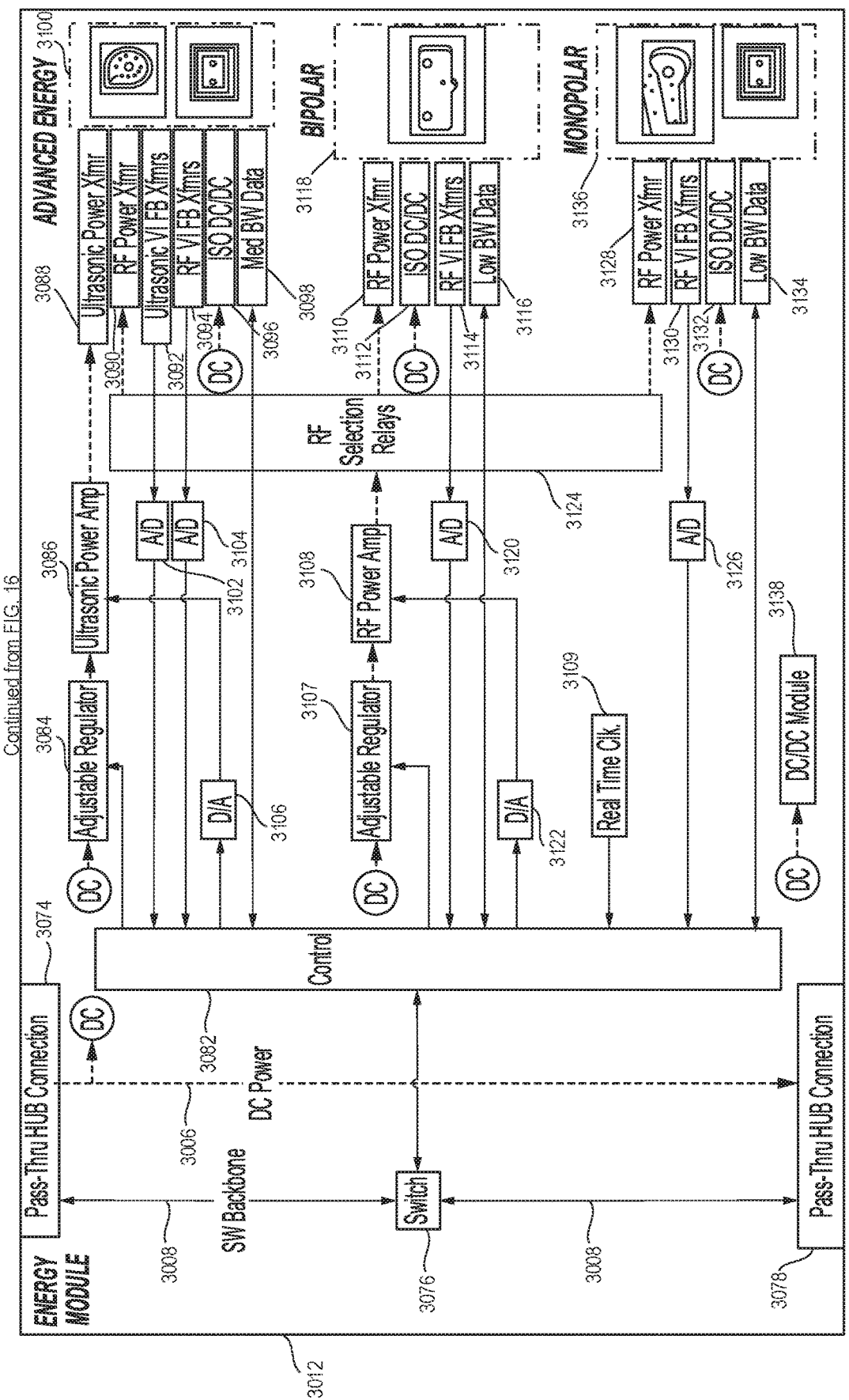
FIGS. 17A and 17B illustrate a block diagram of an energy module coupled to a header module of a modular energy system, in accordance with at least one aspect of the present disclosure.
Figure 17B:
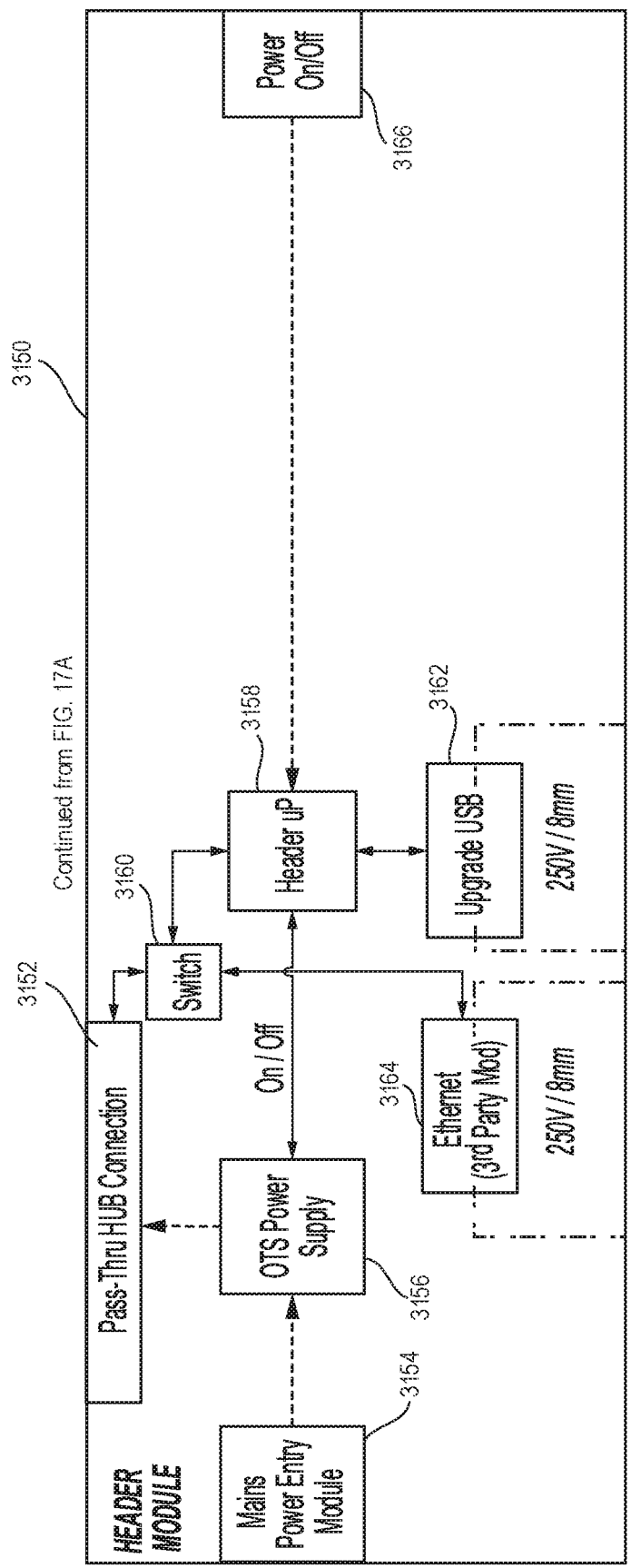

FIGS. 15-17 are block diagrams of various modular energy systems connected together to form a hub, in accordance with at least one aspect of the present disclosure. FIGS. 15-17 depict various diagrams (e.g., circuit or control diagrams) of hub modules. The modular energy system 3000 includes multiple energy modules 3004 (FIG. 16), 3012 (FIG. 17), a header module 3150 (FIG. 17), a UI module 3030 (FIG. 15), and a communications module 3032 (FIG. 15), in accordance with at least one aspect of the present disclosure. The UI module 3030 includes a touch screen 3046 displaying various relevant information and various user controls for controlling one or more parameters of the modular energy system 3000. The UI module 3030 is attached to the top header module 3150, but is separately housed so that it can be manipulated independently of the header module 3150. For example, the UI module 3030 can be picked up by a user and/or reattached to the header module 3150. Additionally, or alternatively, the UI module 3030 can be slightly moved relative to the header module 3150 to adjust its position and/or orientation. For example, the UI module 3030 can be tilted and/or rotated relative to the header module 3150.

In some aspects, the various hub modules can include light piping around the physical ports to communicate instrument status and also connect on-screen elements to corresponding instruments. Light piping is one example of an illumination technique that may be employed to alert a user to a status of a surgical instrument attached/connected to a physical port. In one aspect, illuminating a physical port with a particular light directs a user to connect a surgical instrument to the physical port. In another example, illuminating a physical port with a particular light alerts a user to an error related an existing connection with a surgical instrument.

Turning to FIG. 15, there is shown a block diagram of a user interface (UI) module 3030 coupled to a communications module 3032 via a pass-through hub connector 3034, in accordance with at least one aspect of the present disclosure. The UI module 3030 is provided as a separate component from a header module 3150 (shown in FIG. 17) and may be communicatively coupled to the header module 3150 via a communications module 3032, for example. In one aspect, the UI module 3030 can include a UI processor 3040 that is configured to represent declarative visualizations and behaviors received from other connected modules, as well as perform other centralized UI functionality, such as system configuration (e.g., language selection, module associations, etc.). The UI processor 3040 can be, for example, a processor or system on module (SOM) running a framework such as Qt, .NET WPF, Web server, or similar.

In the illustrated example, the UI module 3030 includes a touchscreen 3046, a liquid crystal display 3048 (LCD), and audio output 3052 (e.g., speaker, buzzer). The UI processor 3040 is configured to receive touchscreen inputs from a touch controller 3044 coupled between the touch screen 3046 and the UI processor 3040. The UI processor 3040 is configured to output visual information to the LCD display 3048 and to output audio information the audio output 3052 via an audio amplifier 3050. The UI processor 3040 is configured to interface to the communications module 3032 via a switch 3042 coupled to the pass-through hub connector 3034 to receive, process, and forward data from the source device to the destination device and control data communication therebetween. DC power is supplied to the UI module 3030 via DC/DC converter modules 3054. The DC power is passed through the pass-through hub connector 3034 to the communications module 3032 through the power bus 3006. Data is passed through the pass-through hub connector 3034 to the communications module 3032 through the data bus 3008. Switches 3042, 3056 receive, process, and forward data from the source device to the destination device.

Continuing with FIG. 15, the communications module 3032, as well as various surgical hubs and/or surgical systems can include a gateway 3058 that is configured to shuttle select traffic (i.e., data) between two disparate networks (e.g., an internal network and/or a hospital network) that are running different protocols. The communications module 3032 includes a first pass-through hub connector 3036 to couple the communications module 3032 to other modules. In the illustrated example, the communications module 3032 is coupled to the UI module 3030. The communications module 3032 is configured to couple to other modules (e.g., energy modules) via a second pass-through hub connector 3038 to couple the communications module 3032 to other modules via a switch 3056 disposed between the first and second pass-through hub connectors 3036, 3038 to receive, process, and forward data from the source device to the destination device and control data communication therebetween. The switch 3056 also is coupled to a gateway 3058 to communicate information between external communications ports and the UI module 3030 and other connected modules. The gateway 3058 may be coupled to various communications modules such as, for example, an Ethernet module 3060 to communicate to a hospital or other local network, a universal serial bus (USB) module 3062, a WiFi module 3064, and a Bluetooth module 3066, among others. The communications modules may be physical boards located within the communications module 3032 or may be a port to couple to remote communications boards.

Figure 18A:
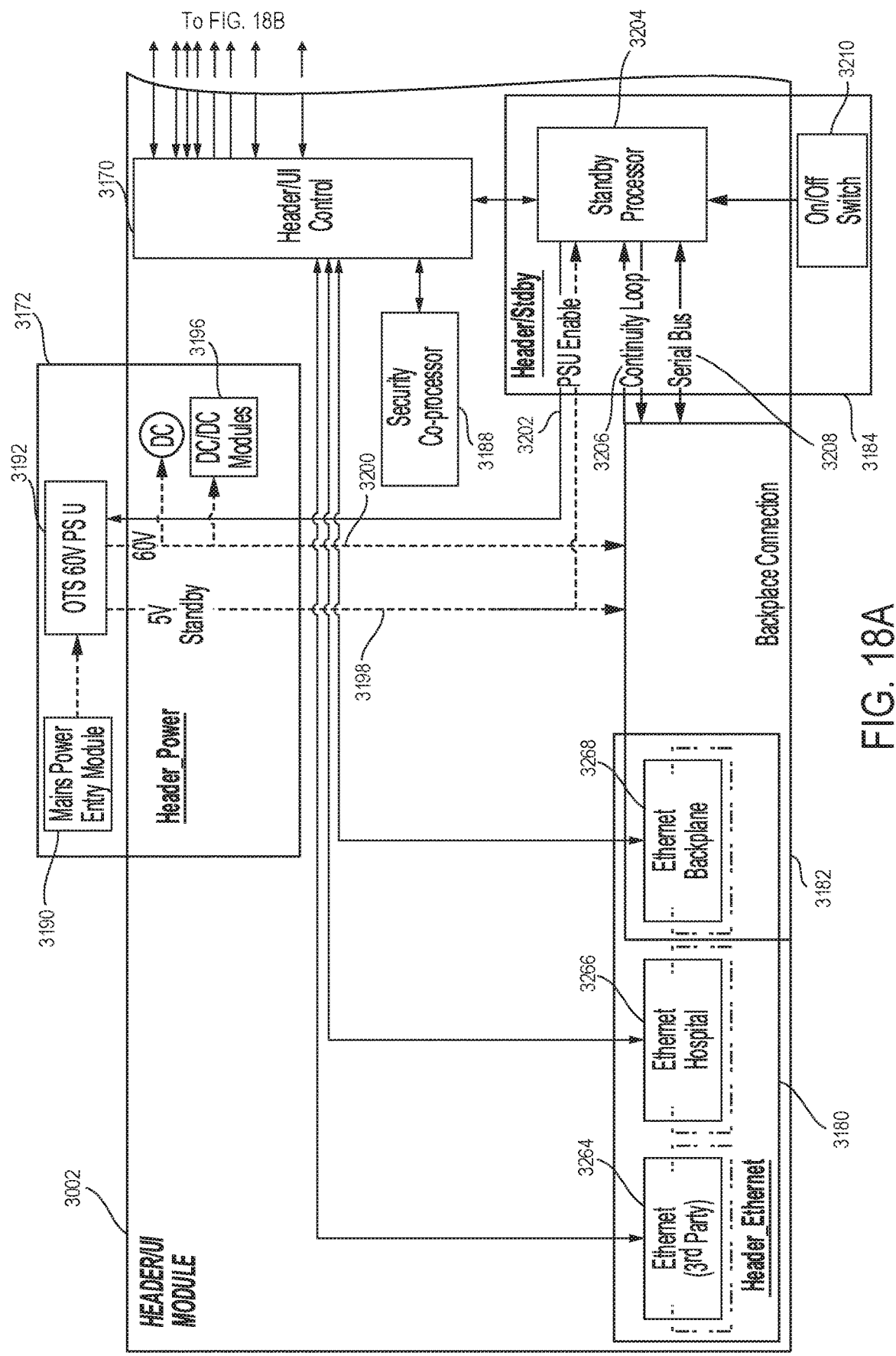
FIGS. 18A and 18B illustrate a block diagram of a header/user interface (UI) module of a modular energy system for a hub, such as the header module depicted in FIG. 15, in accordance with at least one aspect of the present disclosure.
Figure 18B:
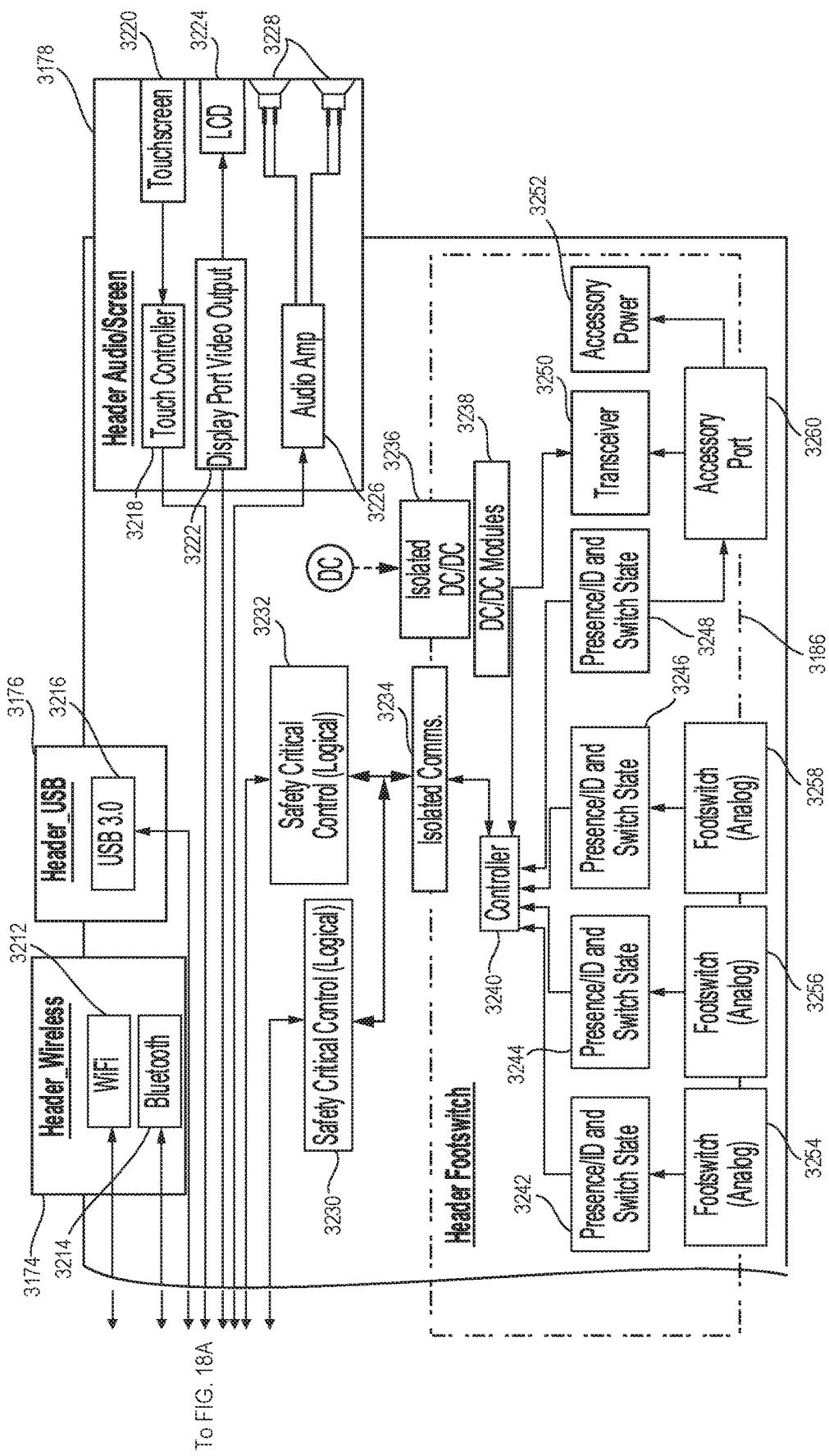

In some aspects, all of the modules (i.e., detachable hardware) are controlled by a single UI module 3030 that is disposed on or integral to a header module. FIG. 17 shows a stand alone header module 3150 to which the UI module 3030 can be attached. FIGS. 13, 14, and 18 show an integrated header/UI Module 3002. Returning now to FIG. 15, in various aspects, by consolidating all of the modules into a single, responsive UI module 3002, the system provides a simpler way to control and monitor multiple pieces of equipment at once. This approach drastically reduces footprint and complexity in an operating room (OR).

Turning to FIG. 16, there is shown a block diagram of an energy module 3004, in accordance with at least one aspect of the present disclosure. The communications module 3032 (FIG. 15) is coupled to the energy module 3004 via the second pass-through hub connector 3038 of the communications module 3032 and a first pass-through hub connector 3074 of the energy module 3004. The energy module 3004 may be coupled to other modules, such as a second energy module 3012 shown in FIG. 17, via a second pass-through hub connector 3078. Turning back to FIG. 16, a switch 3076 disposed between the first and second pass-through hub connectors 3074, 3078 receives, processes, and forwards data from the source device to the destination device and controls data communication therebetween. Data is received and transmitted through the data bus 3008. The energy module 3032 includes a controller 3082 to control various communications and processing functions of the energy module 3004.

DC power is received and transmitted by the energy module 3004 through the power bus 3006. The power bus 3006 is coupled to DC/DC converter modules 3138 to supply power to adjustable regulators 3084, 3107 and isolated DC/DC converter ports 3096, 3112, 3132.

In one aspect, the energy module 3004 can include an ultrasonic wideband amplifier 3086, which in one aspect may be a linear class H amplifier that is capable of generating arbitrary waveforms and drive harmonic transducers at low total harmonic distortion (THD) levels. The ultrasonic wideband amplifier 3086 is fed by a buck adjustable regulator 3084 to maximize efficiency and controlled by the controller 3082, which may be implemented as a digital signal processor (DSP) via a direct digital synthesizer (DDS), for example. The DDS can either be embedded in the DSP or implemented in the field-programmable gate array (FPGA), for example. The controller 3082 controls the ultrasonic wideband amplifier 3086 via a digital-to-analog converter 3106 (DAC). The output of the ultrasonic wideband amplifier 3086 is fed to an ultrasonic power transformer 3088, which is coupled to an ultrasonic energy output portion of an advanced energy receptacle 3100. Ultrasonic voltage (V) and current (I) feedback (FB) signals, which may be employed to compute ultrasonic impedance, are fed back to the controller 3082 via an ultrasonic VI FB transformer 3092 through an input portion of the advanced energy receptacle 3100. The ultrasonic voltage and current feedback signals are routed back to the controller 3082 through an analog-to-digital converter 3102 (A/D). Also coupled to the controller 3082 through the advanced energy receptacle 3100 is the isolated DC/DC converter port 3096, which receives DC power from the power bus 3006, and a medium bandwidth data port 3098.

In one aspect, the energy module 3004 can include a wideband RF power amplifier 3108, which in one aspect may be a linear class H amplifier that is capable of generating arbitrary waveforms and drive RF loads at a range of output frequencies. The wideband RF power amplifier 3108 is fed by an adjustable buck regulator 3107 to maximize efficiency and controlled by the controller 3082, which may be implemented as DSP via a DDS. The DDS can either be embedded in the DSP or implemented in the FPGA, for example. The controller 3082 controls the wideband RF amplifier 3086 via a DAC 3122. The output of the wideband RF power amplifier 3108 can be fed through RF selection relays 3124. The RF selection relays 3124 are configured to receive and selectively transmit the output signal of the wideband RF power amplifier 3108 to various other components of the energy module 3004. In one aspect, the output signal of the wideband RF power amplifier 3108 can be fed through RF selection relays 3124 to an RF power transformer 3110, which is coupled to an RF output portion of a bipolar RF energy receptacle 3118. Bipolar RF voltage (V) and current (I) feedback (FB) signals, which may be employed to compute RF impedance, are fed back to the controller 3082 via an RF VI FB transformer 3114 through an input portion of the bipolar RF energy receptacle 3118. The RF voltage and current feedback signals are routed back to the controller 3082 through an A/D 3120. Also coupled to the controller 3082 through the bipolar RF energy receptacle 3118 is the isolated DC/DC converter port 3112, which receives DC power from the power bus 3006, and a low bandwidth data port 3116.

As described above, in one aspect, the energy module 3004 can include RF selection relays 3124 driven by the controller 3082 (e.g., FPGA) at rated coil current for actuation and can also be set to a lower hold-current via pulse-width modulation (PWM) to limit steady-state power dissipation. Switching of the RF selection relays 3124 is achieved with force guided (safety) relays and the status of the contact state is sensed by the controller 3082 as a mitigation for any single fault conditions. In one aspect, the RF selection relays 3124 are configured to be in a first state, where an output RF signal received from an RF source, such as the wideband RF power amplifier 3108, is transmitted to a first component of the energy module 3004, such as the RF power transformer 3110 of the bipolar energy receptacle 3118. In a second aspect, the RF selection relays 3124 are configured to be in a second state, where an output RF signal received from an RF source, such as the wideband RF power amplifier 3108, is transmitted to a second component, such as an RF power transformer 3128 of a monopolar energy receptacle 3136, described in more detail below. In a general aspect, the RF selection relays 3124 are configured to be driven by the controller 3082 to switch between a plurality of states, such as the first state and the second state, to transmit the output RF signal received from the RF power amplifier 3108 between different energy receptacles of the energy module 3004.

As described above, the output of the wideband RF power amplifier 3108 can also fed through the RF selection relays 3124 to the wideband RF power transformer 3128 of the RF monopolar receptacle 3136. Monopolar RF voltage (V) and current (I) feedback (FB) signals, which may be employed to compute RF impedance, are fed back to the controller 3082 via an RF VI FB transformer 3130 through an input portion of the monopolar RF energy receptacle 3136. The RF voltage and current feedback signals are routed back to the controller 3082 through an A/D 3126. Also coupled to the controller 3082 through the monopolar RF energy receptacle 3136 is the isolated DC/DC converter port 3132, which receives DC power from the power bus 3006, and a low bandwidth data port 3134.

The output of the wideband RF power amplifier 3108 can also fed through the RF selection relays 3124 to the wideband RF power transformer 3090 of the advanced energy receptacle 3100. RF voltage (V) and current (I) feedback (FB) signals, which may be employed to compute RF impedance, are fed back to the controller 3082 via an RF VI FB transformer 3094 through an input portion of the advanced energy receptacle 3100. The RF voltage and current feedback signals are routed back to the controller 3082 through an A/D 3104.

FIG. 17 is a block diagram of a second energy module 3012 coupled to a header module 3150, in accordance with at least one aspect of the present disclosure. The first energy module 3004 shown in FIG. 16 is coupled to the second energy module 3012 shown in FIG. 17 by coupling the second pass-through hub connector 3078 of the first energy module 3004 to a first pass-through hub connector 3074 of the second energy module 3012. In one aspect, the second energy module 3012 can a similar energy module to the first energy module 3004, as is illustrated in FIG. 17. In another aspect, the second energy module 2012 can be a different energy module compared to the first energy module, such as an energy module illustrated in FIG. 19, described in more detail. The addition of the second energy module 3012 to the first energy module 3004 adds functionality to the modular energy system 3000.

The second energy module 3012 is coupled to the header module 3150 by connecting the pass-through hub connector 3078 to the pass-through hub connector 3152 of the header module 3150. In one aspect, the header module 3150 can include a header processor 3158 that is configured to manage a power button function 3166, software upgrades through the upgrade USB module 3162, system time management, and gateway to external networks (i.e., hospital or the cloud) via an Ethernet module 3164 that may be running different protocols. Data is received by the header module 3150 through the pass-through hub connector 3152. The header processor 3158 also is coupled to a switch 3160 to receive, process, and forward data from the source device to the destination device and control data communication therebetween. The header processor 3158 also is coupled to an OTS power supply 3156 coupled to a mains power entry module 3154.

FIG. 18 is a block diagram of a header/user interface (UI) module 3002 for a hub, such as the header module depicted in FIG. 15, in accordance with at least one aspect of the present disclosure. The header/UI module 3002 includes a header power module 3172, a header wireless module 3174, a header USB module 3176, a header audio/screen module 3178, a header network module 3180 (e.g., Ethernet), a backplane connector 3182, a header standby processor module 3184, and a header footswitch module 3186. These functional modules interact to provide the header/UI 3002 functionality. A header/UI controller 3170 controls each of the functional modules and the communication therebetween including safety critical control logic modules 3230, 3232 coupled between the header/UI controller 3170 and an isolated communications module 3234 coupled to the header footswitch module 3186. A security coprocessor 3188 is coupled to the header/UI controller 3170.

The header power module 3172 includes a mains power entry module 3190 coupled to an OTS power supply unit 3192 (PSU). Low voltage direct current (e.g., 5V) standby power is supplied to the header/UI module 3002 and other modules through a low voltage power bus 3198 from the OTS PSU 3192. High voltage direct current (e.g., 60V) is supplied to the header/UI module 3002 through a high voltage bus 3200 from the OTS PSU 3192. The high voltage DC supplies DC/DC converter modules 3196 as well as isolated DC/DC converter modules 3236. A standby processor 3204 of the header/standby module 3184 provides a PSU/enable signal 3202 to the OTS PSU 3192.

The header wireless module 3174 includes a WiFi module 3212 and a Bluetooth module 3214. Both the WiFi module 3212 and the Bluetooth module 3214 are coupled to the header/UI controller 3170. The Bluetooth module 3214 is used to connect devices without using cables and the Wi-Fi module 3212 provides high-speed access to networks such as the Internet and can be employed to create a wireless network that can link multiple devices such as, for examples, multiple energy modules or other modules and surgical instruments, among other devices located in the operating room. Bluetooth is a wireless technology standard that is used to exchange data over short distances, such as, less than 30 feet.

The header USB module 3176 includes a USB port 3216 coupled to the header/UI controller 3170. The USB module 3176 provides a standard cable connection interface for modules and other electronics devices over short-distance digital data communications. The USB module 3176 allows modules comprising USB devices to be connected to each other with and transfer digital data over USB cables.

The header audio/screen module 3178 includes a touchscreen 3220 coupled to a touch controller 3218. The touch controller 3218 is coupled to the header/UI controller 3170 to read inputs from the touchscreen 3220. The header/UI controller 3170 drives an LCD display 3224 through a display/port video output signal 3222. The header/UI controller 3170 is coupled to an audio amplifier 3226 to drive one or more speakers 3228.

In one aspect, the header/UI module 3002 provides a touchscreen 3220 user interface configured to control modules connected to one control or header module 3002 in a modular energy system 3000. The touchscreen 3220 can be used to maintain a single point of access for the user to adjust all modules connected within the modular energy system 3000. Additional hardware modules (e.g., a smoke evacuation module) can appear at the bottom of the user interface LCD display 3224 when they become connected to the header/UI module 3002, and can disappear from the user interface LCD display 3224 when they are disconnected from the header/UI module 3002.

Further, the user touchscreen 3220 can provide access to the settings of modules attached to the modular energy system 3000. Further, the user interface LCD display 3224 arrangement can be configured to change according to the number and types of modules that are connected to the header/UI module 3002. For example, a first user interface can be displayed on the LCD display 3224 for a first application where one energy module and one smoke evacuation module are connected to the header/UI module 3002, and a second user interface can be displayed on the LCD display 3224 for a second application where two energy modules are connected to the header/UI module 3002. Further, the user interface can alter its display on the LCD display 3224 as modules are connected and disconnected from the modular energy system 3000.

In one aspect, the header/UI module 3002 provides a user interface LCD display 3224 configured to display on the LCD display coloring corresponds to the port lighting. In one aspect, the coloring of the instrument panel and the LED light around its corresponding port will be the same or otherwise correspond with each other. Each color can, for example, convey a unique meaning. This way, the user will be able to quickly assess which instrument the indication is referring to and the nature of the indication. Further, indications regarding an instrument can be represented by the changing of color of the LED light lined around its corresponding port and the coloring of its module. Still further, the message on screen and hardware/software port alignment can also serve to convey that an action must be taken on the hardware, not on the interface. In various aspects, all other instruments can be used while alerts are occurring on other instruments. This allows the user to be able to quickly assess which instrument the indication is referring to and the nature of the indication.

In one aspect, the header/UI module 3002 provides a user interface screen configured to display on the LCD display 3224 to present procedure options to a user. In one aspect, the user interface can be configured to present the user with a series of options (which can be arranged, e.g., from broad to specific). After each selection is made, the modular energy system 3000 presents the next level until all selections are complete. These settings could be managed locally and transferred via a secondary means (such as a USB thumb drive). Alternatively, the settings could be managed via a portal and automatically distributed to all connected systems in the hospital.

The procedure options can include, for example, a list of factory preset options categorized by specialty, procedure, and type of procedure. Upon completing a user selection, the header module can be configured to set any connected instruments to factory-preset settings for that specific procedure. The procedure options can also include, for example, a list of surgeons, then subsequently, the specialty, procedure, and type. Once a user completes a selection, the system may suggest the surgeon's preferred instruments and set those instrument's settings according to the surgeon's preference (i.e., a profile associated with each surgeon storing the surgeon's preferences).

In one aspect, the header/UI module 3002 provides a user interface screen configured to display on the LCD display 3224 critical instrument settings. In one aspect, each instrument panel displayed on the LCD display 3224 of the user interface corresponds, in placement and content, to the instruments plugged into the modular energy system 3000. When a user taps on a panel, it can expand to reveal additional settings and options for that specific instrument and the rest of the screen can, for example, darken or otherwise be de-emphasized.

In one aspect, the header/UI module 3002 provides an instrument settings panel of the user interface configured to comprise/display controls that are unique to an instrument and allow the user to increase or decrease the intensity of its output, toggle certain functions, pair it with system accessories like a footswitch connected to header footswitch module 3186, access advanced instrument settings, and find additional information about the instrument. In one aspect, the user can tap/select an "Advanced Settings" control to expand the advanced settings drawer displayed on the user interface LCD display 3224. In one aspect, the user can then tap/select an icon at the top right-hand corner of the instrument settings panel or tap anywhere outside of the panel and the panel will scale back down to its original state. In these aspects, the user interface is configured to display on the LCD display 3224 only the most critical instrument settings, such as power level and power mode, on the ready/home screen for each instrument panel. This is to maximize the size and readability of the system from a distance. In some aspects, the panels and the settings within can be scaled proportionally to the number of instruments connected to the system to further improve readability. As more instruments are connected, the panels scale to accommodate a greater amount of information.

The header network module 3180 includes a plurality of network interfaces 3264, 3266, 3268 (e.g., Ethernet) to network the header/UI module 3002 to other modules of the modular energy system 3000. In the illustrated example, one network interface 3264 may be a 3rd party network interface, another network interface 3266 may be a hospital network interface, and yet another network interface 3268 may be located on the backplane network interface connector 3182.

The header standby processor module 3184 includes a standby processor 3204 coupled to an On/Off switch 3210. The standby processor 3204 conducts an electrical continuity test by checking to see if electrical current flows in a continuity loop 3206. The continuity test is performed by placing a small voltage across the continuity loop 3206. A serial bus 3208 couples the standby processor 3204 to the backplane connector 3182.

The header footswitch module 3186 includes a controller 3240 coupled to a plurality of analog footswitch ports 3254, 3256, 3258 through a plurality of corresponding presence/ID and switch state modules 3242, 3244, 3246, respectively. The controller 3240 also is coupled to an accessory port 3260 via a presence/ID and switch state module 3248 and a transceiver module 3250. The accessory port 3260 is powered by an accessory power module 3252. The controller 3240 is coupled to header/UI controller 3170 via an isolated communication module 3234 and first and second safety critical control modules 3230, 3232. The header footswitch module 3186 also includes DC/DC converter modules 3238.

In one aspect, the header/UI module 3002 provides a user interface screen configured to display on the LCD display 3224 for controlling a footswitch connected to any one of the analog footswitch ports 3254, 3256, 3258. In some aspects, when the user plugs in a non hand-activated instrument into any one of the analog footswitch ports 3254, 3256, 3258, the instrument panel appears with a warning icon next to the footswitch icon. The instrument settings can be, for example, greyed out, as the instrument cannot be activated without a footswitch.

When the user plugs in a footswitch into any one of the analog footswitch ports 3254, 3256, 3258, a pop-up appears indicating that a footswitch has been assigned to that instrument. The footswitch icon indicates that a footswitch has been plugged in and assigned to the instrument. The user can then tap/select on that icon to assign, reassign, unassign, or otherwise change the settings associated with that footswitch. In these aspects, the system is configured to automatically assign footswitches to non hand-activated instruments using logic, which can further assign single or double-pedal footswitches to the appropriate instrument. If the user wants to assign/reassign footswitches manually there are two flows that can be utilized.

In one aspect, the header/UI module 3002 provides a global footswitch button. Once the user taps on the global footswitch icon (located in the upper right of the user interface LCD display 3224), the footswitch assignment overlay appears and the contents in the instrument modules dim. A (e.g., photo-realistic) representation of each attached footswitch (dual or single-pedal) appears on the bottom if unassigned to an instrument or on the corresponding instrument panel. Accordingly, the user can drag and drop these illustrations into, and out of, the boxed icons in the footswitch assignment overlay to assign, unassign, and reassign footswitches to their respective instruments.

In one aspect, the header/UI module 3002 provides a user interface screen displayed on the LCD display 3224 indicating footswitch auto-assignment, in accordance with at least one aspect of the present disclosure. As discussed above, the modular energy system 3000 can be configured to auto-assign a footswitch to an instrument that does not have hand activation. In some aspects, the header/UI module 3002 can be configured to correlate the colors displayed on the user interface LCD display 3224 to the lights on the modules themselves as means of tracking physical ports with user interface elements.

In one aspect, the header/UI module 3002 may be configured to depict various applications of the user interface with differing number of modules connected to the modular energy system 3000. In various aspects, the overall layout or proportion of the user interface elements displayed on the LCD display 3224 can be based on the number and type of instruments plugged into the header/UI module 3002. These scalable graphics can provide the means to utilize more of the screen for better visualization.

In one aspect, the header/UI module 3002 may be configured to depict a user interface screen on the LCD display 3224 to indicate which ports of the modules connected to the modular energy system 3000 are active. In some aspects, the header/UI module 3002 can be configured to illustrate active versus inactive ports by highlighting active ports and dimming inactive ports. In one aspect, ports can be represented with color when active (e.g., monopolar tissue cut with yellow, monopolar tissue coagulation with blue, bipolar tissue cut with blue, advanced energy tissue cut with warm white, and so on). Further, the displayed color will match the color of the light piping around the ports. The coloring can further indicate that the user cannot change settings of other instruments while an instrument is active. As another example, the header/UI module 3002 can be configured to depict the bipolar, monopolar, and ultrasonic ports of a first energy module as active and the monopolar ports of a second energy module as likewise active.

In one aspect, the header/UI module 3002 can be configured to depict a user interface screen on the LCD display 3224 to display a global settings menu. In one aspect, the header/UI module 3002 can be configured to display a menu on the LCD display 3224 to control global settings across any modules connected to the modular energy system 3000. The global settings menu can be, for example, always displayed in a consistent location (e.g., always available in upper right hand corner of main screen).

In one aspect, the header/UI module 3002 can be configured to depict a user interface screen on the LCD display 3224 configured to prevent changing of settings while a surgical instrument is in use. In one example, the header/UI module 3002 can be configured to prevent settings from being changed via a displayed menu when a connected instrument is active. The user interface screen can include, for example, an area (e.g., the upper left hand corner) that is reserved for indicating instrument activation while a settings menu is open. In one aspect, a user has opened the bipolar settings while monopolar coagulation is active. In one aspect, the settings menu could then be used once the activation is complete. In one aspect, the header/UI module 3002 can be is configured to never overlay any menus or other information over the dedicated area for indicating critical instrument information in order to maintain display of critical information.

In one aspect, the header/UI module 3002 can be configured to depict a user interface screen on the LCD display 3224 configured to display instrument errors. In one aspect, instrument error warnings may be displayed on the instrument panel itself, allowing user to continue to use other instruments while a nurse troubleshoots the error. This allows users to continue the surgery without the need to stop the surgery to debug the instrument.

In one aspect, the header/UI module 3002 can be configured to depict a user interface screen on the LCD display 3224 to display different modes or settings available for various instruments. In various aspects, the header/UI module 3002 can be configured to display settings menus that are appropriate for the type or application of surgical instrument (s) connected to the stack/hub. Each settings menu can provide options for different power levels, energy delivery profiles, and so on that are appropriate for the particular instrument type. In one aspect, the header/UI module 3002 can be configured to display different modes available for bipolar, monopolar cut, and monopolar coagulation applications.

In one aspect, the header/UI module 3002 can be configured to depict a user interface screen on the LCD display 3224 to display pre-selected settings. In one aspect, the header/UI module 3002 can be configured to receive selections for the instrument/device settings before plugging in instruments so that the modular energy system 3000 is ready before the patient enters the operating room. In one aspect, the user can simply click a port and then change the settings for that port. In the depicted aspect, the selected port appears as faded to indicate settings are set, but no instrument is plugged into that port.

Figure 19:
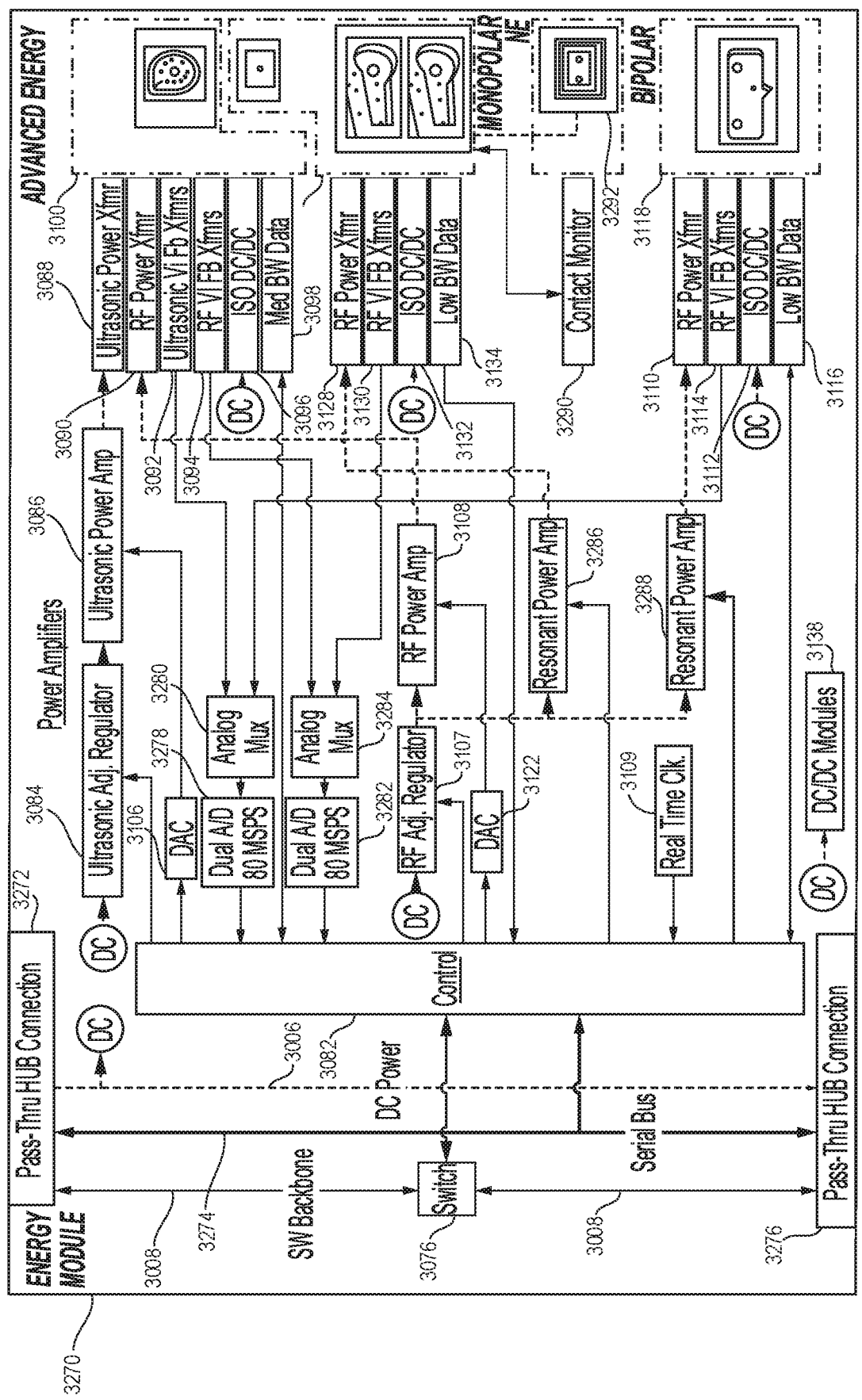
FIG. 19 is a block diagram of an energy module for a hub, such as the energy module depicted in FIGS. 13-18B, in accordance with at least one aspect of the present disclosure.

FIG. 19 is a block diagram of an energy module 3270 for a hub, such as the energy module depicted in FIGS. 13, 14, 16, and 17, in accordance with at least one aspect of the present disclosure. The energy module 3270 is configured to couple to a header module, header/UI module, and other energy modules via the first and second pass-through hub connectors 3272, 3276. A switch 3076 disposed between the first and second pass-through hub connectors 3272, 3276 receives, processes, and forwards data from the source device to the destination device and controls data communication therebetween. Data is received and transmitted through the data bus 3008. The energy module 3270 includes a controller 3082 to control various communications and processing functions of the energy module 3270.

DC power is received and transmitted by the energy module 3270 through the power bus 3006. The power bus 3006 is coupled to the DC/DC converter modules 3138 to supply power to adjustable regulators 3084, 3107 and isolated DC/DC converter ports 3096, 3112, 3132.

In one aspect, the energy module 3270 can include an ultrasonic wideband amplifier 3086, which in one aspect may be a linear class H amplifier that is capable of generating arbitrary waveforms and drive harmonic transducers at low total harmonic distortion (THD) levels. The ultrasonic wideband amplifier 3086 is fed by a buck adjustable regulator 3084 to maximize efficiency and controlled by the controller 3082, which may be implemented as a digital signal processor (DSP) via a direct digital synthesizer (DDS), for example. The DDS can either be embedded in the DSP or implemented in the field-programmable gate array (FPGA), for example. The controller 3082 controls the ultrasonic wideband amplifier 3086 via a digital-to-analog converter 3106 (DAC). The output of the ultrasonic wideband amplifier 3086 is fed to an ultrasonic power transformer 3088, which is coupled to an ultrasonic energy output portion of the advanced energy receptacle 3100. Ultrasonic voltage (V) and current (I) feedback (FB) signals, which may be employed to compute ultrasonic impedance, are fed back to the controller 3082 via an ultrasonic VI FB transformer 3092 through an input portion of the advanced energy receptacle 3100. The ultrasonic voltage and current feedback signals are routed back to the controller 3082 through an analog multiplexer 3280 and a dual analog-to-digital converter 3278 (A/D). In one aspect, the dual A/D 3278 has a sampling rate of 80 MSPS. Also coupled to the controller 3082 through the advanced energy receptacle 3100 is the isolated DC/DC converter port 3096, which receives DC power from the power bus 3006, and a medium bandwidth data port 3098.

In one aspect, the energy module 3270 can include a plurality of wideband RF power amplifiers 3108, 3286, 3288, among others, which in one aspect, each of the wideband RF power amplifiers 3108, 3286, 3288 may be linear class H amplifiers capable of generating arbitrary waveforms and drive RF loads at a range of output frequencies. Each of the wideband RF power amplifiers 3108, 3286, 3288 are fed by an adjustable buck regulator 3107 to maximize efficiency and controlled by the controller 3082, which may be implemented as DSP via a DDS. The DDS can either be embedded in the DSP or implemented in the FPGA, for example. The controller 3082 controls the first wideband RF power amplifier 3108 via a DAC 3122.

Unlike the energy modules 3004, 3012 shown and described in FIGS. 16 and 17, the energy module 3270 does not include RF selection relays configured to receive an RF output signal from the adjustable buck regulator 3107. In addition, unlike the energy modules 3004, 3012 shown and described in FIGS. 16 and 17, the energy module 3270 includes a plurality of wideband RF power amplifiers 3108, 3286, 3288 instead of a single RF power amplifier. In one aspect, the adjustable buck regulator 3107 can switch between a plurality of states, in which the adjustable buck regulator 3107 outputs an output RF signal to one of the plurality of wideband RF power amplifiers 3108, 3286, 3288 connected thereto. The controller 3082 is configured to switch the adjustable buck regulator 3107 between the plurality of states. In a first state, the controller drives the adjustable buck regulator 3107 to output an RF energy signal to the first wideband RF power amplifier 3108. In a second state, the controller drives the adjustable buck regulator 3107 to output an RF energy signal to the second wideband RF power amplifier 3286. In a third state, the controller drives the adjustable buck regulator 3107 to output an RF energy signal to the third wideband RF power amplifier 3288.

The output of the first wideband RF power amplifier 3108 can be fed to an RF power transformer 3090, which is coupled to an RF output portion of an advanced energy receptacle 3100. RF voltage (V) and current (I) feedback (FB) signals, which may be employed to compute RF impedance, are fed back to the controller 3082 via RF VI FB transformers 3094 through an input portion of the advanced energy receptacle 3100. The RF voltage and current feedback signals are routed back to the controller 3082 through the RF VI FB transformers 3094, which are coupled to an analog multiplexer 3284 and a dual A/D 3282 coupled to the controller 3082. In one aspect, the dual A/D 3282 has a sampling rate of 80 MSPS.

The output of the second RF wideband power amplifier 3286 is fed through an RF power transformer 3128 of the RF monopolar receptacle 3136. Monopolar RF voltage (V) and current (I) feedback (FB) signals, which may be employed to compute RF impedance, are fed back to the controller 3082 via RF VI FB transformers 3130 through an input portion of the monopolar RF energy receptacle 3136. The RF voltage and current feedback signals are routed back to the controller 3082 through the analog multiplexer 3284 and the dual A/D 3282. Also coupled to the controller 3082 through the monopolar RF energy receptacle 3136 is the isolated DC/DC converter port 3132, which receives DC power from the power bus 3006, and a low bandwidth data port 3134.

The output of the third RF wideband power amplifier 3288 is fed through an RF power transformer 3110 of a bipolar RF receptacle 3118. Bipolar RF voltage (V) and current (I) feedback (FB) signals, which may be employed to compute RF impedance, are fed back to the controller 3082 via RF VI FB transformers 3114 through an input portion of the bipolar RF energy receptacle 3118. The RF voltage and current feedback signals are routed back to the controller 3082 through the analog multiplexer 3280 and the dual A/D 3278. Also coupled to the controller 3082 through the bipolar RF energy receptacle 3118 is the isolated DC/DC converter port 3112, which receives DC power from the power bus 3006, and a low bandwidth data port 3116.

A contact monitor 3290 is coupled to an NE receptacle 3292. Power is fed to the NE receptacle 3292 from the monopolar receptacle 3136.

In one aspect, with reference to FIGS. 13-19, the modular energy system 3000 can be configured to detect instrument presence in a receptacle 3100, 3118, 3136 via a photo-interrupter, magnetic sensor, or other non-contact sensor integrated into the receptacle 3100, 3118, 3136. This approach prevents the necessity of allocating a dedicated presence pin on the MTD connector to a single purpose and instead allows multi-purpose functionality for MTD signal pins 6-9 while continuously monitoring instrument presence.

In one aspect, with reference to FIGS. 13-19, the modules of the modular energy system 3000 can include an optical link allowing high speed communication (10-50 Mb/s) across the patient isolation boundary. This link would carry device communications, mitigation signals (watchdog, etc.), and low bandwidth run-time data. In some aspects, the optical link(s) will not contain real-time sampled data, which can be done on the non-isolated side.

In one aspect, with reference to FIGS. 13-19, the modules of the modular energy system 3000 can include a multi-function circuit block which can: (i) read presence resistor values via A/D and current source, (ii) communicate with legacy instruments via hand switch Q protocols, (iii) communicate with instruments via local bus 1-Wire protocols, and (iv) communicate with CAN FD-enabled surgical instruments. When a surgical instrument is properly identified by an energy generator module, the relevant pin functions and communications circuits are enabled, while the other unused functions are disabled or disconnected and set to a high impedance state.

In one aspect, with reference to FIGS. 13-19, the modules of the modular energy system 3000 can include a pulse/stimulation/auxiliary amplifier. This is a flexible-use amplifier based on a full-bridge output and incorporates functional isolation. This allows its differential output to be referenced to any output connection on the applied part (except, in some aspects, a monopolar active electrode). The amplifier output can be either small signal linear (pulse/stim) with waveform drive provided by a DAC or a square wave drive at moderate output power for DC applications such as DC motors, illumination, FET drive, etc. The output voltage and current are sensed with functionally isolated voltage and current feedback to provide accurate impedance and power measurements to the FPGA. Paired with a CAN FD-enabled instrument, this output can offer motor/motion control drive, while position or velocity feedback is provided by the CAN FD interface for closed loop control.

As described in greater detail herein, a modular energy system comprises a header module and one or more functional or surgical modules. In various instances, the modular energy system is a modular energy system. In various instances, the surgical modules include energy modules, communication modules, user interface modules; however, the surgical modules are envisioned to be any suitable type of functional or surgical module for use with the modular energy system.

Modular energy system offers many advantages in a surgical procedure, as described above in connection with the modular energy systems 2000 (FIGS. 6-12), 3000 (FIGS. 13-15). However, cable management and setup/teardown time can be a significant deterrent. Various aspects of the present disclosure provide a modular energy system with a single power cable and a single power switch to control startup and shutdown of the entire modular energy system, which obviated the need to individually activate and deactivate each individual module from which the modular energy system is constructed. Also, various aspects of the present disclosure provide a modular energy system with power management schemes that facilitate a safe and, in some instances, concurrent delivery of power to the modules of a modular energy system.

Figure 20:
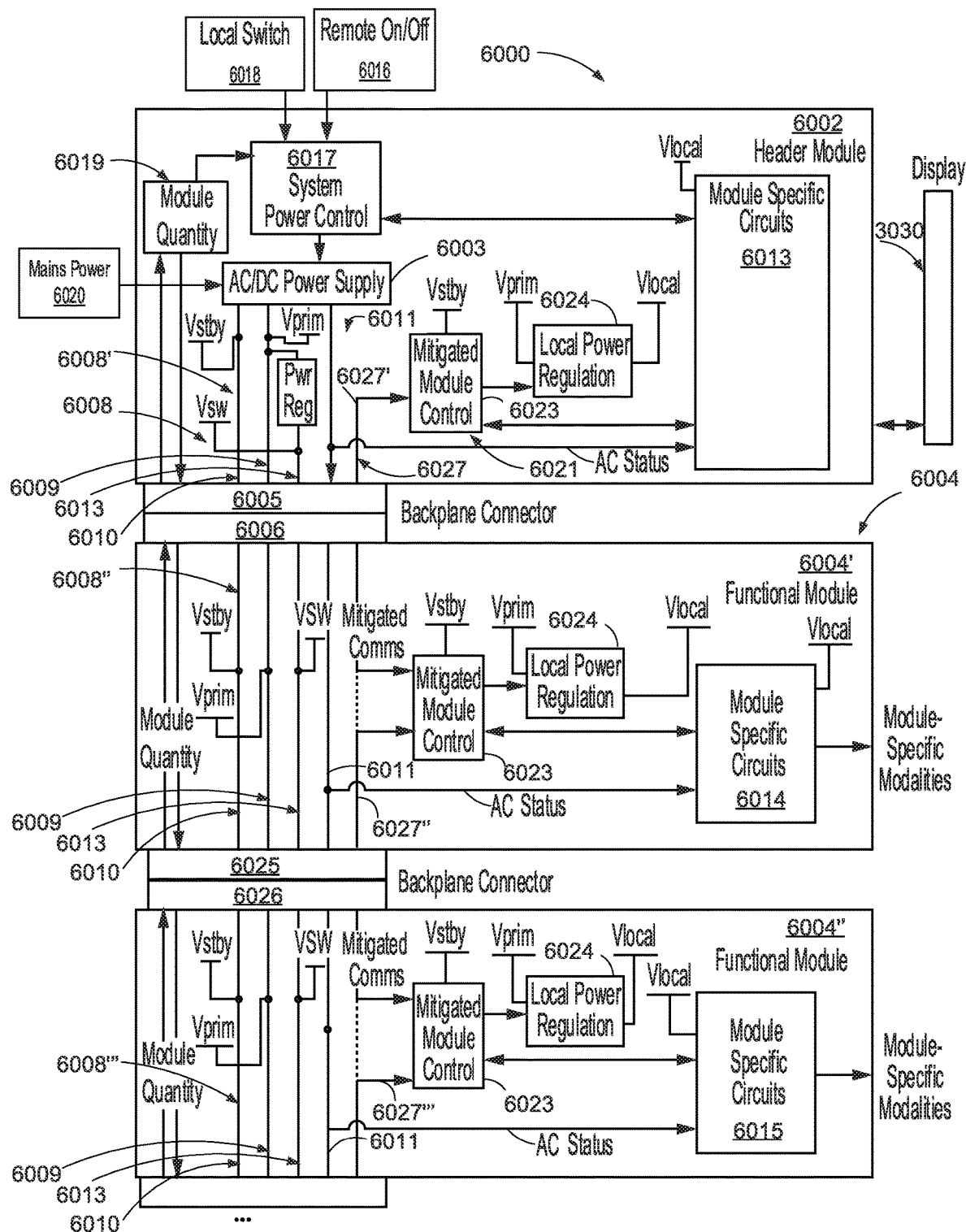
FIG. 20 is a schematic diagram of a modular energy system stack illustrating a power backplane, in accordance with at least one aspect of the present disclosure.

In various aspects, as illustrated in FIG. 20, a modular energy system 6000 that is similar in many respects to the modular energy systems 2000 (FIGS. 6-12), 3000 (FIGS. 13-15). For the sake of brevity, various details of the modular energy system 6000, which are similar to the modular energy system 2000 and/or the modular energy system 3000, are not repeated herein.

The modular energy system 6000 comprises a header module 6002 and an "N" number of surgical modules 6004, where "N" is an integer greater than or equal to one. In various examples, the modular energy system 6000 includes a UI module such as, for example, the UI module 3030 and/or a communication module such as, for example, the communication module 3032. Furthermore, pass-through hub connectors couple individual modules to one another in a stack configuration. In the example of FIG. 20, the header module 6002 is coupled to a surgical module 6004 via pass-through hub connectors 6005, 6006.

The modular energy system 6000 comprises an example power architecture that consists of a single AC/DC power supply 6003 that provides power to all the surgical modules in the stack. The AC/DC power supply 6003 is housed in the header module 6002, and utilizes a power backplane 6008 to distribute power to each module in the stack. The example of FIG. 20 demonstrates three separate power domains on the power backplane 6008: a primary power domain 6009, a standby power domain 6010, and an Ethernet switch power domain 6013.

In the example illustrated in FIG. 20, the power backplane 6008 extends from the header module 6002 through a number of intermediate modules 6004 to a most bottom, or farthest, module in the stack. In various aspects, the power backplane 6008 is configured to deliver power to a surgical module 6004 through one or more other surgical modules 6004 that are ahead of it in the stack. The surgical module 6004 receiving power from the header module 6002 can be coupled to a surgical instrument or tool configured to deliver therapeutic energy to a patient.

The primary power domain 6009 is the primary power source for the functional module-specific circuits 6013, 6014, 6015 of the modules 6002, 6004. It consists of a single voltage rail that is provided to every module. In at least one example, a nominal voltage of 60V can be selected to be higher than the local rails needed by any module, so that the modules can exclusively implement buck regulation, which is generally more efficient than boost regulation.

In various aspects, the primary power domain 6009 is controlled by the header module 6002. In certain instances, as illustrated in FIG. 20, a local power switch 6018 is positioned on the header module 6002. In certain instances, a remote on/off interface 6016 can be configured to control a system power control 6017 on the header module 6002, for example. In at least one example, the remote on/off interface 6016 is configured to transmit pulsed discrete commands (separate commands for On and Off) and a power status telemetry signal. In various instances, the primary power domain 6009 is configured to distribute power to all the modules in the stack configuration following a user-initiated power-up.

Figure 21:
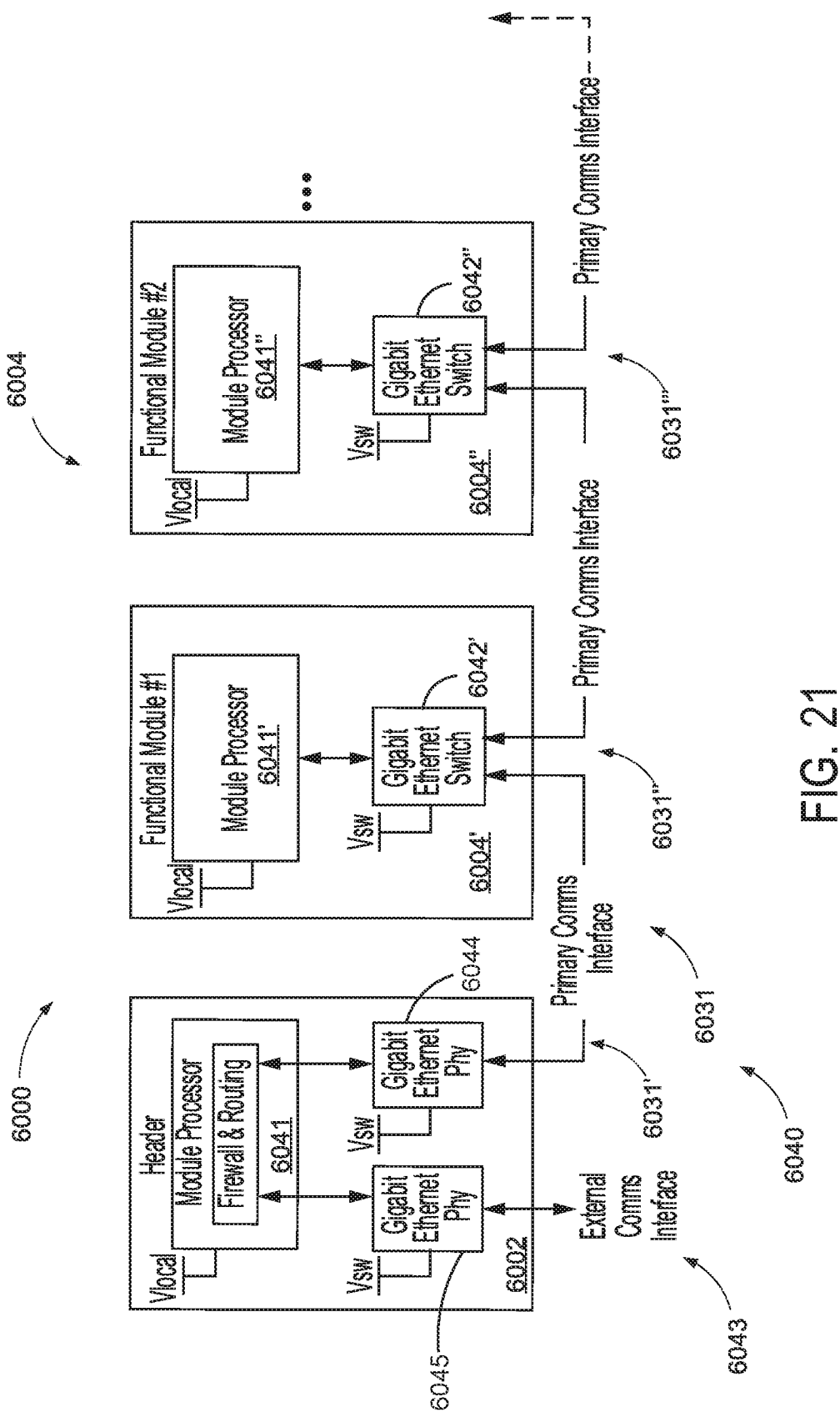
FIG. 21 is a schematic diagram of a modular energy system, in accordance with at least one aspect of the present disclosure.

In various aspects, as illustrated in FIG. 21, the modules of the modular energy system 6000 can be communicably coupled to the header module 6002 and/or to each other via a communication (Serial bus/Ethernet) interface 6040 such that data or other information is shared by and between the modules of which the modular energy system is constructed. An Ethernet switch domain 6013 can be derived from the primary power domain 6009, for example. The Ethernet switch power domain 6013 is segregated into a separate power domain, which is configured to power Ethernet switches within each of the modules in the stack configuration, so that the primary communications interface 6040 will remain alive when local power to a module is removed. In at least one example, the primary communication interface 6040 comprises a 1000BASE-T Ethernet network, where each module represents a node on the network, and each module downstream from the header module 6002 contains a 3-port Ethernet switch for routing traffic to the local module or passing the data up or downstream as appropriate.

Furthermore, in certain examples, the modular energy system 6000 includes secondary, low speed, communication interface between modules for critical, power related functions including module power sequencing and module power status. The secondary communications interface can, for example, be a multi-drop Local Interconnect Network (LIN), where the header module is the master and all downstream modules are slaves.

In various aspects, as illustrated in FIG. 20, a standby power domain 6010 is a separate output from the AC/DC power supply 6003 that is always live when the supply is connected to mains power 6020. The standby power domain 6010 is used by all the modules in the system to power circuitry for a mitigated communications interface, and to control the local power to each module. Further, the standby power domain 6010 is configured to provide power to circuitry that is critical in a standby mode such as, for example, on/off command detection, status LEDs, secondary communication bus, etc.

In various aspects, as illustrated in FIG. 20, the individual surgical modules 6004 lack independent power supplies and, as such, rely on the header module 6002 to supply power in the stack configuration. Only the header module 6002 is directly connected to the mains power 6020. The surgical modules 6004 lack direct connections to the mains power 6020, and can receive power only in the stack configuration. This arrangement improves the safety of the individual surgical modules 6004, and reduces the overall footprint of the modular energy system 6000. This arrangement further reduces the number of cords required for proper operation of the modular energy system 6000, which can reduce clutter and footprint in the operating room.

Accordingly, a surgical instrument connected to surgical modules 6004 of a modular energy system 6000, in the stack configuration, receives therapeutic energy for tissue treatment that is generated by the surgical module 6004 from power delivered to the surgical module 6004 from the AC/DC power supply 6003 of the header module 6002.

In at least one example, while a header module 6002 is assembled in a stack configuration with a first surgical module 6004', energy can flow from the AC/DC power supply 6003 to the first surgical module 6004'. Further, while a header module 6002 is assembled in a stack configuration with a first surgical module 6004' (connected to the header module 6002) and a second surgical module 6004" (connected to the first surgical module 6004'), energy can flow from the AC/DC power supply 6003 to the second surgical module 6004" through the first surgical module 6004'.

The energy generated by the AC/DC power supply 6003 of the header module 6002 is transmitted through a segmented power backplane 6008 defined through the modular energy system 6000. In the example of FIG. 20, the header module 6002 houses a power backplane segment 6008', the first surgical module 6004' houses a power backplane segment 6008", and the second surgical module 6004" houses a power backplane segment 6008'". The power backplane segment 6008' is detachably coupled to the power backplane segment 6008" in the stack configuration. Further, the power backplane segment 6008" is detachably coupled to the power backplane segment 6008'" in the stack configuration. Accordingly, energy flows from the AC/DC power supply 6003 to the power backplane segment 6008', then to the power backplane segment 6008", and then to the power backplane segment 6008'".

In the example of FIG. 20, the power backplane segment 6008' is detachably connected to the power backplane segment 6008" via pass-through hub connectors 6005, 6006 in the stack configuration. Further, the power backplane segment 6008" is detachably connected to the power backplane segment 6008'" via pass-through hub connectors 6025, 6056 in the stack configuration. In certain instances, removing a surgical module from the stack configuration severs its connection to the power supply 6003. For example, separating the second surgical module 6004" from the first surgical module 6004' disconnects the power backplane segment 6008'" from the power backplane segment 6008". However, the connection between the power backplane segment 6008" and the power backplane segment 6008'" remains intact as long as the header module 6002 and the first surgical module 6004' remain in the stack configuration. Accordingly, energy can still flow to the first surgical module 6004' after disconnecting the second surgical module 6004" through the connection between the header module 6002 and the first surgical module 6004'. Separating connected modules can be achieved, in certain instances, by simply pulling the surgical modules 6004 apart.

In the example of FIG. 20, each of the modules 6002, 6004 includes a mitigated module control 6023. The mitigated module controls 6023 are coupled to corresponding local power regulation modules 6024 that are configured to regulate power based on input from the mitigated module controls 6023. In certain aspects, the mitigated module controls 6023 allow the header module 6002 to independently control the local power regulation modules 6024.

The modular energy system 6000 further includes a mitigated communications interface 6021 that includes a segmented communication backplane 6027 extending between the mitigated module controls 6023. The segmented communication backplane 6027 is similar in many respects to the segmented power backplane 6008. Mitigated Communication between the mitigated module controls 6023 of the header module 6002 and the surgical modules 6004 can be achieved through the segmented communication backplane 6027 defined through the modular energy system 6000. In the example of FIG. 20, the header module 6002 houses a communication backplane segment 6027', the first surgical module 6004' houses a communication backplane segment 6027", and the second surgical module 6004" houses a communication backplane segment 6027'". The communication backplane segment 6027' is detachably coupled to the communication backplane segment 6027" in the stack configuration via the pass-through hub connectors 6005, 6006. Further, the communication backplane 6027" is detachably coupled to the communication backplane segment 6027'" in the stack configuration via the pass-through hub connectors 6025, 6026.

Although the example of FIG. 20 depicts a modular energy system 6000 includes a header module 6002 and two surgical modules 6004' 6004", this is not limiting. Modular energy systems with more or less surgical modules are contemplated by the present disclosure. In some aspects, the modular energy system 6000 includes other modules such as, for example, the communications module 3032 (FIG. 15). In some aspects, the header module 6502 supports a display screen such as, for example, the display 2006 (FIG. 7A) that renders a GUI such as, for example, the GUI 2008 for relaying information regarding the modules connected to the header module 6002. As described in greater detail in connection with the example of FIG. 15, in some aspects, the GUI 2008 of the display screen 2006 can provide a consolidated point of control all of the modules making up the particular configuration of a modular energy system.

FIG. 21 depicts a simplified schematic diagram of the modular energy system 6000, which illustrates a primary communications interface 6040 between the header module 6002 and the surgical modules 6004. The primary communications interface 6040 communicably connects module processors 6041, 6041', 6041" of the header module 6002 and the surgical modules 6004. Commands generated by the module processor 6041 of the header module are transmitted downstream to a desired functional surgical module via the primary communications interface 6040. In certain instances, the primary communications interface 6040 is configured to establish a two-way communication pathway between neighboring modules. In other instances, the primary communications interface 6040 is configured to establish a one-way communication pathway between neighboring modules.

Furthermore, the primary communications interface 6040 includes a segmented communication backplane 6031, which is similar in many respects to the segmented power backplane 6008. Communication between the header module 6002 and the surgical modules 6004 can be achieved through the segmented communication backplane 6031 defined through the modular energy system 6000. In the example of FIG. 21, the header module 6002 houses a communication backplane segment 6031', the first surgical module 6004' houses a communication backplane segment 6031", and the second surgical module 6004" houses a communication backplane segment 6031'". The communication backplane segment 6031' is detachably coupled to the communication backplane segment 6031" in the stack configuration via the pass-through hub connectors 6005, 6006. Further, the communication backplane 6031" is detachably coupled to the communication backplane segment 6031" in the stack configuration via the pass-through hub connectors 6025, 6026.

In at least one example, as illustrated in FIG. 21, the primary communications interface 6040 is implemented using the DDS framework running on a Gigabit Ethernet interface. The module processors 6041, 6041', 6041" are connected to Gigabit Ethernet Phy 6044, and Gigabit Ethernet Switches 6042', 6042". In the example of FIG. 21, the segmented communication backplane 6031 connects the Gigabit Ethernet Phy 6044 and the Gigabit Ethernet Switches 6042 of the neighboring modules.

In various aspects, as illustrated in FIG. 21, the header module 6002 includes a separate Gigabit Ethernet Phy 6045 for an external communications interface 6043 with the processor module 6041 of the header module 6002. In at least one example, the processor module 6041 of the header module 6002 handles firewalls and information routing.

Referring to FIG. 20, the AC/DC power supply 6003 may provide an AC Status signal 6011 that indicates a loss of AC power supplied by the AC/DC power supply 6003. The AC status signal 6011 can be provided to all the modules of the modular energy system 6000 via the segmented power backplane 6008 to allow each module as much time as possible for a graceful shutdown, before primary output power is lost. The AC status signal 6011 is received by the module specific circuits 6013, 6014, 6015, for example. In various examples, the system power control 6017 can be configured to detect AC power loss. In at least one example, the AC power loss is detected via one or more suitable sensors.

Referring to FIGS. 20 and 21, to ensure that a local power failure in one of the modules of the modular energy system 6000 does not disable the entire power bus, the primary power input to all modules can be fused or a similar method of current limiting can be used (e-fuse, circuit breaker, etc.). Further, Ethernet switch power is segregated into a separate power domain 6013 so that the primary communications interface 6040 remains alive when local power to a module is removed. In other words, primary power can be removed and/or diverted from a surgical module without losing its ability to communicate with other surgical modules 6004 and/or the header module 6002.

Modular Energy System with Dual Amplifiers and Techniques for Updating Parameters Thereof Having described a general implementation the header and modules of modular energy systems 2000, 3000, 6000, and various surgical instruments usable therewith, for example, surgical instruments 2204, 2206, and 2208, the disclosure now turns to describe various aspects of modular energy systems comprising dual amplifiers and techniques for updating parameters thereof. In other aspects, these modular energy systems are substantially similar to the modular energy system 2000, the modular energy system 3000, and/or the modular energy system 6000 described hereinabove. For the sake of brevity, various details of the other modular energy systems being described in the following sections, which are similar to the modular energy system 2000, the modular energy system 3000, and/or the modular energy system 6000, are not repeated herein. Any aspect of the other modular energy systems described below can be brought into the modular energy system 2000, the modular energy system 3000, or the modular energy system 6000.

As described hereinbelow with reference to FIGS. 22-29, in various aspects, the present disclosure provides modular energy systems 2000, 3000, 6000 comprising dual amplifiers and techniques for updating parameters thereof.

Dual Amplifier Techniques

In various aspects, the present disclosure provides a modular energy system comprising an energy module that includes multiple power amplifiers to deliver different levels of power to the output of the energy module. By way of example and not limitation, high power high efficiency switch-mode/flyback generators do not provide as many power levels to adjust the waveform shape and frequency content as a linear amplifier. In low power output applications, a wideband, linear bipolar amplifier, or similar amplifier, may be employed to drive the output load of the generator. Low power outputs are preferably in the range of 1 to 60 watts; more preferably in the range of 1 to 50 watts; and still more preferably in the range of 1 to 40 watts. Nominally, a low power output is about 35 watts. In high power output applications, a resonant, non-linear switch-mode/flyback type amplifier may be employed to drive the output load of the generator. High power outputs are preferably in the range of 20 to 400 watts; more preferably in the range of 20 to 350 watts; and still more preferably in the range of 41 to 300 watts. Nominally, a high power output is about 150 watts. In accordance with one aspect of the present disclosure, an energy module may employ a linear amplifier to drive a low power load coupled to the output of the energy module and a non-linear power amplifier to drive a high power load coupled to the output of the energy module. In this manner, the energy module can produce a 150 watt output with manageable heat and within a predetermined power budget. For low power settings, a lower efficiency power amplifier can still be within the power and heat requirements of the energy module, and can provide additional wave shaping capabilities.

In one aspect of the present disclosure, the switchover from the low power amplifier to the high power amplifier can be seamless to the user. In another aspect, a user interface may indicate to the user which power amplifier circuit is in use by the energy module and in another aspect may enable the user to select the power amplifier circuit for a predetermined electrosurgical instrument connected to a port of the energy module that uses monopolar. Options include using a resonant power amplifier (e.g., non-linear power amplifier) for all power levels, or employ a wideband power amplifier (e.g., linear power amplifier) to drive lower power ranges and the resonant power amplifier to drive high power ranges. In one aspect, the hardware implementation of the wideband or resonant power amplifiers (e.g., circuits, relays) may be enabled and optimized in the field via software updates anytime.

In one aspect, the present disclosure provides dual power amplifier techniques and methods to resolve the issue of delivering highly refined waveforms in a majority of surgery use cases and delivering high power in a minority of surgery use cases with high efficiency as may be required by the modular energy system 2000, 3000, 6000 thermal and power budget. High power combined with low efficiency can produce excessive heat or exceed the limits of the energy module 2004, 3004, 6004, which is why the higher power levels should be delivered from higher efficiency power amplifier circuits, which provide the benefit of higher energy efficiency, lower cost, and smaller size (e.g. volume, weight, and space occupied on a printed circuit board assembly). Lower efficiency power amplifier circuits include benefits such as greater control over wave shape and making faster and more accurate changes to the output signal. Most surgical tasks are performed with low power settings, so this approach covers the typical uses well.

The combination of high power and low efficiency in a power amplifier can produce excessive heat or exceed the limits of the energy module 2004, 3004, 6004. Therefore, according to various aspect of the present disclosure, higher power is delivered by a higher efficiency power amplifier circuit with the tradeoff of providing less control over wave shape whereas lower efficiency power amplifier circuits can be used to deliver lower power with the advantage of providing more control over wave shape. As shown in FIGS. 22, 23, 27, 28, 29 in one aspect, the present disclosure provides modular energy systems 1000, 1100, 1190, 1193, 1196 comprising energy modules 1004, 1104, 1191, 1194, 1197 configured to deliver highly refined waveforms in low power applications and high efficiency in high power applications as may be required for system thermal and power budget. In one implementation, the energy modules 1004, 1104, 1191, 1194, 1197 are configured to employ at least two power amplifiers and selecting a power amplifier based on the required output power to be produced into a load coupled to the energy modules 1004, 1104, 1191, 1194, 1197. The at least two power amplifiers may be selected by switches, such as relays, or selected using internal chip select features of integrated power amplifiers, among other suitable techniques as may be appreciated by those skilled in the art.

It can be appreciated, that there can be other tradeoffs in the selection of power amplifier circuits for the energy modules 1004, 1104, 1191, 1194, 1197 besides efficiency. For example, cost of components to realize a power amplifier circuit providing greater control of waveshapes and being capable of producing high power output in a load may be prohibitive. For example, the total cost of providing at least two power amplifier circuits described hereinbelow with respect to FIGS. 22, 23, 27, 28, 29 can be lower than the cost of using a single low power amplifier circuit modified to produce high power in the load. According to various aspects, the present disclosure provides a first power amplifier having greater control over wave shape for low power applications and a second power amplifier having less control over wave shape for high power applications may be implemented with moderate cost. The dual amplifier technique described herein provides at least a cost advantage, among other advantages, over a single amplifier technique that provides greater control over wave shape for low and high power applications, but at a prohibitively high cost, among other disadvantages.

Figure 22:
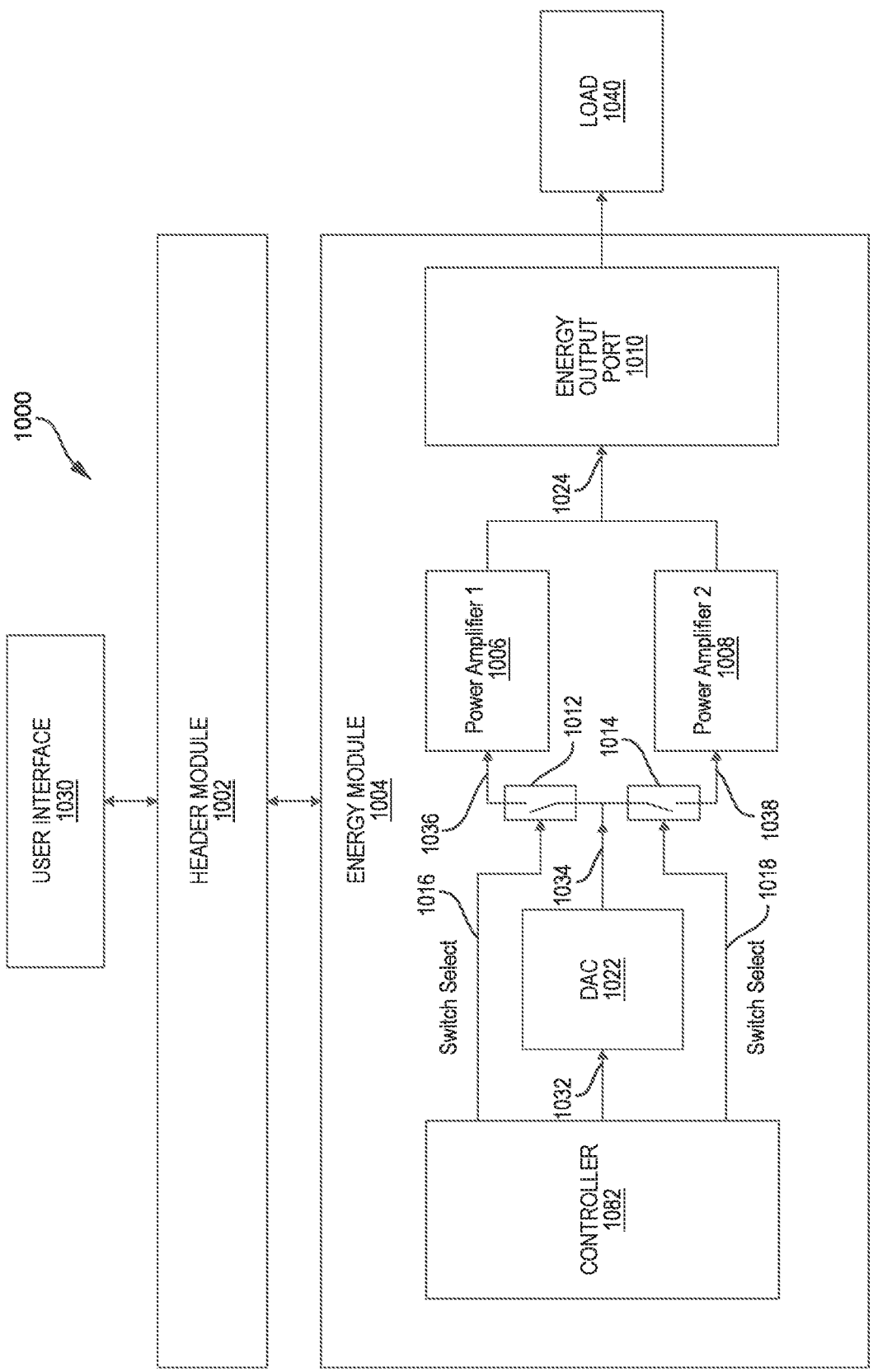
FIG. 22 is a diagram of a modular energy system comprising an energy module with dual power amplifiers, in accordance with at least one aspect of the present disclosure.
Figure 25:
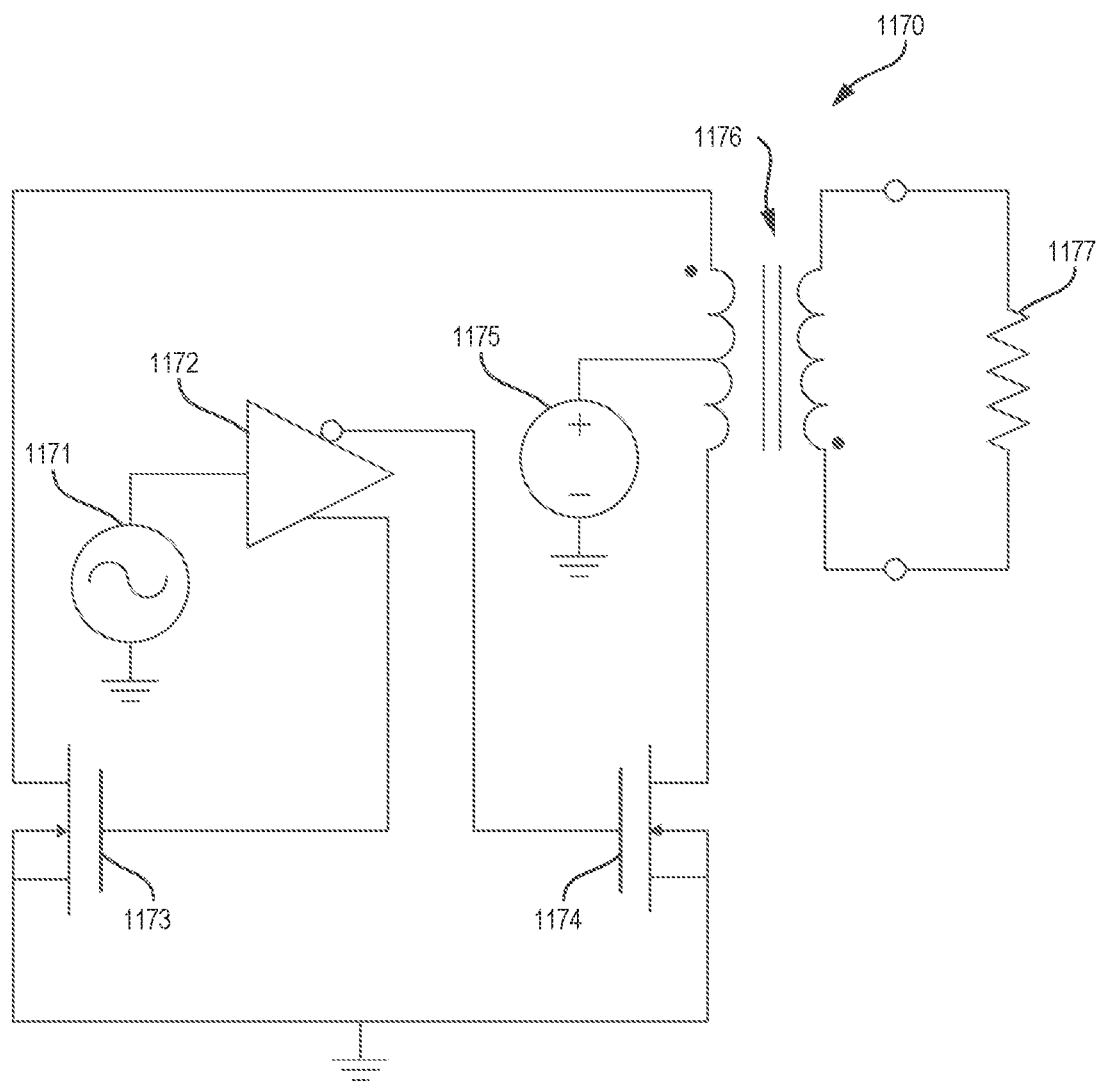
FIG. 25 is a schematic diagram of a power amplifier circuit, in accordance with at least one aspect of the present disclosure.
Figure 26:
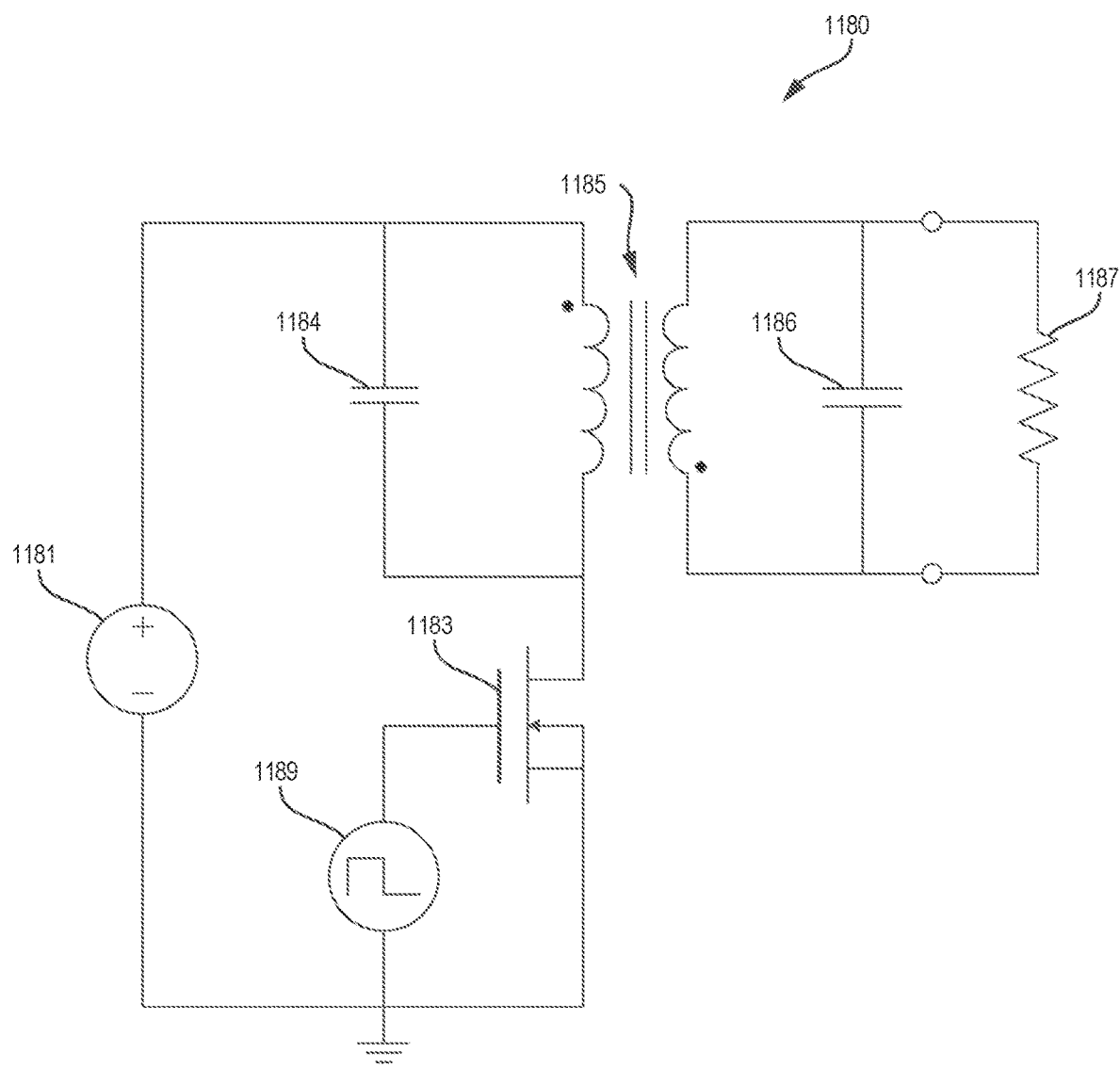
FIG. 26 is a schematic diagram of a power amplifier circuit, in accordance with at least one aspect of the present disclosure.

Turning now to FIG. 22, there is shown a diagram of a modular energy system 1000 comprising an energy module 1002 with dual power amplifiers, in accordance with at least one aspect of the present disclosure. In some respects, the modular energy system 1002 is similar to the modular energy systems 2000, 3000, 6000 described hereinabove. The header module 1002 of the modular energy system 1000 shown in FIG. 22, however, is coupled to an energy module 1004 comprising dual power amplifier circuits 1006, 1008 as explained in the following description. In one aspect, the first amplifier circuit 1006 may be characterized as having a first power rating and the second amplifier circuit 1008 may be characterized as having a second power rating. In one aspect, the second power rating is greater than the first power rating. The first or second power amplifier circuits 1006, 1008 may be selected by a controller 1082 based on a desired power gain that is in the range of the power rating of the first or second power amplifier circuit 1006, 1008. In one aspect, the first power amplifier circuit 1006 can produce up to about 50 watts into a load 1040 coupled to the energy output port 1010 and in one aspect, the second power amplifier 1008 can produce from about 50 to about 150 watts into a load 1040 coupled to the energy circuit output port 1010 of the energy module 1004. In one aspect, the first power amplifier circuit 1006 may be a wideband (e.g., linear) power amplifier circuit as shown in FIG. 25, for example, and the second power amplifier circuit 1008 may be a resonant (e.g., non-linear) power amplifier circuit as shown in FIG. 26, for example.

The energy module 1004 includes a controller 1082 configured to control various communications and processing functions of the energy module 1004 and to generate a digital signal waveform representation of the analog signal waveform to be applied to the load 1040. The energy module 1004 can include a first power amplifier circuit 1006 and a second power amplifier circuit 1008, among various configurations of power amplifier circuits. In various aspects, the first power amplifier circuit 1006 may be a wideband (e.g., linear class) RF power amplifier circuit and the second power amplifier circuit 1008 may be a resonant (non-linear switch mode/flyback) RF power amplifier circuit such as, for example, a flyback modulated switching RF power amplifier circuit. Although the energy module 1004 shown in the example of FIG. 22 comprises two power amplifier circuits 1006, 1008, it is contemplated within the scope of the present disclosure that more than two power amplifier circuits 1006, 1008 may be employed to accommodate a variety of output power levels and efficiencies to deliver low power with highly refined waveforms in low energy surgery use cases and high power with high efficiency to mitigate predetermined thermal and power budgets of the modular energy system 1000 in high energy surgery use cases.

In one aspect, the controller 1082 is electrically connected to a first switch 1012, which can be actuated and de-actuated by a first switch select signal 1016 controlled by the controller 1082. The first switch 1012 is disposed between the controller 1082 and the first power amplifier circuit 1006. In one aspect, the first switch 1012 couples the output of a digital-to-analog converter 1022 (DAC) to the analog input of the first power amplifier circuit 1006 when the first switch 1012 is activated ON as controlled by the first switch select signal 1016.

The controller 1082 is electrically connected to a second switch 1004, which can be actuated and de-actuated by a second switch select signal 1018. The second switch 1014 is disposed between the controller 1082 and the second power amplifier circuit 1008. In one aspect, the second switch 1014 may couple the output of the DAC 1022 to the input of the second power amplifier circuit 1008 when the second switch 1014 is activated ON as controlled by the second switch select signal 1018. In other aspects, as explained in the description of FIG. 26, a switching signal from the controller 1082 (or other microcontroller, computer, digital signal processor, digital timing circuit) may be applied to the input of the second power amplifier circuit 1008.

Those skilled in the art will appreciate that the first switch 1012 may be implemented as a RF selection relay controlled by the first switch select signal 1016 provided by the controller 1082. Similarly, those skilled in the art will appreciate that the second switch 1014 also may be implemented as a RF selection relay controlled by the second switch select signal 1018 provided by the controller 1082. It should be noted that when the first switch 1012 is ON, the second switch 1014 is OFF such when the analog signal at the analog output 1034 of the DAC 1022 is coupled to the input 1036 of the first power amplifier circuit 1006, the input 1038 of the second power amplifier circuit 1008 is open. Conversely, when the second switch 1014 is ON, the first switch 1012 is OFF such that when the analog signal at the analog output 1034 of the DAC 1022 is coupled to the input 1038 of the second power amplifier circuit 1008, the input 1036 of the first power amplifier circuit 1006 is open. In the example shown in FIG. 22, both switches 1012, 1014 can be in the OFF state at the same time, but both switches 1012, 1014, cannot be in the ON state at the same time. It is contemplated, however, that in other aspects of the present disclosure, the circuitry may be adapted and configured to enable power blending between the first and second power amplifier circuits 1006, 1008.

In one aspect, the controller 1082 of the energy module 1004 may be implemented as a microcontroller, computer, digital timing circuit, or a digital signal processor (DSP) via a direct digital synthesizer (DDS), for example. The DDS can either be embedded in the DSP or implemented in a field-programmable gate array (FPGA), for example. For example, in one aspect, the controller 1082 is configured to apply a digital waveform to the digital input 1032 of the DAC 1002 and the analog signal at the analog output 1034 of the DAC 1022 to the input of either the first or second power amplifier circuits 1006, 1008 as may be selected by the controller 1082. In one aspect, the controller 1082 is further configured to determine the waveshape in digital form, input impedance (Z), current (I), power (P), voltage (V), and frequency (f) of the desired output signal 1024 of the energy module 1004 to be applied to the load 1040. The DAC 1022 converts the digital signal waveform segments to an analog signal that is amplified by the first or second power amplifier circuit 1006, 1008 based on the switch select signals 1016, 1018 selected by the controller 1082. The amplified signal waveform produced at the output 1024 of the first or second power amplifier circuit 1006, 1008 is applied to a load 1040 coupled to the energy output port 1010 of the energy module 1004. The controller 1082 is configured to define the digital waveform in the software based on various parameters such, for example, curve shape, input impedance (Z), current limit (i), power limit (p), voltage limit (v), and frequency (f). The shape of the signal waveform produced at the output 1024 of the first or second power amplifier circuit 1006, 1008 may be defined by multiple segments that may be loaded by the software to generate a plurality of suitable waveshapes.

Prior to loading the digital waveform segments to the digital input 1032 of the DAC 1022, the controller 1082 selects either the first or second power amplifier circuit 1006, 1008 by selecting the corresponding first or second amplifier switch select signal 1016, 1018 to amplify the analog signal at the analog output 1034 of the DAC 1022. Once the characteristics of the output signal 1024 is determined by the controller 1082, such as waveshape, impedance (Z), current (I), power (P), voltage (V), and frequency (f), the controller 1082 selects either the first or second power amplifier circuit 1006, 1008 and then loads the digital signal to the digital input 1032 of the DAC 1022.

In one aspect, the energy output port 1010 of the energy module 1004 provides the amplified output 1024 from the first power amplifier circuit 1006. In another aspect, the energy output 1010 of the energy module 1004 is the amplified output 1024 from the second power amplifier circuit 1008. For example, the energy output port 1010 of the energy module 1004 provides the amplified output 1024 of the first or second power amplifier circuit 1006, 1008 selected by the controller 1082 or selected by a user via the user interface 1030.

Figure 23:
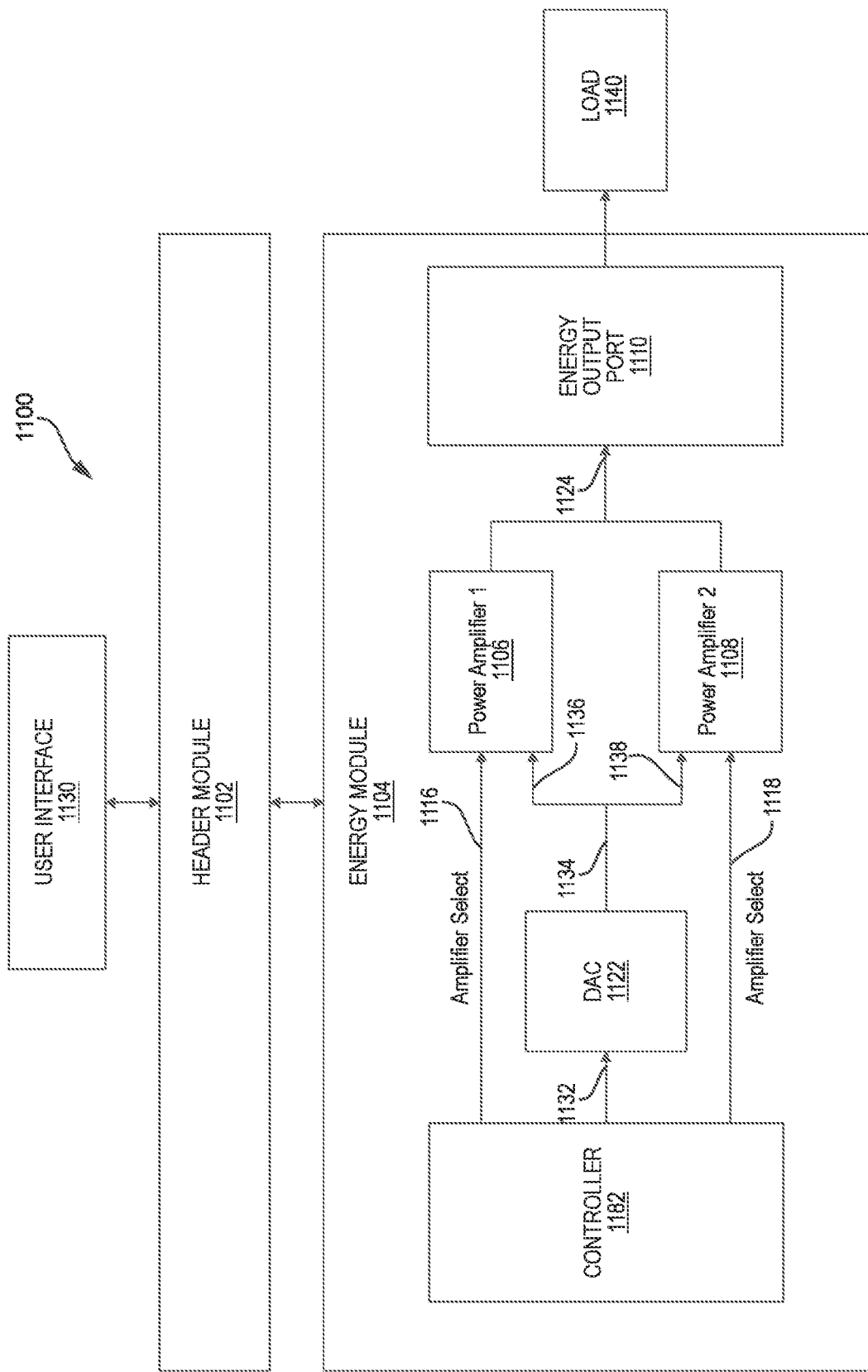
FIG. 23 is a diagram of a modular energy system comprising an energy module with dual power amplifiers, in accordance with at least one aspect of the present disclosure.

FIG. 23 is a diagram of a modular energy system 1100 with dual power amplifiers, in accordance with at least one aspect of the present disclosure. In some respects, the modular energy system 1002 is similar to the modular energy systems 1000, 2000, 3000, 6000 described hereinabove. The header module 1102 of the modular energy system 1100 shown in FIG. 23, however, is coupled to an energy module 1104 comprising dual power amplifiers 1106, 1108 as explained in the following description. The energy module 1104 includes a controller 1182 configured to control various communications and processing functions of the energy module 1104 and to generate a digital signal waveform representation of the analog signal waveform to be applied to a load 1140 coupled to the energy output port 1110 of the energy module 1104. The energy module 1104 can include a first power amplifier circuit 1106 and a second power amplifier circuit 1108, among various configurations of power amplifier circuits. In one aspect, the first power amplifier circuit 1106 may be characterized as having a first power rating and the second power amplifier circuit 1108 may be characterized as having a second power rating. In one aspect, the second power rating is greater than the first power rating. The first or second power amplifier circuit 1106, 1108 may be selected by a controller 1182 based on a desired power gain that is in the range of the power rating of the first or second power amplifier circuit 1106, 1108. In one aspect, the first power amplifier circuit 1106 can produce up to about 50 watts into a load 1140 coupled to the energy output port 1110 and in one aspect, the second power amplifier circuit 1108 can produce from about 50 to about 150 watts into a load 1140 coupled to the energy output port 1110 of the energy module 1104. In one aspect, the first power amplifier circuit 1106 may be a wideband (e.g., linear) power amplifier circuit as shown in FIG. 25, for example, and the second power amplifier circuit 1108 may be a resonant (e.g., non-linear) power amplifier circuit as shown in FIG. 26.

The energy module 1104 includes a controller 1182 configured to control various communications and processing functions of the energy module 1104 and to generate a digital signal waveform representation of the analog signal waveform to be applied to the load 1140. The energy module 1104 can include a first power amplifier circuit 1106 and a second power amplifier circuit 1108, among various configurations of power amplifier circuits. In various aspects, the first power amplifier circuit 1106 may be a wideband (e.g., linear class) RF power amplifier circuit and the second power amplifier circuit 1108 may be a resonant (non-linear switch mode/flyback) RF power amplifier circuit such as, for example, a flyback modulated switching RF power amplifier circuit. Although the energy module 1104 shown in the example of FIG. 23 comprises two power amplifier circuits 1106, 1108, it is contemplated within the scope of the present disclosure that more than two power amplifier circuits 1106, 1108 may be employed to accommodate a variety of output power levels and efficiencies to deliver low power with highly refined waveforms in low energy surgery use cases and high power with high efficiency to mitigate predetermined thermal and power budgets of the modular energy system 1100 in high energy surgery use cases.

In one aspect, the controller 1182 is electrically connected to a first power amplifier circuit 1106 that may be selected by a first amplifier select signal 1116 by the controller 1182. The controller 1182 also is electrically connected to a second power amplifier circuit 1108 that may be selected by a second amplifier select signal 1118 by the controller 1182. In this manner, the controller 1182 may select the first or second power amplifier circuit 1106, 1108 prior to outputting a digital waveform to the digital input 1132 of the DAC 1122.

In one aspect, the energy module 1104 comprises a DAC 1122 electrically coupled to the controller 1182. The analog signal at the analog output 1134 of the DAC 1122 is applied to the input 1136 of the first power amplifier circuit 1106 and, in one aspect, may be applied to the input 1138 of the second power amplifier circuit 1108. In other aspects, as explained in the description of FIG. 26, a switching signal from the controller 1182 (or other microcontroller, computer, digital signal processor, digital timing circuit) may be applied to the input of the second power amplifier circuit 1108.

In one aspect, the controller 1182 applies a digital signal to the digital input 1132 to the DAC 1122. The digital signal at the digital input 1132 of the DAC 1122 comprises digital output waveform segments defined by waveshape, input impedance (Z), current (I), power (P), voltage (V), and frequency (f) of the desired amplified analog signal at the output 1124 of the first or second power amplifier circuit 1106, 1108 that is applied to the load 1140 coupled to the energy output port 1110. The DAC 1122 converts the digital signal at the digital input 1132 of the DAC 1122 to an analog signal at the output 1134 of the DAC 1122. The analog signal at the output 1134 of the DAC 1122 is applied to the input 1136, 1138 of the first or second power amplifier circuit 1106, 1108 selected by the controller 1182 via the amplifier select signals 1116, 1118. The analog signal waveform delivered to the load 1140 coupled to the output port 1110 of the energy module 1104 may be defined in the controller 1182 software based on various parameters such as curve shape, input impedance (Z), current limit (i), power limit (p), voltage limit (v), and frequency (f). The shape of the output signal waveform may be defined by multiple segments that may be loaded by the controller 1182 software into the digital input 1132 of the DAC 1122 to generate a plurality of suitable analog signal waveshapes at the output 1134 of the DAC 1122.

Prior to loading the digital waveform segments into the digital input 1132 of the DAC 1122, the controller 1182 selects which power amplifier circuit 1106, 1108 to use to amplify the analog signal at the analog output 1134 of the DAC 1122 by power amplifier select signals 1116, 1118. Once the characteristics of the output signal waveform at the output 1124 is determined by the controller 1182, such as waveshape, impedance (Z), current (I), power (P), voltage (V), and frequency (f), the controller 1182 selects either the linear power amplifier 1106 or the non-linear power amplifier 1108 and then loads the digital signal into the digital input 1132 of the DAC 1122.

With reference now to both FIGS. 22, 23, 27, 28, 29, in various aspects, the first power amplifier circuits 1006, 1106 can be configured to drive low power output levels to the load 1040, 1140 coupled to the output port 1010, 1110 of the energy module 1004, 1104. Low power levels are preferably in the range of 1 to 60 watts; more preferably in the range of 1 to 50 watts; and still more preferably in the range of 1 to 40 watts. The first power amplifier circuit 1006, 1106 can be an advanced wideband field effect transistor or bipolar junction transistor amplifier circuit or a similar amplifier. The first power amplifier 1006, 1106 can be a lower efficiency amplifier circuit but may provide greater control over waveshape and is well suited low power output applications. In another aspect, the first power amplifier circuit 1006, 1106 can operate within the power and heat requirements of the energy module 1004, 1104 and the modular energy system 1000, 1100. In addition to delivering low power levels, the first power amplifier circuit 1006, 1106 can be configured to deliver an output signal 1024, 1124 having a variety of waveshapes to the load 1040, 1140 coupled to the energy output port 1010, 1110 of the energy module 1004, 1104.

Still with reference to both FIGS. 22, 23, 27, 28, 29, in various aspects, the second power amplifier circuit 1008, 1108 can be configured to drive high power levels to a load 1040, 1140 coupled to the energy output port 1010, 1110 of the energy module 1004, 1104. High power levels are preferably in the range of 20 to 400 watts; more preferably in the range of 20 to 350 watts; and still more preferably in the range of 41 to 300 watts. The second power amplifier circuit 1008, 1108 can be a high power high efficiency resonant circuit or switch mode/flyback power amplifier circuit. In one aspect, the second power amplifier circuit 1008, 1108 may be configured to deliver high power levels at high efficiency but with less control waveform shape and frequency of the output signal 1024, 1124 supplied at the energy output port 1010, 1110 of the energy module 1004, 1104. The second power amplifier circuit 1008, 1108 can manage heat within the power budget of the energy module 1004, 1104 and the modular energy system 1000, 1100 due to its high efficiency rating.

Still with reference to both FIGS. 22, 23, 27, 28, 29, in various aspects, the controller 1082, 1182 can be configured to automatically switch between the first power amplifier circuit 1006, 1106 and the second power amplifier circuit 1008, 1108. In various aspects, the controller 1082, 1182 can be configured to switch between the first power amplifier circuit 1006, 1106 and the second power amplifier circuit 1008, 1108 based on user inputs entered via the user interface 1030, 1130 of the header module 1002, 1102 of the modular energy system 1000, 1100.

Still with reference to FIGS. 22, 23, 27, 28, 29, in various aspects, the switchover between the first power amplifier circuit 1006, 1106 and the second power amplifier circuit 1008, 1108 is seamless to the user. In another aspect, the user interface 1030, 1130 coupled to the header module 1002, 1102 may highlight to the user which power amplifier 1006, 1106, 1008, 1108 is currently in use and may enable the user to select one or the or the other power amplifier circuit 1006, 1106, 1008, 1108 based on the type of surgical instrument coupled to the energy output port 1010, 1110 of the energy module 1004, 1104. Such options include, for example, a monopolar RF instrument, a bipolar RF instrument, or a combination ultrasonic/RF instrument (either monopolar or bipolar).

Still with reference to FIGS. 22, 23, 27, 28, 29, the hardware (circuits/relays) implementation of the power amplifier circuits 1006, 1106, 1008, 1108 may be fixed at the manufacturing stage and the configuration of the power amplifier circuits 1006, 1106, 1008, 1108 may be updated in the field to enable and optimize when and how to use each power amplifier circuit 1006, 1106, 1008, 1108 by way of software updates, even after the energy modules 1002, 1104 are sold, shipped, and/or are installed in the field.

Still with reference to FIGS. 22, 23, 27, 28, 29, In another aspect, the software of the modular energy system 1000, 1100 can be updated to refine the energy output based on a particular application. Traditional techniques of updating software on the controller 1082, 1182 required the software to be recompiled, a quality check, and multiple releases of the software due to limited bandwidth. In one aspect of the present disclosure, the software tools for operating the controller 1082, 1182 of the modular energy system 1000, 1100 are configured to convert the models into ".ini" configuration files comprising text-based content as shown in TABLE 1, for example, with a structure and syntax comprising key-value pairs for properties, and sections that organize the properties with all the set points with many iterations and refinements such as, for example, waveshape, input impedance (Input_z), current limit (Limit_i), power limit (Limit_p), and voltage limit (Lmit_v) for each curve segment of the desired output signal 1024, 1124. The validated software is capable of always producing energy within some bounds that are safe and effective. In one aspect, refinements are capable of being made via files that are not the core software, and are updated more quickly than typical firmware upgrades of the energy module 1004, 1104.

TABLE 1

| Software_Setpoint.ini |
| --- |
| [LoadCurveRow01] |
| Input_z = 0
Limit_i = 0.30543
Limit_p = 2.3322
Limit_v = 636 |
| [LoadCurveRow02] |
| Input_z = 25
Limit_i = 0.30543
Limit_p = 2.3322
Limit_v = 636 |
| [LoadCurveRow03] |
| Input_z = 50
Limit_i = 0.30332
Limit_p = 4.6
Limit_v = 636 |
| [LoadCurveRow04] |

TABLE 1-continued

| Software_Setpoint.ini |
| --- |
| Input_z = 75
Limit_i = 2
Limit_p = 4.6
Limit_v = 18.5752
... |

Figure 24:
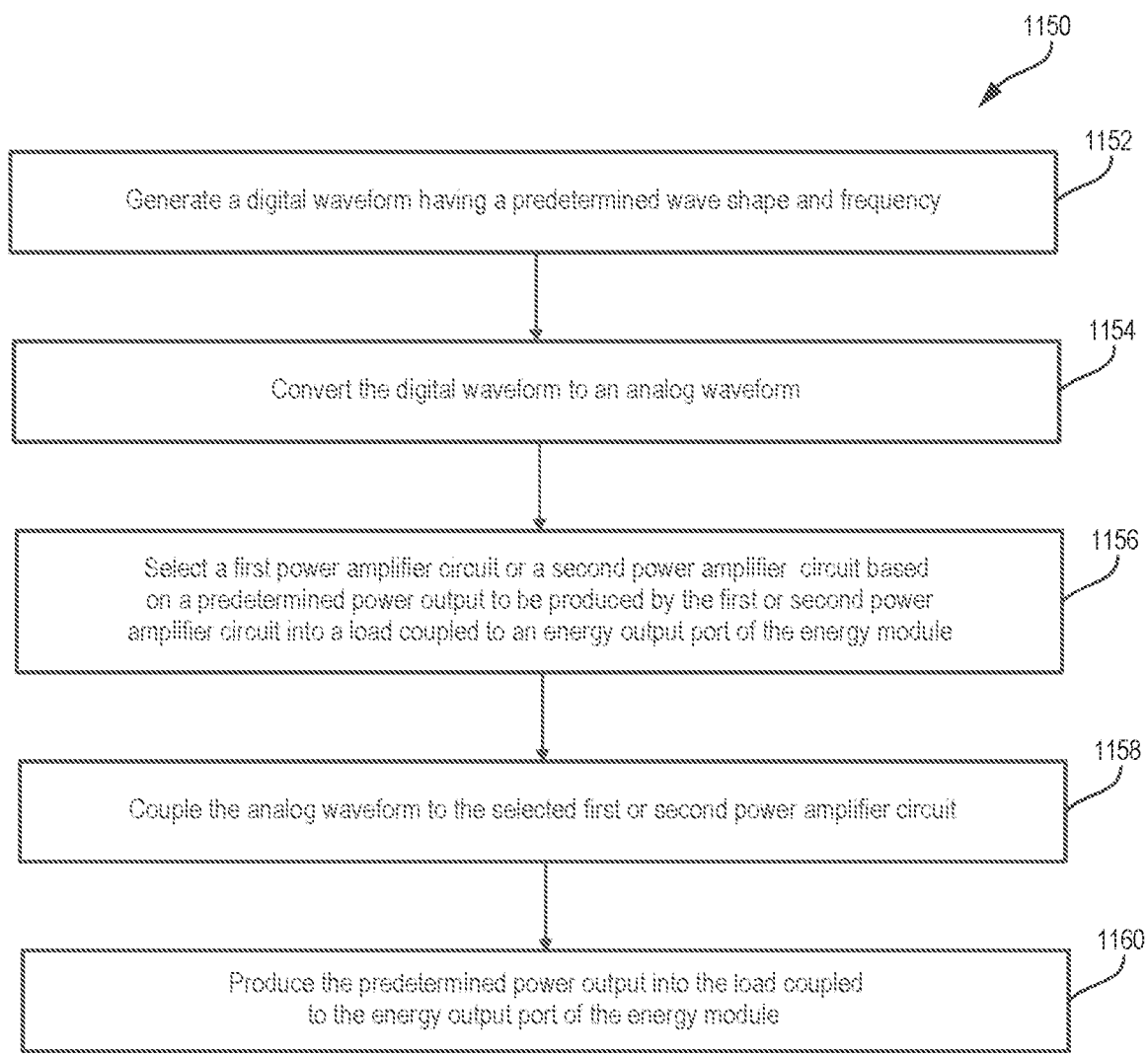
FIG. 24 is a flow diagram of a method of delivering power to a load by an energy module, in accordance with at least one aspect of the present disclosure.

FIG. 24 is a flow diagram of a method 1150 of delivering power to a load 1040, 1140 by an energy module 1000, 1100, in accordance with at least one aspect of the present disclosure. With reference now also to FIGS. 22 and 23, according to the method 1150, the controller 1082, 1182 generates 1152 a digital waveform having a predetermined wave shape and frequency. The controller 1082, 1182 is coupled to the DAC 1022, 1122. The DAC 1022, 1122 converts 1154 the digital waveform to an analog waveform. The controller 1082, 1182 selects 1156 a first power amplifier circuit 1006, 1106 or a second power amplifier circuit 1008, 1108 based on a predetermined power output to be produced by the first power amplifier circuit 1006, 1106 or the second power amplifier circuit 1008, 1108 into a load 1040, 1140 coupled to an energy output port 1010, 1110 of the energy module 1000, 1100. The controller 1082, 1182 couples 1158 the analog waveform to the selected first power amplifier circuit 1006, 1106 or the second power amplifier circuit 1008, 1108. The selected first power amplifier circuit 1006, 1106 or second power amplifier circuit 1008, 1108 produces 1160 the predetermined power output into the load 1040, 1140 coupled to the energy output port 1010, 1110 of the energy module 1000, 1100. In one aspect, the controller 1082, 1182 applies a switching signal to the input of the second amplifier circuit 1008, 1108, as explained in the description of FIG. 26, for example.

With reference back to FIGS. 22 and 24, in accordance with one aspect of the method 1150, the controller 1082 selects a first switch 1012 coupled between the DAC 1022 and the first power amplifier circuit 1006 to produce a first power output into the load 1040 coupled to the output 1024 of the first power amplifier circuit 1006 through the energy output port 1010. Alternatively, the controller 1082 selects a second switch 1014 coupled between the DAC 1022 and the second power amplifier circuit 1008 to produce a second power output into the load 1040 coupled to the output 1024 of the second power amplifier circuit 1008 through the energy output port 1010.

With reference now to FIGS. 23 and 24, in accordance with one aspect of the method 1150, the controller 1182 selects the first power amplifier circuit 1106 via a first amplifier select signal 1116 to produce a first power output into a load 1140 coupled to the output 1124 of the first power amplifier circuit 1106 through the energy output port 1110. Alternatively, the controller 1182 selects the second power amplifier circuit 1108 via a second amplifier select signal 1118 to produce a second power output into the load 1140 coupled to the output 1124 of the second power amplifier circuit 1108 through the energy output port 1110.

With reference to FIGS. 22-24, according to the one aspect of the method 1150, the controller 1082, 1182 determines the load 1040, 1140 coupled to the energy output port 1010, 1110 of the energy module 1000, 1100. The controller 1082, 1182 then generates a waveform having a predetermined wave shape and frequency. The controller 1082, 1182 also limits the current, power, and voltage of the waveform based on the impedance of the load 1040, 1140 coupled to the output 1024 of the first amplifier circuit 1006, 1008 or second power amplifier circuit 1008, 1108 through the energy output port 1010, 1110.

FIG. 25 is a schematic diagram of a power amplifier circuit 1170, in accordance with at least one aspect of the present disclosure. The power amplifier circuit 1170 shown in FIG. 25 is one aspect of a power amplifier 1006, 1106 described above with reference to FIGS. 22 and 23. In the example shown in FIG. 25, the power amplifier circuit 1170 may be employed for low power applications with any combination of these benefits the power amplifier circuit 1180 shown in FIG. 26. Accordingly, the power amplifier circuit 1170 shown in FIG. 25 may be referred to as a wideband power amplifier circuit and provides a more controlled or exact wave shape and can make faster or more accurate changes to the output signal versus the power amplifier circuit 1180 shown in FIG. 26. As previously discussed low power outputs are preferably in the range of 1 to 60 watts; more preferably in the range of 1 to 50 watts; and still more preferably in the range of 1 to 40 watts.

With reference back to FIG. 25, in one aspect, the amplifier circuit 1170 receives an analog signal 1171 from a microcontroller, computer, digital signal processor, digital timing circuit, such as the controller 1082, 1182 shown in FIGS. 22 and 23, passed thru a DAC 1082, 1182 also 1182 shown in FIGS. 22 and 23. The input analog signal 1171 is input into a preamplifier 1172 that outputs the input analog signal 1171 in two polarities; one output signal goes positive up when the other signal goes negative, and vice-versa. The positive going signal, which mirrors the input analog signal 1171 is applied to the input of a first switch 1173 and the negative going signal, which is the inverse of the input analog signal 1171, is applied to a second switch 1174. The switches 1173, 1174 may be selected from a variety of solid state switches such as transistors including, without limitation, field effect transistors, bipolar junction transistors, among others. The switches 1173, 1174 operate as analog switches, where they are intentionally operated partially-on, which causes them to waste energy as heat, but also enables the benefits of the wideband amplifier circuit 1170 described above such as providing a more controlled or exact wave shape and making faster or more accurate changes to the output signal. A power supply 1175 to the amplifier circuit 1170, such as rectified AC voltage, for example, is applied to a transformer 1176, which is coupled to a load 1177, which is a representation of a load, external to the energy module 1004, 1104 as shown in FIGS. 22 and 23, for example. Those skilled in the art will appreciate that the amplifier circuit 1170 is one of many suitable implementations of the first power amplifier 1006, 1106 shown in FIGS. 22 and 23, and thus should be limited in this context.

FIG. 26 is a schematic diagram of a power amplifier circuit 1180, in accordance with at least one aspect of the present disclosure. The power amplifier circuit 1180 shown in FIG. 26 is one aspect of a power amplifier 1008, 1108 described above with reference to FIGS. 22 and 23. In the example shown in FIG. 26, the power amplifier circuit 1180 may be employed for high power applications with any combination of the following benefits versus the amplifier circuit 1170 shown in FIG. 25. Accordingly, the power amplifier circuit 1180 shown in FIG. 26 may be referred to as a resonant circuit and is more energy efficient, more economical, and utilizes less volume, weight, and space on a printed circuit board assembly versus the power amplifier circuit 1170 shown in FIG. 25. As previously discussed, high power outputs are preferably in the range of 20 to 400 watts; more preferably in the range of 20 to 350 watts; and still more preferably in the range of 41 to 300 watts.

With reference now to FIG. 26, in one aspect, the amplifier circuit 1180 comprises a power supply 1181 to the amplifier circuit 1180, which may be rectified AC voltage, for example. A microcontroller, computer, digital signal processor, digital timing circuit, among others, such as the controller 1082, 1182 shown in FIGS. 22 and 23, for example, applies a switching signal 1189 to a switch 1183. With reference back to FIG. 26, the switch 1183, may be selected from a variety of solid state switches such as transistors including, without limitation, field effect transistors, bipolar junction transistors, among others. The amplifier circuit 1180 includes an input capacitance 1184 coupled to the input side of a transformer 1185 and an output capacitance 1186 coupled to the output side of the transformer 1185. The output capacitance 1186 is coupled to a load 1187, which is a representation of a load, external to the energy module 1004, 1104 as shown in FIGS. 22 and 23, for example. Those skilled in the art will appreciate that the amplifier circuit 1180 is one of many suitable implementations of the second power amplifier 1008, 1108 shown in FIGS. 22 and 23, and thus should be limited in this context.

Figure 27:
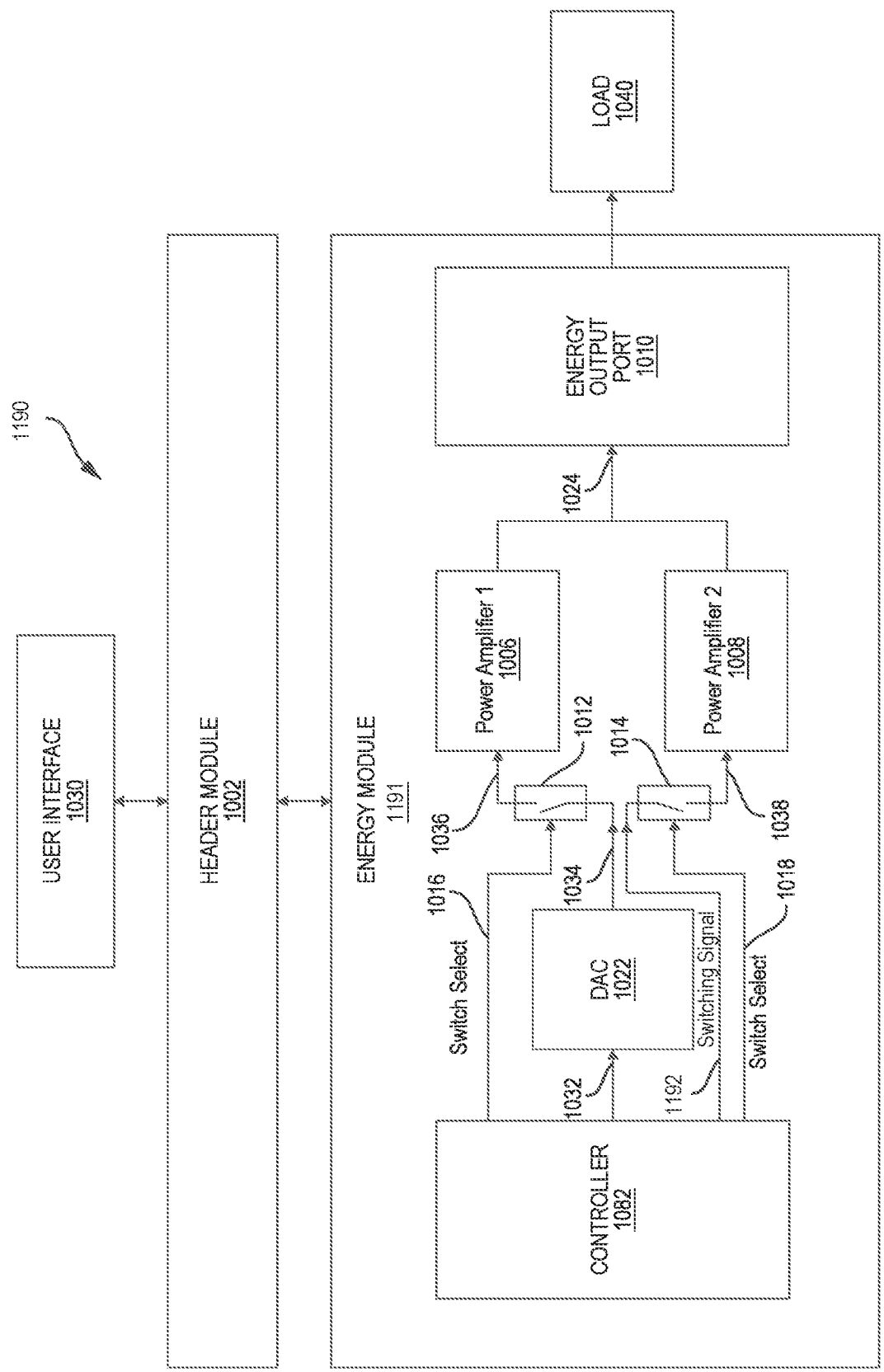
FIG. 27 is a diagram of a modular energy system comprising an energy module with dual power amplifiers, in accordance with at least one aspect of the present disclosure.

FIG. 27 is a diagram of a modular energy system 1190 comprising an energy module 1191 with dual power amplifiers, in accordance with at least one aspect of the present disclosure. As shown, the DAC 1022 is coupled only to the first power amplifier 1006 through the first switch 1012 selectable by the first switch select signal 1016. The second power amplifier circuit 1008 comprises a switching circuit as described in FIG. 26. In the aspect illustrated in FIG. 27, when the controller selects the fir tower amplifier circuit 1006, the DAC 1002 applies the analog signal 1034 to the input 1036 of the first power amplifier circuit 1006. When controller 1082 selects the second power amplifier circuit 1008, the controller 1082 applies a switching signal 1192 the input 1038 of the second power amplifier circuit 1008 through the second switch 1014. The input 1038 is coupled to the switching circuit of the second power amplifier circuit 1108.

Figure 28:
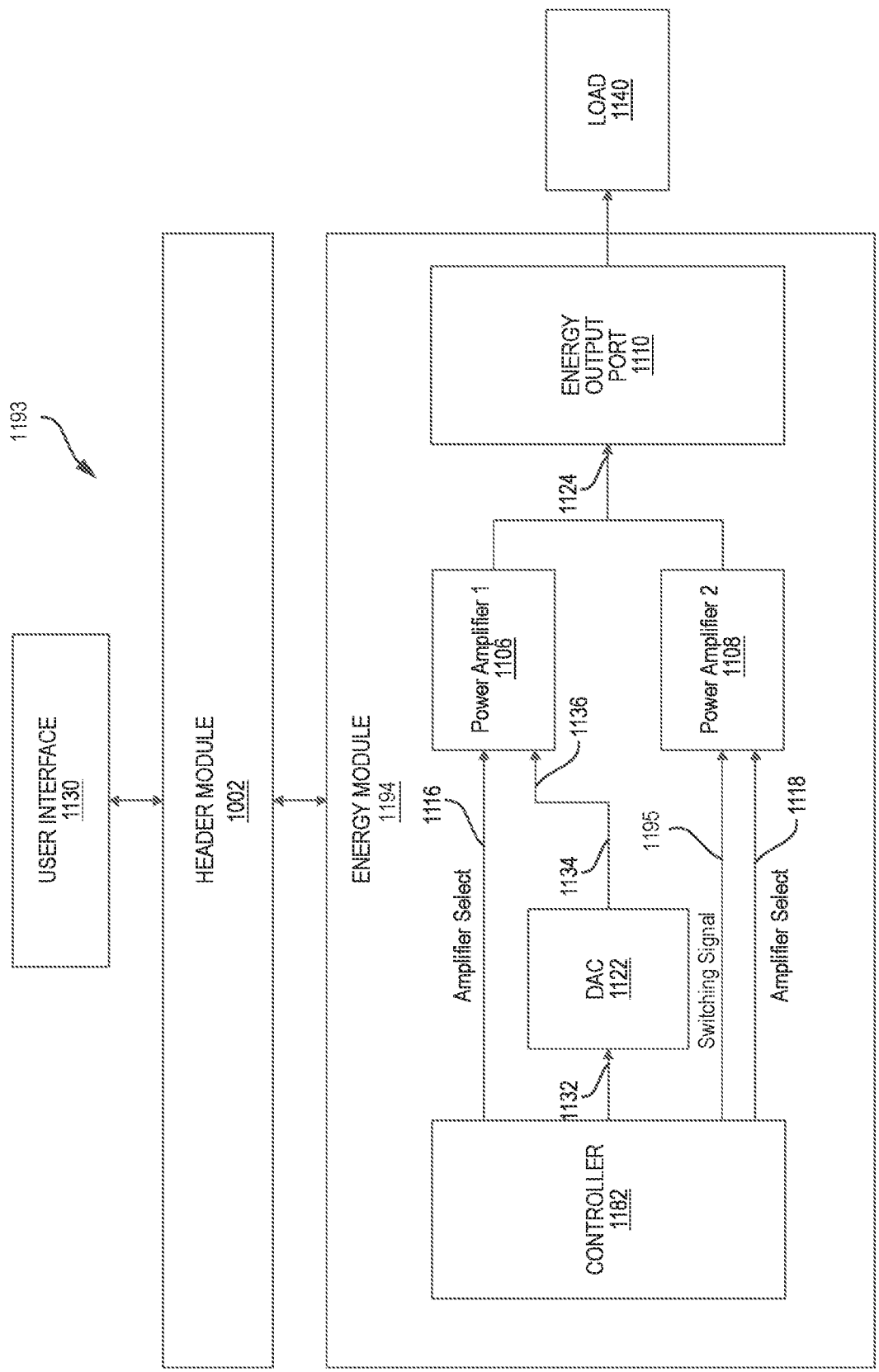
FIG. 28 is a diagram of a modular energy system comprising an energy module with dual power amplifiers, in accordance with at least one aspect of the present disclosure.

FIG. 28 is a diagram of a modular energy system 1193 comprising an energy module 1194 with dual power amplifiers, in accordance with at least one aspect of the present disclosure. As shown, the DAC 1122 is coupled only to the first power amplifier 1106. In one aspect, the controller 1182 is electrically connected to the first power amplifier circuit 1106 that may be selected by the first amplifier select signal 1116 by the controller 1182. The controller 1182 also is electrically connected to the second power amplifier circuit 1108 that may be selected by a second amplifier select signal 1118 by the controller 1182. The second power amplifier circuit 1108 comprises a switching circuit as described in FIG. 26. In the aspect illustrated in FIG. 28, when the controller 1182 selects the first power amplifier circuit 1106, the DAC 1122 applies the analog signal 1134 to the input 1136 of the first power amplifier circuit 1106. When the controller 1182 selects the second power amplifier circuit 1108, the controller 1182 applies a switching signal 1195 to the input of the switching circuit of the second power amplifier circuit 1108.

Figure 29:
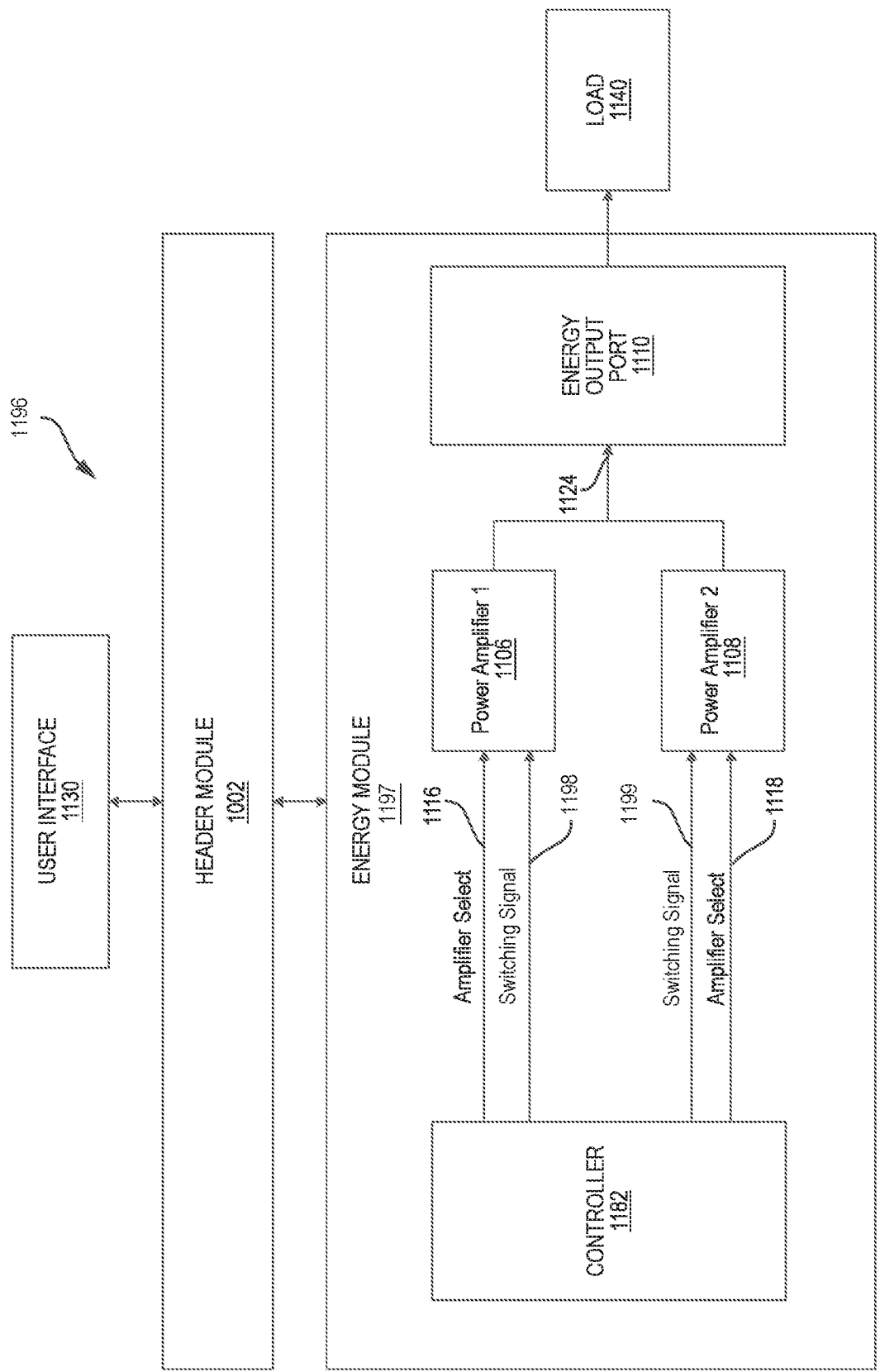
FIG. 29 is a diagram of a modular energy system comprising an energy module with dual power amplifiers, in accordance with at least one aspect of the present disclosure.

FIG. 29 is a diagram of a modular energy system 1196 comprising an energy module 1197 with dual power amplifiers, in accordance with at least one aspect of the present disclosure. In one aspect, the controller 1182 is electrically connected to the first and second power amplifier circuits 1106, 1108. The first and second amplifier circuits 1106, 1108 are selectable by the first and second amplifier select signals 1116, 1118 by the controller 1182. The first and second power amplifier circuits 1106, 1108 each comprise a switching circuit as described in FIG. 26. In the aspect illustrated in FIG. 29, when the controller 1182 selects the first power amplifier 1106, the controller 1182 applies the first switching signal 1198 to the input of the first switching circuit of the first power amplifier circuit 1106. When the controller 1182 selects the second power amplifier circuit 1108, the controller 1182 applies the second switching signal 1199 to the input of the second switching circuit of the second amplifier circuit 1108.

EXAMPLES

Various aspects of a modular energy system comprising dual amplifiers and techniques for updating parameters thereof as described herein with reference to FIGS. 22-29 are set out in the following numbered examples.

Example 1. An energy module, comprising: a controller; a first power amplifier circuit having an input and an output, wherein the input is coupled to the controller and is configured to receive and amplify an input signal to generate a first output signal into a load coupled to the output of the first power amplifier circuit; and a second power amplifier circuit having an input and an output, wherein the input is coupled to the controller and is configured to receive and amplify the input signal to generate a second output into the load coupled the output of the second power amplifier circuit; wherein a power rating of the first amplifier circuit is different from a power rating of the second amplifier circuit; and wherein the controller is configured to select the first or the second power amplifier circuit based on power to be produced in the load.

Example 2. The energy module of Example 1, wherein the first power amplifier circuit is a wideband power amplifier circuit and the second power amplifier circuit is a resonant power amplifier circuit.

Example 3. The energy module of any one or more of Examples 1 through 2, wherein the power rating of the first power amplifier circuit is lower than the power rating of the second power amplifier circuit.

Example 4. The energy module of Example 3, wherein the power rating of the first power amplifier circuit is in a range of 1 to 60 watts.

Example 5. The energy module of any one or more of Examples 1 through 4, wherein the power rating of the second power amplifier circuit is higher than the power rating of the second power amplifier circuit.

Example 6. The energy module of Example 5, wherein the power rating of the second amplifier circuit is in a range of 20 to 400 watts.

Example 7. The energy module of any one or more of Examples 1 through 6, wherein at least one of the first or second power amplifier circuits comprises a switching circuit and wherein the controller is configured to apply a switching signal to the switching circuit of the at least one of the first or second power amplifier circuits.

Example 8. The energy module of Example 7, wherein the first power amplifier circuit comprises a comprise a first switching circuit and the second power amplifier circuit comprises a second switching circuit and wherein the controller is configured to apply a first switching signal to the first switching circuit and a second switching signal to second power amplifier circuit.

Example 9. The energy module of Example 7, further comprising a digital-to-analog converter (DAC) coupled between the controller and the first power amplifier circuit, wherein the second power amplifier circuit comprises the switching circuit, and wherein the controller is configured to apply the switching signal to the second amplifier circuit.

Example 10. The energy module of any one of Examples 1 through 9, wherein the controller is configured to generate a waveform having a predetermined wave shape and frequency based on the load coupled to the output of the first or second power amplifier circuit.

Example 11. The energy module of Example 10, wherein the controller is configured to limit current, power, and voltage of the waveform based on impedance of the load coupled to the output of the first or second power amplifier circuit.

Example 12. The energy module of any one or more of Examples 10 through 11, wherein the controller is configured to select at least one of the first or second power amplifier circuits based on power to be produced in the load coupled to the output of the at least one of the first or second power amplifier circuits.

Example 13. The energy module of Example 12, further comprising a digital-to-analog converter (DAC) coupled between the controller and at least one of the first or second power amplifier circuits, wherein the DAC receives the waveform in digital form and provides an analog waveform to the input of the at least one of the first or second power amplifier circuits.

Example 14. The energy module of Example 13, wherein the DAC provides the analog waveform to the input of either the first or second power amplifier circuit based on power to be produced in the load coupled to the output of the first or second power amplifier circuit.

Example 15. The energy module of Example 14, further comprising: a first switch coupled between the DAC output and the input of the first power amplifier circuit; and a second switch coupled between the DAC output and the input of the second power amplifier input; wherein the first and second switches are controlled by the controller via first and second switch select lines to select the first or second power amplifier circuit based on the power to be produced in the load coupled to the output of the first or second power amplifier circuit.

Example 16. The energy module of any one or more of Examples 14 through 15, wherein the first or second power amplifier circuit is selectable by the controller and wherein the controller is configured to select the first or second power amplifier circuit based on the power to be produced in the load coupled to the output of the first or second power amplifier circuit.

Example 17. A method of delivering power to a load coupled to an energy module, the method comprising: generating, by a controller, a digital waveform having a predetermined wave shape and frequency; converting, by a digital-to-analog converter (DAC) coupled to the controller, the digital waveform to an analog waveform; selecting, by the controller, a first power amplifier circuit or a second power amplifier circuit based on a predetermined power output to be produced by the first or second power amplifier circuit into a load coupled to an energy output port of the energy module; coupling, by the controller, the analog waveform to the selected first or second power amplifier circuit; and producing, by the selected first or second power amplifier circuit the predetermined power output into the load coupled to the energy output port of the energy module.

Example 18. The method of Example 17, comprising: selecting, by the controller, a first switch coupled between the DAC and the first power amplifier to produce a first power output into the load coupled to the output of the first power amplifier via an energy output port; or selecting, by the controller, a second switch coupled between the DAC and the second power amplifier to produce a second power output into the load coupled to the output of the second power amplifier via an energy output port.

Example 19. The method of any one or more of Examples 17 through 18, comprising: selecting, by the controller, the first power amplifier via a first amplifier select signal to produce a first power output into the load coupled to the output of the first power amplifier via an energy output port; or selecting, by the controller, the second power amplifier via a second amplifier select signal to produce a second power output into the load coupled to the output of the second power amplifier via an energy output port.

Example 20. The method of any one or more of Examples 17 through 19, comprising: determining, by the controller, the load coupled to the output of the energy module; and generating, by the controller, a waveform having a predetermined wave shape and frequency.

Example 21. The method of any one or more of Examples 17 through 20, comprising: limiting, by the controller, current, power, and voltage of the waveform based on an impedance of the load coupled to the output of the first or second power amplifier circuit.

Example 22. The method of any one or more Examples 17 through 21, comprising: applying, by the controller, a switching signal to the input of the second amplifier circuit.

Example 23. An energy module configured to deliver power to a load coupled thereto, the energy module comprising: a digital-to-analog converter (DAC) configured to convert a digital waveform to an analog waveform; a controller coupled to the DAC, the controller configured to: generate the digital waveform having a predetermined wave shape and frequency; select a first power amplifier circuit or a second power amplifier circuit based on a predetermined power output to be produced by the first or second power amplifier circuit into a load coupled to an energy output port of the energy module; and couple the analog waveform to the selected first or second power amplifier circuit to produce, by the selected first or second power amplifier circuit the predetermined power output into the load coupled to the energy output port of the energy module.

Example 24. The energy module of Example 23, wherein controller is configured to: select a first switch coupled between the DAC and the first power amplifier to produce a first power output into the load coupled to the output of the first power amplifier via an energy output port; or select a second switch coupled between the DAC and the second power amplifier to produce a second power output into the load coupled to the output of the second power amplifier via an energy output port.

Example 25. The energy module of any one or more Examples 23 through 24, wherein the controller is configured to: select the first power amplifier via a first amplifier select signal to produce a first power output into the load coupled to the output of the first power amplifier via an energy output port; or select the second power amplifier via a second amplifier select signal to produce a second power output into the load coupled to the output of the second power amplifier via an energy output port.

Example 26. The energy module of any one or more of Examples 23 through 25, wherein the controller is configured to: determine the load coupled to the output of the energy module; and generate a waveform having a predetermined wave shape and frequency.

Example 27. The energy module of any one or more of Examples 23 through 26, wherein the controller is configured to: limit current, power, and voltage of the waveform based on an impedance of the load coupled to the output of the first or second power amplifier circuit.

Example 28. The energy module of anyone or more of Examples 23 through 27, wherein the controller is configured to: apply a switching signal to the input of the second amplifier circuit.

Modular Energy System with Multi-Energy Port Splitter for Multiple Energy Devices Having described a general implementation the header and modules of modular energy systems 2000, 3000, 6000, and various surgical instruments usable therewith, for example, surgical instruments 2204, 2206, and 2208, the disclosure now turns to describe various aspects of modular energy systems comprising a multi-energy port splitter for multiple energy devices. In other aspects, these modular energy systems are substantially similar to the modular energy system 2000, the modular energy system 3000, and/or the modular energy system 6000 described hereinabove. For the sake of brevity, various details of the other modular energy systems being described in the following sections, which are similar to the modular energy system 2000, the modular energy system 3000, and/or the modular energy system 6000, are not repeated herein. Any aspect of the other modular energy systems described below can be brought into the modular energy system 2000, the modular energy system 3000, or the modular energy system 6000.

As described hereinbelow with reference to FIGS. 30-33, in various aspects, the present disclosure provides modular energy systems 2000, 3000, 6000 comprising one or more than one multi-energy port splitters for multiple energy devices. In one aspect, the present disclosure provides modular energy systems 2000, 3000, 6000 comprising a single energy port input to support for multiple energy devices at the output. In another aspect, the present disclosure provides modular energy systems 2000, 3000, 6000 comprising backplane architectures for the multi-energy port splitter.

Single Energy Port Support for Multiple Energy Devices

According to various aspects, the present disclosure provides a modular energy system comprising an energy module capable of driving two or more surgical instruments from one energy port non-simultaneously. By way of example and not limitation, during certain surgical procedures there is a need for an energy module to drive multiple surgical instruments from one energy output port non-simultaneously to perform certain target activities. Using an external splitter controlled by the modular energy system to multiplex multiple surgical instruments from a single energy port is useful in robotic surgery applications where the need for multiple energy modules is not required but the ability to drive more than one instrument is often required. In one aspect, the external splitter is transparent to the robot software. In various aspects, as explained below, a single energy output port of an energy module can be multiplexed to two or more surgical instruments including multiple energy modalities, such as, for example, bipolar RF, monopolar RF, advanced bipolar RF combined with ultrasonic, and/or ultrasonic energy modalities. It will be appreciated that any details of the modular energy systems 2000, 3000, 6000 described above are incorporated by reference in the following description of FIGS. 30-33.

Figure 30:
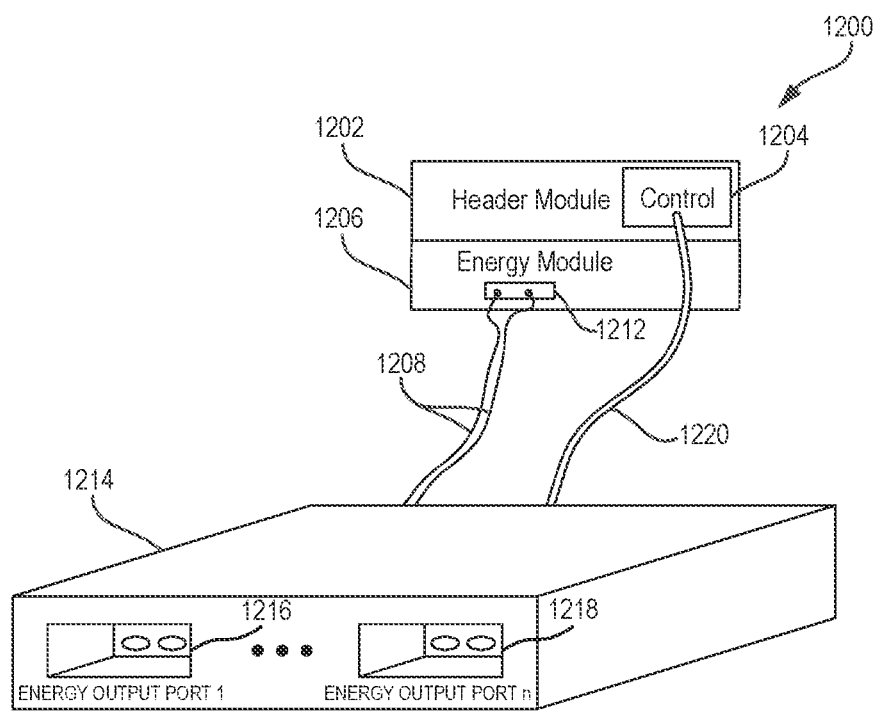
FIG. 30 shows a modular energy system comprising a header module, an energy module, and a multi-energy port splitter coupled thereto, in accordance with at least one aspect of the present disclosure.

Turning now to FIG. 30, there is shown a modular energy system 1200 comprising a header module 1202, an energy module 1206, and a multi-energy port splitter 1214 coupled thereto, in accordance with at least one aspect of the present disclosure. The header module 1202 is capable of controlling the multi-energy port splitter 1214 (e.g., and n-energy port splitter, where n is an integer greater than one) via a control line 1220 to the control port 1204 of the header module 1202, which may be an accessory port of the header module 1202, for example. The multi-energy port splitter 1214 can demultiplex an energy modality coming into a single node and switches it to multiple output nodes at different times. In the illustrated example, the multi-energy port splitter 1214 demultiplexes the single energy output port 1212 of the energy module 1206 up to n energy output ports from a first energy output port 1216 up to an n-th energy output port 1218, where n is an integer greater than one. For example, for a 1-to-2 energy output port expansion (e.g., demultiplex) n=2; for a 1-to-3 energy output port expansion n=3; for a 1-to-4 energy output port expansion n=4; and so on. Any energy modality such as, for example, bipolar RF, monopolar RF, bipolar RF combined with ultrasonic, and/or ultrasonic energy modalities received at an input node of the multi-energy port splitter 1214 can be demultiplexed in multiple energy output ports 1216, 1218 at different times.

The energy module 1206 comprises an energy output port 1212 capable of supplying any energy modality from the energy module 1206 to an input node of the multi-energy port splitter 1214 via an energy supply line 1208. The energy supply line 1208 is coupled to an input node of the multi-energy port splitter 1214. In one aspect, the energy module 1206 is configured to select which one of the n-energy output ports 1216, 1218 to activate. In another aspect, the energy module 1206 is configured to control n-surgical instruments connected to one of the n-energy output ports 1216, 1218. A first surgical instrument is couplable to the first energy output port 1216 and up to an n-th surgical instrument is couplable to the n-th energy output port 1218. The n-surgical instruments can be independently activated and controlled by the energy module 1206. Accordingly, the surgical instruments may comprise any suitable energy device such as bipolar RF devices, monopolar RF devices, bipolar RF/ultrasonic combination devices, and/or ultrasonic devices, for example.

Figure 31:
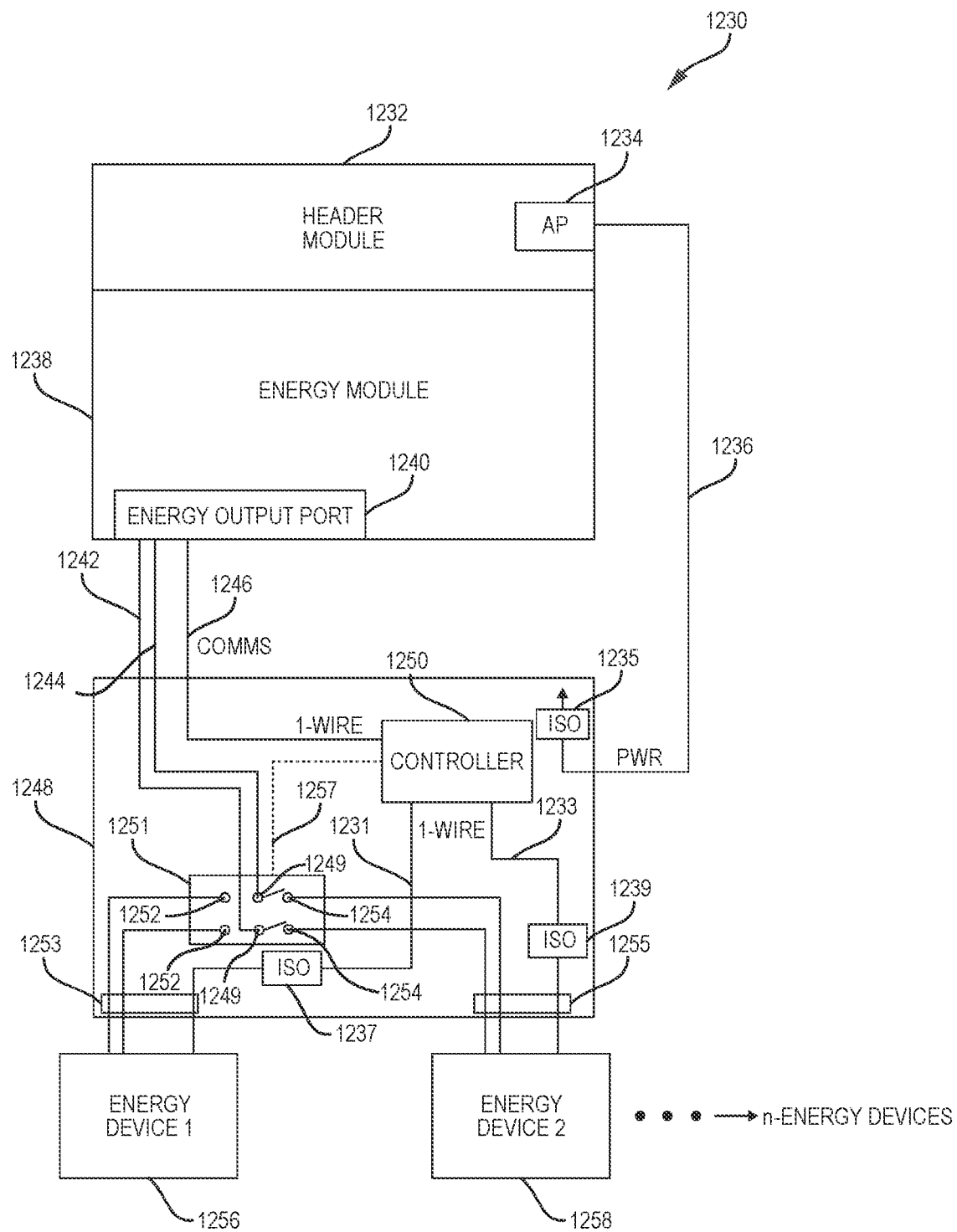
FIG. 31 shows a modular energy system comprising a header module, an energy module, and a multi-energy port splitter coupled thereto, in accordance with at least one aspect of the present disclosure.

Turning now to FIG. 31, there is shown a modular energy system 1230 comprising a header module 1232, an energy module 1238, and a multi-energy port splitter 1248 coupled thereto, in accordance with at least one aspect of the present disclosure. The header module 1232 provides power to the multi-energy port splitter 1248 through an accessory port 1234 (AP) via a power line 1236 through an isolated power supply 1235. The multi-energy port splitter 1248 expands the single energy output port 1240 of the energy module 1238 into two energy output ports 1253, 1255 configured to drive an energy device 1256 and a second energy device 1258 at different times. It will be appreciated that the multi-energy port splitter 1248 may be replaced with an n-energy port splitter, as discussed in FIG. 30, to expand the single energy output port 1240 of the energy module 1238 into n-energy output ports to drive n-energy devices at different times. The energy output port 1240 may supply any energy modality such as, for example, bipolar RF, monopolar RF, bipolar RF combined with ultrasonic, and/or ultrasonic energy modalities. Accordingly, the energy devices 1256, 1258 may be bipolar RF devices, monopolar RF devices, bipolar RF/ultrasonic combination devices, and/or ultrasonic devices, for example.

In one aspect, the multi-energy port splitter 1248 comprises an input node 1249 to receive an energy signal from the energy output port 1240 of the energy module 1238. The energy signal is carried by first and second lines 1242, 1244, where the first line 1242 is coupled to a first pole (e.g., active pole) of an energy source and the second line 1244 is coupled to a second pole (e.g., return electrode) of the energy source of the energy module 1238. The energy source may be a bipolar RF energy source, a monopolar RF energy source, a combination bipolar RF/ultrasonic energy source, and/or an ultrasonic energy source, among other energy sources.

In one aspect, the multi-energy port splitter 1248 comprises an electronically controlled power switch 1251 to switch the energy input from the energy module 1238 received at the input node 1249 to two or more output nodes 1252, 1254 to supply energy to two or more energy devices 1256, 1256 coupled to two or more energy output ports 1253, 1255. In the example where the input node 1249 is switched to two output nodes 1252, 1254 the electronically controlled power switch 1251 may be a double pole double throw (DPDT) switch that is electronically controlled by a controller 1250 via a power switch control line 1257. In other aspects, the electronically controlled power switch 1251 may be implemented with two single pole double throw (SPDT) switches or four single pole single throw (SPST) switches, among other switch configurations. In various aspects, the electronically controlled power switch 1251 may comprise additional switches and output nodes to accommodate up to n-energy output ports to couple to up to n-energy devices, for example.

In one aspect, the multi-energy port splitter 1248 further comprises a controller 1250 connected to the energy module 1238 via a communication line 1246. In one aspect, the controller 1250 may be implemented as an FPGA circuit, although it can be implemented using a processor or microcontroller circuit, without limitation. The controller 1250 is electrically connected to a control input of the electronically controlled power switch 1251 via the power switch control line 1257 to control which of the output nodes 1252, 1254 connects the input node 1249 to the energy output ports 1253, 1255. Accordingly, in operation, the controller 1250 selects which energy device 1256, 1258 should be powered based on data received from the energy module 1238 transmitted over the communication line 1246. The controller 1250 is capable of communicating commands and data to the first energy device 1256 via a first communication bus 1231 and to the second energy device 1258 via a second communication bus 1233. Additional communication busses may be added as additional energy output ports and energy devices are added to the multi-energy port splitter 1248. The first and second communication busses 1231, 1233 may be serial communication busses such as, for example, a 1-Wire device communication bus. The communication busses 1231, 1233 are isolated from the first and second bipolar instruments 1256, 1258 through electrical isolation circuits 1237, 1239 such as, for example, isolation transformers, optical isolators (e.g., opto-couplers), capacitive isolators, among other isolation circuit techniques. Commands and data may be communicated to the first and second bipolar instruments 1256, 1258 via the first and second communication busses 1231, 1233.

In one aspect, the communication line 1246 is a serial communication bus, such as, for example, a 1-Wire device communication bus. The communication line 1246 transmits control signals to the controller 1250 from the energy module 1238. Accordingly either the energy module 1238 or the header module 1232 is configured to transmit control signals to the controller 1250 to select one of the energy devices 1256, 1258 connected to the energy output ports 1253, 1255. in an alternate aspect, the header module 1232 (instead of the energy module 1238) can transmit control signals to the controller 1250 via a communication line on the accessory port 1234.

Backplane Architectures for Multi-Energy Port Splitter

Figure 32:
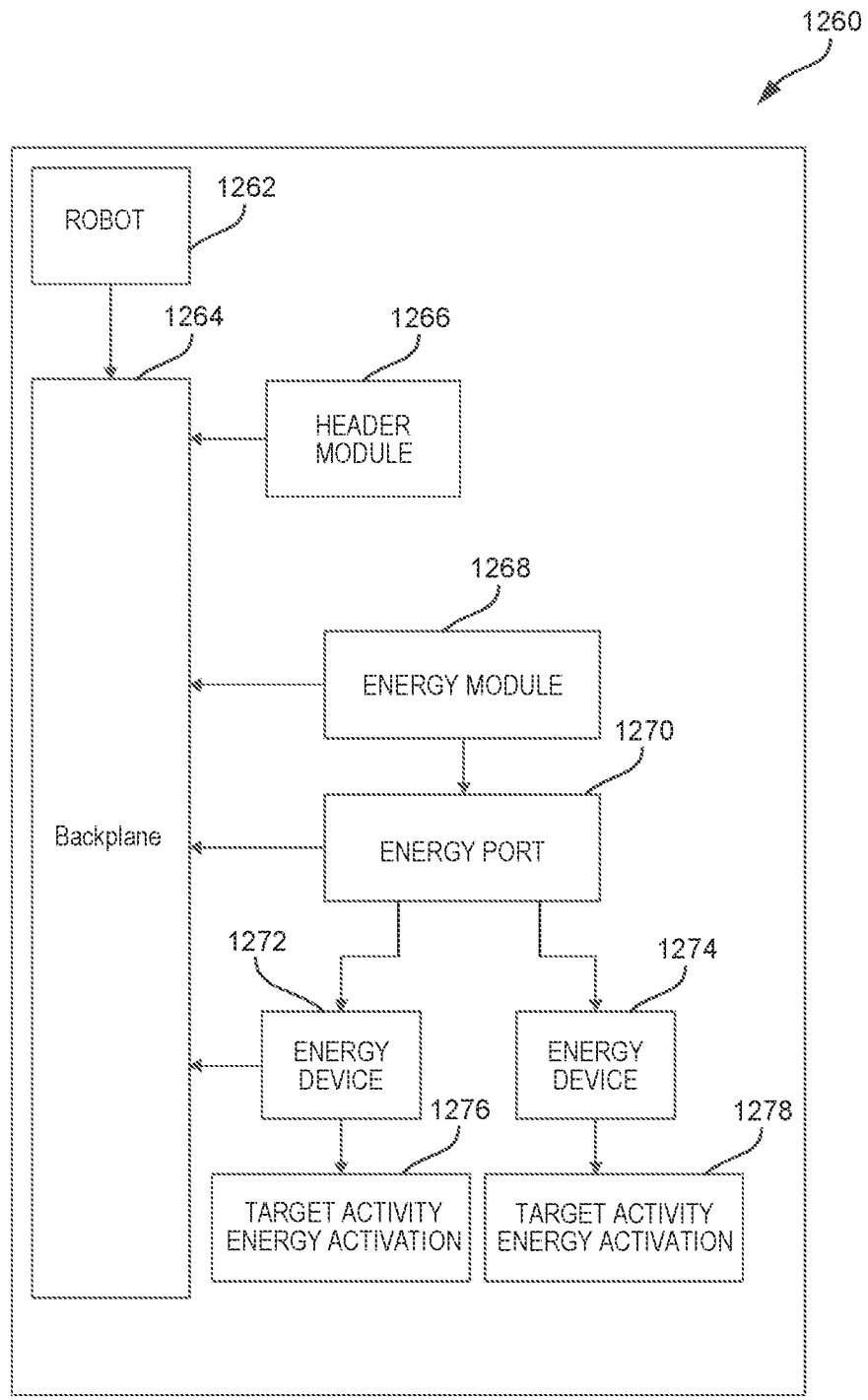
FIG. 32 shows a data backplane architecture for a modular energy system where the data backplane architecture is supported on actual physical backplane communication interfaces and a multi-energy port splitter presents as two energy devices, in accordance with at least one aspect of the present disclosure.
Figure 33:
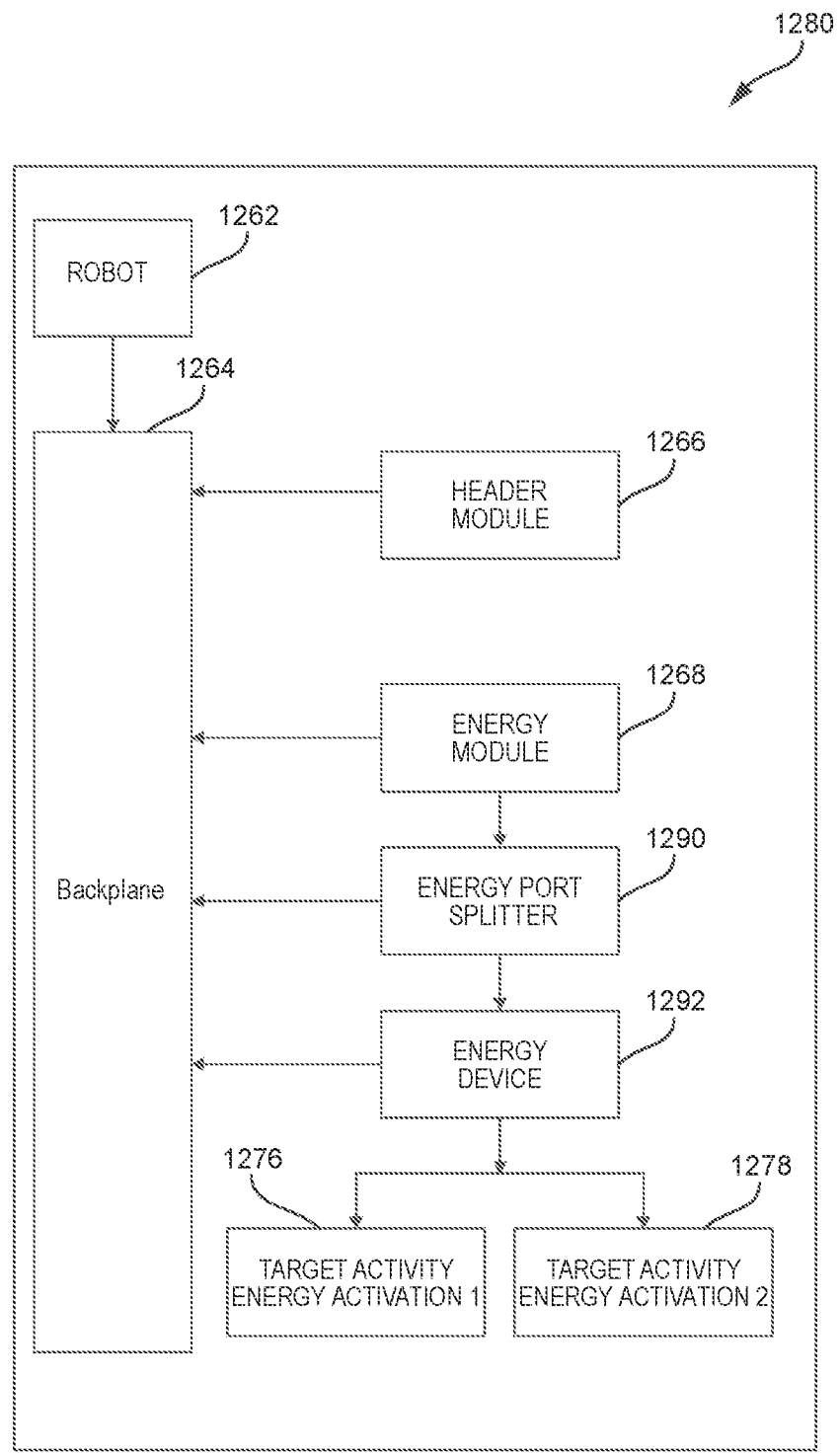
FIG. 33 shows a data backplane architecture for a modular energy system where the data backplane architecture is supported on an actual physical backplane communication interface and a multi-energy port splitter presents as a type of energy device, in accordance with at least one aspect of the present disclosure.

Turning now to FIGS. 32 and 33, the modular energy systems 2000, 3000, 6000 described herein utilize a data backplane architecture 1260, 1280 supported on an actual physical backplane communication interface 1264, in accordance with at least one aspect of the present disclosure. In one aspect, the data backplane architecture 1260, 1280 is supported on actual physical backplane communication interface 1264 using DDS, for example. The data backplane architecture 1260, 1280 shown in FIGS. 32 and 33 are intended to depict potential ways in which an energy port splitter may be represented within a data backplane model. In this way, the various data contained in the modular energy system 2000, 3000, 6000 are contained within a data model consistent throughout the modular energy system 2000, 3000, 6000. For example, any of the energy delivery ports 1270 may present as a "port" in the data backplane model, with further specification as "monopolar," "bipolar," etc. This can allow, for example, the header module 1266 to determine which energy ports 1270 are available for use by a given energy module 1268. This is particularly useful as future modules of the modular energy system 2000, 3000, 6000 may have varying capabilities.

As described herein, a "target activity" represents "something you can do" for a given energy device 1272, 1274, 1292. An energy device 1272, 1274, 1292 has a target activity of "BP Activation" 1276, 1278 also known as "Energy Delivery." Some types of energy devices 1272, 1274, 1292 may have multiple potential target activities 1276, 1278. As described above, the energy delivery includes delivery of bipolar RF, monopolar RF, advanced bipolar RF combined with ultrasonic, and/or ultrasonic energy modalities, among other energy modalities. Accordingly, energy devices includes bipolar RF, monopolar RF, advanced bipolar RF combined with ultrasonic, and/or ultrasonic energy devices, among other energy devices.

FIG. 32 shows a data backplane architecture 1260 for a modular energy system 2000, 3000, 6000 where the data backplane architecture 1260 is supported on an actual physical backplane communication interface 1264 and a multi-energy port splitter presents as two energy devices 1272, 1274, in accordance with at least one aspect of the present disclosure. FIG. 32, for example, depicts that an multi-energy port splitter, such as the multi-energy port splitters 1214, 1248 shown in FIGS. 30 and 31, does not directly present itself in the data backplane model but, rather, allows for the direct presentation of two energy devices 1272, 1274 within the data backplane model, whereas only one such energy device 1272 or 1274 would be supported by the energy module 1268 absent the energy port splitter. Because of this, a robot 1262 coupled to the backplane interface 1264 and the rest of the modular energy system may remain agnostic to the presence of an energy port splitter and may operate only on the knowledge that there are two energy devices 1272, 1274 available for use. Particularly advantageous, is that the robot 1262 may be configured to operate with this presentation and then, if in the future an energy module 1268 with support for two energy devices 1272, 1274 is installed, the robot 1262 will not "detect" any difference in the data backplane model being presented in.

FIG. 33 shows a data backplane architecture 1280 for a modular energy system 2000, 3000, 6000 where the data backplane architecture 1280 is supported on an actual physical backplane communication interface 1264 and a multi-energy port splitter presents as a type of energy device 1292, in accordance with at least one aspect of the present disclosure. The data backplane architecture 1280 shown in FIG. 33 is an alternative way of presenting the multi-energy port splitter, such as the multi-energy port splitters 1214, 1248 shown in FIGS. 30 and 31, on the data backplane model. In this case, the energy port 1290 (adapter) is presented as its own type of energy device 1292—this time with two unique Target Activities available for use. Energy Activation 1. Target Activity 1276 corresponds to providing energy to a first energy port on the multi-energy port splitter, and Energy Activation 2. Target Activity 1278 corresponds to providing energy to a second energy port on the multi-energy port splitter. In this way, the presence of the energy port splitter is known and presented within the data backplane model, but within the existing norms of the Energy Port>Energy Device>Target Activity hierarchy.

Examples

Various aspects of a modular energy systems comprising multi-energy port splitters for multiple energy devices described herein with reference to FIGS. 30-33 are set out in the following numbered examples.

Example 1. A multi-energy port splitter for a modular energy system, the multi-energy port splitter comprising: an input port configured to couple to an energy output port of an energy module; a first energy output port configured to deliver energy supplied by the energy output port of the energy module; at least a second energy output port configured to deliver the energy supplied by the energy output port of the energy module; an electronically controlled power switch configured to switch energy received at the input port to one of the first energy output port or the at least second energy output port; and a controller configured to couple to the energy module through a first communication bus, wherein the controller is electrically coupled to the electronically controlled power switch through a power switch control line.

Example 2. The multi-energy port splitter of Example 1, wherein the electronically controlled power switch comprises an input node coupled to the input port, one output node coupled to the first energy output port, and at least a second output node coupled to the second energy output port.

Example 3. The multi-energy port splitter of Example 2, wherein the electronically controlled power switch comprises a plurality of output nodes coupled to a plurality of energy output ports, wherein each one of the plurality of output nodes is coupled to one of the plurality of energy output ports.

Example 4. The multi-energy port splitter of any one or more of Examples 1 through 3, wherein the electronically controlled power switch comprises multiple switches.

Example 5. The multi-energy port splitter of any one or more of Examples 1 through 4, wherein the first energy output port is electrically coupled to the controller via a second communication bus, wherein the controller is configured to communicate to a surgical instrument electrically coupled to the first energy output port via the second communication bus.

Example 6. The multi-energy port splitter of Example 5, wherein the at least second energy output port is electrically coupled to the controller via at least a third communication bus, wherein the controller is configured to communicate to the surgical instrument electrically coupled to the at least second energy output port via the at least third communication bus.

Example 7. The multi-energy port splitter of Example 6, further comprising a plurality of energy output ports electrically coupled to the controller via a plurality of communication busses, wherein each one of the plurality of energy output ports is coupled to one of the plurality of communication busses.

Example 8. The multi-energy port splitter of Example 7, wherein each one of the plurality of communication busses is a serial communication bus.

Example 9. The multi-energy port splitter of Example 8, wherein the plurality of communication busses is isolated from the plurality of energy output ports through a plurality of isolation circuits, wherein each one of the plurality of energy output ports is coupled to one of the plurality of communication busses though one of the plurality of isolation circuits.

Example 10. The multi-energy port splitter of any one or more of Examples 1 through 9, further comprising an energy module electrically coupled to the multi-energy port splitter.

Example 11. The multi-energy port splitter of Example 10, further comprising a header module electrically coupled to the energy module and to the multi-energy port splitter.

Example 12. The multi-energy port splitter of Example 11, wherein the header module is configured to send control data to the controller to select the first or the at least second energy output ports through the electrically controlled power switch and wherein the energy module is configured to deliver energy to the electrically controlled power switch.

Example 13. A modular energy system, comprising: a backplane comprising a plurality of backplane communication interfaces, wherein at least one of the plurality of communication interfaces is configured to receive at least one multi-energy port splitter and at least one other backplane communication interface is configured to receive an energy module; wherein the at least one multi-energy port splitter is presented as an energy delivery port to the energy module.

Example 14. The modular energy system of Example 13, wherein the at least one multi-energy port splitter is presented to the energy module as a plurality of energy devices available for use.

Example 15. The modular energy system of Example 14, wherein the energy module is configured to operate at least one of the plurality of energy devices for a first target activity and at least one of the plurality of energy devices for a second target activity.

Example 16. The modular energy system of any one or more of Examples 13 through 15, wherein the at least one multi-energy port splitter is presented to the energy module as a type of energy device.

Example 17. The modular energy system of Example 16, wherein the energy module is configured to operate the energy device for: a first target activity through a first energy port of the multi-energy port splitter; and a second target activity through a second energy port of the multi-energy port splitter.

Example 18. A modular energy system, comprising: a header module; at least one energy module coupled to the header module, the energy module comprising an energy output port; and a multi-energy port splitter for a modular energy system, the multi-energy port splitter comprising: an input port coupled to the energy output port of the energy module; a first energy output port configured to deliver energy supplied by the energy output port of the energy module; at least a second energy output port configured to deliver the energy supplied by the energy output port of the energy module; an electronically controlled power switch configured to switch energy received at the input port to one of the first energy output port or the at least second energy output port; and a controller configured to couple to the energy module through a first communication bus, wherein the controller is electrically coupled to the electronically controlled power switch through a power switch control line.

Example 19. The modular energy system of Example 18, wherein the electronically controlled power switch comprises an input node coupled to the input port, one output node coupled to the first energy output port, and at least a second output node coupled to the second energy output port.

Example 20. The modular energy system of Example 19, wherein the electronically controlled power switch comprises a plurality of output nodes coupled to a plurality of energy output ports, wherein each one of the plurality of output nodes is coupled to one of the plurality of energy output ports.

Example 21. The modular energy system of any one or more of Examples 18 through 20, wherein the electronically controlled power switch comprises multiple switches.

Example 22. The modular energy system of any one or more of Examples 18 through 21, wherein the first energy output port is electrically coupled to the controller via a second communication bus, wherein the controller is configured to communicate to a surgical instrument electrically coupled to the first energy output port via the second communication bus.

Example 23. The modular energy system of Example 22, wherein the at least second energy output port is electrically coupled to the controller via at least a third communication bus, wherein the controller is configured to communicate to the surgical instrument electrically coupled to the at least second energy output port via the at least third communication bus.

Example 24. The modular energy system of Example 23, further comprising a plurality of energy output ports electrically coupled to the controller via a plurality of communication busses, wherein each one of the plurality of energy output ports is coupled to one of the plurality of communication busses.

Example 25. The modular energy system of Example 24, wherein each one of the plurality of communication busses is a serial communication bus.

Example 26. The modular energy system of Example 25, wherein the plurality of communication busses is isolated from the plurality of energy output ports through a plurality of isolation circuits, wherein each one of the plurality of energy output ports is coupled to one of the plurality of communication busses though one of the plurality of isolation circuits.

Example 27. The modular energy system of any one or more of Examples 18 through 26, further comprising an energy module electrically coupled to the multi-energy port splitter.

Example 28. The modular energy system of Example 27, further comprising a header module electrically coupled to the energy module and to the multi-energy port splitter.

Example 29. The modular energy system of Example 28, wherein the header module is configured to send control data to the controller to select the first or the at least second energy output ports through the electrically controlled power switch and wherein the energy module is configured to deliver energy to the electrically controlled power switch.

Examples

Various aspects of methods of delivering power to a load coupled to an energy module of a modular energy system, are set out in the following numbered examples.

Example 1. A method of delivering power to a load coupled to an energy module, the method comprising: determining, by a controller, a power to be produced in a load coupled to the controller; generating, by the controller, a signal; and selecting, by the controller, either a first power amplifier circuit or a second amplifier circuit based on the power to be produced in the load; wherein a power rating of the first amplifier circuit is different from a power rating of the second amplifier circuit.

Example 2. The method of Example 1, wherein the first power amplifier circuit is a wideband power amplifier circuit and the power rating of the first power amplifier circuit is lower than the power rating of the second power amplifier circuit, the method comprising amplifying the signal by the wideband power amplifier Example 3. The method of Example 2, comprising producing power in the load in a range of 1 to 60 watts.

Example 4. The method of any one or more of Examples 1 through 3, wherein the second amplifier circuit is a resonant circuit and the power rating of the second power amplifier circuit is higher than the power rating of the second power amplifier circuit, the method comprising producing power in the load in a range of 20 to 400 watts.

Example 5. The method of any one or more of Examples 1 through 4, wherein at least one of the first or second power amplifier circuits comprises a switching circuit, the method comprising applying, by the controller a switching signal to the switching circuit of the at least one of the first or second power amplifier circuits.

Example 6. The method of Example 5, wherein the first power amplifier circuit comprises a first switching circuit and the second power amplifier circuit comprises a second switching circuit, the method comprising applying, by the controller, a first switching signal to the first switching circuit and a second switching signal to second power amplifier circuit.

Example 7. The method of Example 5, further comprising a digital-to-analog converter (DAC) coupled between the controller and the first power amplifier circuit, wherein the second power amplifier circuit comprises the switching circuit, the method comprising applying, by the controller, the switching signal to the second amplifier circuit.

Example 8. The method of any one or more of Examples 1 through 7, comprising generating, by the controller, a waveform having a predetermined wave shape and frequency based on the load coupled to the output of the first or second power amplifier circuit.

Example 9. The method of Example 8, comprising limiting, by the controller, current, power, and voltage of the waveform based on impedance of the load coupled to the output of the first or second power amplifier circuit.

Example 10. The method of Example 8, comprising selecting, by the controller, at least one of the first or second power amplifier circuits based on power to be produced in the load coupled to the output of the at least one of the first or second power amplifier circuits.

Example 11. The method of Example 10, further comprising a digital-to-analog converter (DAC) coupled between the controller and at least one of the first and second power amplifier circuits, the method comprising receiving, by the DAC, the waveform in digital form and providing, by the DAC, an analog waveform to the input of the at least one of the first or second power amplifier circuits.

Example 12. The method of Example 11, comprising providing, by the DAC, the analog waveform to the input of either the first or second power amplifier circuit based on power to be produced in the load coupled to the output of the first or second power amplifier circuit.

Example 13. The method of Example 12, further comprising: a first switch coupled between the DAC output and the input of the first power amplifier circuit; and a second switch coupled between the DAC output and the input of the second power amplifier input; the method comprising: controlling, by the controller, the first and second switches via first and second switch select lines; and selecting, by the controller, the first or second power amplifier circuit based on the power to be produced in the load coupled to the output of the first or second power amplifier circuit.

Example 14. The method of Example 12, wherein the first or second power amplifier circuit is selectable by the controller, the method comprising selecting, by the controller, the first or second power amplifier circuit based on the power to be produced in the load coupled to the output of the first or second power amplifier circuit.

Example 15. A method of delivering power to a load coupled to an energy module, the method comprising: generating, by a controller, a digital waveform having a predetermined wave shape and frequency; converting, by a digital-to-analog converter (DAC) coupled to the controller, the digital waveform to an analog waveform; selecting, by the controller, a first power amplifier circuit or a second power amplifier circuit based on a predetermined power output to be produced by the first or second power amplifier circuit into a load coupled to an energy output port of the energy module; coupling, by the controller, the analog waveform to the selected first or second power amplifier circuit; and producing, by the selected first or second power amplifier circuit, the predetermined power output into the load coupled to the energy output port of the energy module.

Example 16. The method of Example 15, comprising: selecting, by the controller, a first switch coupled between the DAC and the first power amplifier to produce a first power output into the load coupled to the output of the first power amplifier via an energy output port; or selecting, by the controller, a second switch coupled between the DAC and the second power amplifier to produce a second power output into the load coupled to the output of the second power amplifier via an energy output port.

Example 17. The method of any one or more of Examples 15 through 16, comprising: selecting, by the controller, the first power amplifier via a first amplifier select signal to produce a first power output into the load coupled to the output of the first power amplifier via an energy output port; or selecting, by the controller, the second power amplifier via a second amplifier select signal to produce a second power output into the load coupled to the output of the second power amplifier via an energy output port.

Example 18. The method of any one or more of Examples 15 through 17, comprising: determining, by the controller, the load coupled to the output of the energy module; and generating, by the controller, a waveform having a predetermined wave shape and frequency.

Example 19. The method of any one or more of Examples 15 through 18, comprising: limiting, by the controller, current, power, and voltage of the waveform based on an impedance of the load coupled to the output of the first or second power amplifier circuit.

Example 20. The method of an one or more of Examples 15 through 19, comprising: applying, by the controller, a switching signal to the input of the second amplifier circuit.

While several forms have been illustrated and described, it is not the intention of Applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" may refer to, for example, hardwired circuitry, programmable circuitry (e.g., a computer processor including one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

A network may include a packet switched network. The communication devices may be capable of communicating with each other using a selected packet switched network communications protocol. One example communications protocol may include an Ethernet communications protocol which may be capable permitting communication using a Transmission Control Protocol/Internet Protocol (TCP/IP). The Ethernet protocol may comply or be compatible with the Ethernet standard published by the Institute of Electrical and Electronics Engineers (IEEE) titled "IEEE 802.3 Standard", published in December, 2008 and/or later versions of this standard. Alternatively or additionally, the communication devices may be capable of communicating with each other using an X.25 communications protocol. The X.25 communications protocol may comply or be compatible with a standard promulgated by the International Telecommunication Union-Telecommunication Standardization Sector (ITU-T). Alternatively or additionally, the communication devices may be capable of communicating with each other using a frame relay communications protocol. The frame relay communications protocol may comply or be compatible with a standard promulgated by Consultative Committee for International Telegraph and Telephone (CCITT) and/or the American National Standards Institute (ANSI). Alternatively or additionally, the transceivers may be capable of communicating with each other using an Asynchronous Transfer Mode (ATM) communications protocol. The ATM communications protocol may comply or be compatible with an ATM standard published by the ATM Forum titled "ATM-MPLS Network Interworking 2.0" published August 2001, and/or later versions of this standard. Of course, different and/or after-developed connection-oriented network communication protocols are equally contemplated herein.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

The invention claimed is:

1. A method of delivering power to a load coupled to an energy module, the method comprising:
   determining, by a controller, the power to be produced for the load coupled to the controller, wherein the load is defined by a surgical instrument coupled to the energy module;
   generating, by the controller, a waveform having a predetermined wave shape and frequency based on the load coupled to an output of a first power amplifier circuit or a second power amplifier circuit;
   selecting, by the controller, either the first or second amplifier circuit based on the power to be produced for the load;
   limiting, by the controller, current, power, and voltage of the waveform based on impedance of the load coupled to the output of the first or second power amplifier circuit; and
   wherein a power rating of the first amplifier circuit is different from a power rating of the second amplifier circuit.

2. The method of claim 1, wherein the first power amplifier circuit is a wideband power amplifier circuit and the power rating of the first power amplifier circuit is lower than the power rating of the second power amplifier circuit, the method comprising amplifying the waveform by the wideband power amplifier.

3. The method of claim 2, comprising producing power in the load in a range of 1 to 60 watts.

4. The method of claim 1, wherein the second amplifier circuit is a resonant circuit and the power rating of the second power amplifier circuit is higher than the power rating of the first power amplifier circuit, the method comprising producing power in the load in a range of 20 to 400 watts.

5. The method of claim 1, wherein at least one of the first or second power amplifier circuits comprises a switching circuit, the method comprising applying, by the controller a switching signal to the switching circuit of the at least one of the first or second power amplifier circuits.

6. The method of claim 5, wherein the first power amplifier circuit comprises a first switching circuit and the second power amplifier circuit comprises a second switching circuit, the method comprising applying, by the controller, a first switching signal to the first switching circuit and a second switching signal to second power amplifier circuit.

7. The method of claim 5, further comprising a digital-to-analog converter (DAC) coupled between the controller and the first power amplifier circuit, wherein the second power amplifier circuit comprises the switching circuit, the method comprising applying, by the controller, the switching signal to the second amplifier circuit.

8. The method of claim 1, comprising selecting, by the controller, at least one of the first or second power amplifier circuits based on power to be produced for the load coupled to the output of the at least one of the first or second power amplifier circuits.

9. The method of claim 8, further comprising a digital-to-analog converter (DAC) coupled between the controller and at least one of the first and second power amplifier circuits, the method comprising receiving, by the DAC, the waveform in digital form and providing, by the DAC, an analog waveform to an input of the at least one of the first or second power amplifier circuits.

10. The method of claim 9, comprising providing, by the DAC, the analog waveform to the input of either the first or second power amplifier circuit based on power to be produced for the load coupled to the output of the first or second power amplifier circuit.

11. The method of claim 10, further comprising:
   a first switch coupled between the DAC output and the input of the first power amplifier circuit; and
   a second switch coupled between the DAC output and the input of the second power amplifier input;
   the method comprising:
   controlling, by the controller, the first and second switches via first and second switch select lines; and
   selecting, by the controller, the first or second power amplifier circuit based on the power to be produced for the load coupled to the output of the first or second power amplifier circuit.

12. The method of claim 10, wherein the first or second power amplifier circuit is selectable by the controller, the method comprising selecting, by the controller, the first or second power amplifier circuit based on the power to be produced for the load coupled to the output of the first or second power amplifier circuit.

13. The method of claim 1, wherein selecting, by the controller, either the first power amplifier circuit or the second amplifier circuit based on the power to be produced for the load comprises:
   selecting, by the controller, the first power amplifier circuit via a first amplifier select signal to produce a first power output for the load coupled to the output of the first power amplifier circuit via an energy output port; or selecting, by the controller, the second power amplifier circuit via a second amplifier select signal to produce a second power output for the load coupled to the output of the second power amplifier circuit via an energy output port.

14. A method of delivering power to a load coupled to an energy module, the method comprising:

detecting, by a controller, a load coupled to an output of the energy module, wherein the load is defined by a surgical instrument coupled to the energy module;

generating, by the controller, a digital waveform having a predetermined wave shape and frequency based on the load coupled to the output;

converting, by a digital-to-analog converter (DAC) coupled to the controller, the digital waveform to an analog waveform;

selecting, by the controller, a first power amplifier circuit or a second power amplifier circuit based on a predetermined power output to be produced by the first or second power amplifier circuit for the load coupled to an energy output port of the energy module;

limiting, by the controller, current, power, and voltage of the waveform based on an impedance of the load coupled to the output of the first or second power amplifier circuit; and producing, by the selected first or second power amplifier circuit, the predetermined power output for the load based on the analog waveform.

15. The method of claim 14, comprising:

selecting, by the controller, the first power amplifier circuit via a first amplifier select signal to produce a first power output into the load coupled to the output of the first power amplifier circuit via an energy output port; or selecting, by the controller, the second power amplifier circuit via a second amplifier select signal to produce a second power output into the load coupled to the output of the second power amplifier circuit via an energy output port.

16. The method of claim 14, further comprising coupling, by the controller, the analog waveform to the selected first or second power amplifier circuit.

\* \* \* \* \*